US011793788B2

United States Patent
Prybolsky et al.

(10) Patent No.: US 11,793,788 B2
(45) Date of Patent: Oct. 24, 2023

(54) METHODS FOR LOWERING BLOOD SUGAR WITH A DIPEPTIDYL PEPTIDASE-4 INHIBITOR PHARMACEUTICAL COMPOSITION

(71) Applicant: AstraZeneca UK Limited

(72) Inventors: Robert Peter Prybolsky, West Chester, PA (US); Judy Firor, Landenberg, PA (US)

(73) Assignee: ASTRAZENECA UK LIMITED, Cambridge (GB)

( * ) Notice: Subject to any disclaimer, the term of this patent is extended or adjusted under 35 U.S.C. 154(b) by 1168 days.

(21) Appl. No.: 16/440,761

(22) Filed: Jun. 13, 2019

(65) Prior Publication Data

US 2019/0381005 A1 Dec. 19, 2019

Related U.S. Application Data

(60) Provisional application No. 62/685,206, filed on Jun. 14, 2018.

(51) Int. Cl.
*A61K 31/403* (2006.01)
*G16H 70/40* (2018.01)
(Continued)

(52) U.S. Cl.
CPC .......... *A61K 31/403* (2013.01); *A61K 31/513* (2013.01); *A61K 31/522* (2013.01);
(Continued)

(58) Field of Classification Search
CPC .. A61K 31/403; A61K 31/513; A61K 31/522; A61K 31/445; A61K 31/4985;
(Continued)

(56) References Cited

U.S. PATENT DOCUMENTS

| 7,493,264 B1* | 2/2009 | Kelly | G16H 15/00 600/595 |
| 2005/0108053 A1* | 5/2005 | Jones, Jr. | G16H 20/10 705/2 |

(Continued)

FOREIGN PATENT DOCUMENTS

| JP | 2011-503722 | 1/2011 |
| WO | WO 2009061874 | 5/2009 |

(Continued)

OTHER PUBLICATIONS

International Search Report and Written Opinion for International Patent Application No. PCT/US2019/037078, dated Nov. 20, 2019, 28 pages.

(Continued)

*Primary Examiner* — Joy Chng
(74) *Attorney, Agent, or Firm* — Brett A. Lovejoy; Andrew J. Antczak; Morgan, Lewis & Bockius LLP

(57) ABSTRACT

A method is provided for lowering blood sugar in a subject in need thereof by administering a dipeptidyl peptidase-4 inhibitor pharmaceutical composition to a subject qualified for over-the-counter access to the dipeptidyl peptidase-4 inhibitor pharmaceutical composition. In some embodiments, the dipeptidyl peptidase-4 inhibitor pharmaceutical composition includes saxagliptin, sitagliptin, linagliptin, alogliptin, or a pharmaceutically acceptable salt thereof. In some embodiments, the dipeptidyl peptidase-4 inhibitor pharmaceutical composition includes (1S,3S,5S)-2-[(2S)-2-amino-2-(3-hydroxy-1-adamantyl)acetyl]-2-azabicyclo[3.1.0]hexane-3-carbonitrile or a pharmaceutically acceptable salt thereof.

19 Claims, 21 Drawing Sheets

(51) Int. Cl.
| | |
|---|---|
| *G16H 10/20* | (2018.01) |
| *A61P 3/10* | (2006.01) |
| *G06F 16/9038* | (2019.01) |
| *G06F 16/9035* | (2019.01) |
| *A61K 31/513* | (2006.01) |
| *A61K 31/522* | (2006.01) |
| *G06F 9/54* | (2006.01) |

(52) U.S. Cl.
CPC .............. *A61P 3/10* (2018.01); *G06F 9/542* (2013.01); *G06F 16/9035* (2019.01); *G06F 16/9038* (2019.01); *G16H 10/20* (2018.01); *G16H 70/40* (2018.01)

(58) Field of Classification Search
CPC ........ A61P 3/10; G06F 9/542; G06F 16/9035; G06F 16/9038; G16H 10/20; G16H 70/40; G16H 50/20; G16H 20/10
USPC ........................................................... 705/2–3
See application file for complete search history.

(56) References Cited

U.S. PATENT DOCUMENTS

| | | | |
|---|---|---|---|
| 2009/0125324 A1* | 5/2009 | Keravich | G16H 20/10 705/2 |
| 2011/0166876 A1* | 7/2011 | Chapman | G16H 20/10 705/2 |
| 2011/0178812 A1* | 7/2011 | Lindsay | G16H 20/10 705/2 |

FOREIGN PATENT DOCUMENTS

| | | | | |
|---|---|---|---|---|
| WO | WO 2010/041052 A1 | 4/2010 | | |
| WO | WO-2010041052 A1 * | 4/2010 | ......... | G06F 19/3456 |

OTHER PUBLICATIONS

Berger et al., "A comparative study of binding properties, dipeptidyl peptidase-4 (DPP-4) inhibitory activity and glucose-lowering efficacy of the DPP-4 inhibitors alogliptin, linagliptim, saxagliptin, sitagliptin and vildagliptin in mice", Endocrinology, Diabetes & Metabolism, vol. 1, No. 1, Nov. 24, 2017.

Ramkumar, S. et al., Acta Cardiol. Sin., 32(6):631-39 (2016).
Barias S. FDA Considers a New Paradigm For Over-the-Counter Medications: More Power—but More Burdens—for Pharmacists and Pharmacies. P T. May 2012;37(5):300-5. PubMed PMID: 22876088; PubMed Central PMCID: PMC3411219.
Crestor, Full Prescribing Information, 2012, AstraZeneca Pharmaceuticals LP.
Dyer O., "FDA Rejects sale of over the counter Statins", BMJ, Jan. 22, 2005; 330(7484):164.
May 9, 2013, power point presentations from the Engelberg Center for Health Care Reform.
Pfizer Wants Atorvastatin Available Over the Counter—Medscape—Aug. 4, 2011, downloaded from the Internet Nov. 30, 2018.
PR Newswire Association, "Americans Should Pay More Attention to Over-the-Counter (OTC) medicine Labels According to New Survey", Oct. 15, 2015 (citing McNeil Consumer Healthcare research).
Onglyza (saxagliptin) Tablets Prescribing Information, (Bristol-Myers Squibb Company) Jul. 2009, [online], [retrieved on Feb. 28, 2021], Retrieved from the Internet: <URL: https://www.accessdata.fda.gov/drugsatfda_docs/label/2009/022350lbl.pdf>.
Januvia (sitagliptin) Tablets Prescribing Information (Merck & Co., Inc.) Feb. 2018, [online], [retrieved on Feb. 28, 2021] Retrieved from the Internet: <URL: https://www.accessdata.fda.gov/drugsatfda_docs/label/2018/021995s042lbl.pdf >.
Tradjenta (linagliptin) Tablets Prescribing Information (Boehringer Ingelheim International GmbH), 2012, [online], [retrieved on Feb. 28, 2021] Retrieved from the Internet: <URL: https://www.accessdata.fda.gov/drugsatfda_docs/label/2012/201280s005lbl.pdf>.
Nesina (alogliptin) Tablets Prescribing Information (Takeda Pharmaceuticals America, Inc.) Dec. 2019, [online], [retrieved on Feb. 28, 2021] Retrieved from the Internet: <URL: https://www.accessdata.fda.gov/drugsatfda_docs/label/2016/022271s011lbl.pdf >.
Onglyza Tablet 2.5 mg and Onglyza Tablet 5 mg documents (including the package insert for the United States, the package insert for Europe) Pharmaceuticals and Medical Devices Agency, Mar. 25, 2013, <URL: https://www.pmda.go.jp/drugs/2013/P201300036/index.html.
"Trazebta" Tablets 5mg, Announcement of Revision of Package Insert, Nippon Boehringer Ingelheim Co., Ltd., Mar. 2013 (Japanese).
Trajenta Tablets 5mg, Announcement of Revision of Package Insert, Nippon Boehringer Ingelheim Co., Ltd., Mar. 2013 (English version of "Trazebta").

* cited by examiner

400

(402) A computer system for qualifying a human subject for over-the-counter delivery of a dipeptidyl peptidase-4 inhibitor pharmaceutical composition for lowering blood sugar. The computer system includes one or more processors and a memory, the memory includes non-transitory instructions which, when executed by the one or more processor, perform a method (403) The dipeptidyl peptidase-4 inhibitor pharmaceutical composition has the structure of structure (I)

(404) The dipeptidyl peptidase-4 inhibitor pharmaceutical composition includes saxagliptin or a pharmaceutically acceptable salt thereof (405) The dipeptidyl peptidase-4 inhibitor pharmaceutical composition is selected from the group consisting of sitagliptin, linagliptin, and alogliptin (406) The lowering blood sugar is to treat or prevent Type 2 diabetes (407) Conduct a first survey of the subject thereby obtaining a first plurality of survey results (408) The first plurality of survey results includes whether the subject is any one of (i) pregnant, (ii) breastfeeding, or (iii) planning to become pregnant, a Type 1 diabetes status of the subject, a ketoacidosis status of the subject, an age of the subject, a blood sugar level of the subject, whether the subject has ever had a pancreatic problem, an alcohol consumption status of the subject, whether the subject has ever had a gallstone, whether the subject has ever had high triglyceride levels, and whether the subject is taking a medication that interacts with the dipeptidyl peptidase-4 inhibitor pharmaceutical composition (409) The first plurality of survey results further includes whether the subject is allergic to the dipeptidyl peptidase-4 inhibitor pharmaceutical composition, and the first plurality of filters includes an adverse reaction filter that is fired when the first plurality of survey results indicates that the subject is allergic to the dipeptidyl peptidase-4 inhibitor pharmaceutical composition

Fig. 4A (407 continued)

(410) The first plurality of survey results further includes whether the subject has ever had heart failure, and the second plurality of filters includes a heart failure filter that is fired when the first plurality of survey results indicates that the subject has had heart failure (411) The symptom of heart failure, which is capable of firing the heart failure symptom filter, is selected from the group consisting of increased shortness of breath, trouble breathing, a rapid increase in weight, swelling of the feet, swelling of the ankles, and swelling of the legs (412) Run all or a portion of the first plurality of survey results against a first plurality of filters of a first category class. When a respective filter in the first plurality of filters is fired, the subject is deemed not qualified for delivery of the dipeptidyl peptidase-4 inhibitor pharmaceutical composition and the method is terminated without delivery of the dipeptidyl peptidase-4 inhibitor pharmaceutical composition to the subject (413) The first plurality of filters includes a first pregnancy filter that is fired at least when the first plurality of survey results indicates that the subject is pregnant or the subject is breastfeeding (414) The first pregnancy filter is also fired when the first plurality of survey results indicates that the subject plans to become pregnant within a predetermined period of time (415) The first plurality of filters includes a Type 1 diabetes filter that is fired at least when the first plurality of survey results indicates that the subject has Type 1 diabetes (416) The first plurality of filters includes a first ketoacidosis filter that is fired at least when the first plurality of survey results indicates that the subject has ketoacidosis

(417) The first plurality of filters includes an age filter (418) The age filter is also fired when the first plurality of survey results indicates that the subject is less than eighteen years old (419) The first plurality of filters includes a first blood sugar filter that is fired at least when the first plurality of survey results indicates that the subject has a blood sugar level that is either below a first baseline blood sugar level or above a ceiling blood sugar level (420) The first baseline blood sugar level used in the first blood sugar filter is 6.5% glycated hemoglobin (421) The ceiling blood sugar level used in the first blood sugar filter is 7.5% glycated hemoglobin (423) Run all or a portion of the first plurality of survey results against a second plurality of filters of a second category class. When a respective filter in the second plurality of filters is fired, the subject is provided with a warning corresponding to the respective filter (424) The warning corresponding to a respective filter in the second plurality of filters includes a prompt for the subject to indicate whether they have discussed the risk factor underlying the respective filter in the second plurality of filters that was fired with a health care professional. Acknowledgement is obtained from the subject when the subject indicates that they have discussed the risk factor underlying the respective filter in the second plurality of filters that was fired with a health care professional (425) The first plurality of filters includes a pancreatic disease filter that is fired at least when the first plurality of survey results indicates that the subject has pancreatitis

(426) The second plurality of filters includes an alcohol consumption filter (427) The alcohol consumption filter is also fired when the first plurality of survey results indicates that the subject, on average, consumes at least a predetermined number of alcoholic drinks over a predetermined period of time (428) The second plurality of filters includes a gallstone filter that is fired at least when the first plurality of survey results indicates that the subject has had a gallstone (429) The second plurality of filters includes a triglyceride filter that is fired when the first plurality of survey results indicates that the subject has a high triglyceride level (430) The second plurality of filters includes a first drug interaction filter that is fired when the first plurality of survey results indicates that the subject is taking a medication that interacts with the dipeptidyl peptidase-4 inhibitor pharmaceutical composition (431) The medication that interacts with the dipeptidyl peptidase-4 inhibitor pharmaceutical composition, which is capable of firing the first drug interaction filter, is selected from the group consisting of an HIV medication, an AIDS medication, an antifungal medication, an antibiotic, or a medication for diabetes (433) Obtain acknowledgment from the subject for the warning issued to the subject by any filter in the second plurality of filters (D)

Fig. 4D

(435) Proceed with a fulfillment process when no filter in the first plurality of filters has been fired and the subject has acknowledged each warning associated with each filter in the second plurality of filters that was fired (436) The fulfillment process includes storing an indication in a subject profile of an initial order for the dipeptidyl peptidase-4 inhibitor pharmaceutical composition, communicating an over the counter drug facts label for the dipeptidyl peptidase-4 inhibitor pharmaceutical composition to the subject, and authorizing, upon confirmation from the subject that the over the counter drug facts label has been received and read, provision of the dipeptidyl peptidase-4 inhibitor pharmaceutical composition to the subject (437) Upon confirmation from the subject that the over the counter drug facts label has been received and read, the subject is authorized for provision of a dosage of 2.5 mg per day of saxagliptin (438) The fulfillment process further includes storing a destination associated with the subject in the subject profile (439) The fulfillment process further includes coordinating shipping of the dipeptidyl peptidase-4 inhibitor pharmaceutical composition to a physical address associated with the subject (442) Responsive to receiving a re-order request from the subject for the dipeptidyl peptidase-4 inhibitor pharmaceutical composition, performing a re-fulfillment procedure

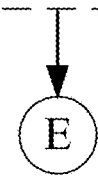

Fig. 4E

(443) Conduct a second survey of the subject thereby obtaining a second plurality of survey results (444) The second survey results comprise whether the subject is one of (i) pregnant, (ii) breastfeeding, or (iii) planning to become pregnant, whether the subject has experienced a symptom of ketoacidosis since receiving their last provision of the dipeptidyl peptidase-4 inhibitor pharmaceutical composition, whether the subject has experienced a skin problem since receiving their last provision of the dipeptidyl peptidase-4 inhibitor pharmaceutical composition, whether the subject has experienced stomach pain since receiving their last provision of the dipeptidyl peptidase-4 inhibitor pharmaceutical composition, whether the subject has experienced joint pain since receiving their last provision of the dipeptidyl peptidase-4 inhibitor pharmaceutical composition, whether the subject has experienced a symptom of hypoglycemia since receiving their last provision of the dipeptidyl peptidase-4 inhibitor pharmaceutical composition, whether the subject is experiencing a bodily stress, whether the subject is taking a medication that interacts with the dipeptidyl peptidase-4 inhibitor pharmaceutical composition, and if a predetermined period of time has passed since the user received a provision of the dipeptidyl peptidase 4 inhibitor blocker pharmaceutical composition, a blood sugar level of the subject (445) Run all or a portion of the second plurality of survey results against a third plurality of filters of the first category class. When a respective filter in the third plurality of filters is fired, the subject is deemed not qualified for the dipeptidyl peptidase-4 inhibitor pharmaceutical composition and the re-fulfillment process is terminated without delivery of the dipeptidyl peptidase-4 inhibitor pharmaceutical composition to the subject (446) The third plurality of filters includes a second pregnancy filter that is fired at least when the second plurality of survey results indicates that the subject is pregnant or the subject is breastfeeding (447) The second pregnancy filter is also fired when the first plurality of survey results indicates that the subject plans to become pregnant within a predetermined period of time

(448) The third plurality of filters includes a ketoacidosis symptom filter that is fired at least when the second plurality of survey results indicates that the subject has experienced symptoms of ketoacidosis since receiving their last provision of the dipeptidyl peptidase-4 inhibitor pharmaceutical composition (449) A symptom of ketoacidosis that is capable of firing the ketoacidosis symptom filter is selected from the group consisting of an increase of ketones in the blood of the subject, an increase of ketones in the urine of the subject, nausea, tiredness, vomiting, trouble breathing, and stomach pain including in the abdominal area (450) The third plurality of filters includes a skin problem filter that is fired at least when the second plurality of survey results indicates that the subject has experienced blistering or an exfoliative skin condition since receiving their last provision of the dipeptidyl peptidase-4 inhibitor pharmaceutical composition (451) The third plurality of filters includes a stomach pain filter that is fired at least when the second plurality of survey results indicates that the subject has experienced stomach pain since receiving their last provision of the dipeptidyl peptidase-4 inhibitor pharmaceutical composition (452) The third plurality of filters includes a joint pain filter that is fired at least when the second plurality of survey results indicates that the subject has experienced joint pain since receiving their last provision of the dipeptidyl peptidase-4 inhibitor pharmaceutical composition (453) The third plurality of filters includes a second blood sugar filter that is fired at least when (i) a predetermined period of time has passed since the user received a provision of the dipeptidyl peptidase-4 inhibitor pharmaceutical composition, and (ii) the second plurality of survey results indicates that the subject has a blood sugar level of at least a second baseline blood sugar level (454) The second baseline blood sugar level used in the second blood sugar filter is 7% glycated hemoglobin (G)

Fig. 4G

(456) Run all or a portion of the second plurality of survey results against a fourth plurality of filters of the second category class. When a respective filter in the fourth plurality of filters is fired, the subject is provided with a warning corresponding to the respective filter (457) The fourth plurality of filters includes a hypoglycemia symptom filter that is fired at least when the second plurality of survey results indicates that the subject has experienced symptoms of hypoglycemia since receiving their last provision of the dipeptidyl peptidase-4 inhibitor pharmaceutical composition (458) A symptom of hypoglycemia that is capable of firing the hypoglycemia symptom filter is selected from the group consisting of shaking, sweating, rapid heartbeat, change in vision, hunger, headaches, and a change in mood (459) The fourth plurality of filters includes a bodily stress filter that is fired at least when the second plurality of survey results indicates that the subject is experiencing a bodily stress (460) A bodily stress, which is capable of firing the bodily stress filter, is selected from the group consisting of fever, a recent trauma, an infection, or a recent surgery (461) The fourth plurality of filters includes a second drug interaction filter that is fired at least when the second plurality of survey results indicates that the subject is taking a medication that interacts with the dipeptidyl peptidase-4 inhibitor pharmaceutical composition (462) A medication that interacts with the dipeptidyl peptidase-4 inhibitor pharmaceutical composition, which is capable of firing the drug interaction filter, is selected from the group consisting of an HIV medication, an AIDS medication, an antifungal medication, an antibiotic, or a medication for diabetes

Fig. 4H

(464) Obtain acknowledgment from the subject for the warning issued to the subject by any filter in the fourth plurality of filters (466) Proceed with the re-fulfillment process when the re-fulfillment process is not already terminated by the firing of a filter in the third plurality of filters and the subject has acknowledged each warning associated with each filter in the fourth plurality of filters that was fired (467) The re-fulfillment process further includes storing an indication in the subject profile of a re-order for the dipeptidyl peptidase-4 inhibitor pharmaceutical composition, communicating the over the counter drug facts label for the dipeptidyl peptidase-4 inhibitor pharmaceutical composition to the subject, and authorizing, upon confirmation from the subject that the over the counter drug facts label has been received and read, a re-order provision of the dipeptidyl peptidase-4 inhibitor pharmaceutical composition to the subject 468 Perform a re-fulfillment procedure where the second plurality of survey results further includes whether the subject has experienced a side effect from the dipeptidyl peptidase-4 inhibitor pharmaceutical composition since receiving their last provision of the dipeptidyl peptidase-4 inhibitor pharmaceutical composition, and the fourth plurality of filters further includes a side effect filter that is fired at least when the second plurality of survey results indicates that the subject has experienced, since receiving their last provision of the dipeptidyl peptidase-4 inhibitor pharmaceutical composition, a side effect selected from the group consisting of an upper respiratory tract infection, a urinary tract infection, and headaches (469) Perform a re-fulfillment procedure where the second plurality of survey results further includes whether the subject has experienced a symptom of heart failure since receiving their last provision of the dipeptidyl peptidase-4 inhibitor pharmaceutical composition, and the third plurality of filters further includes a heart failure symptom filter that is fired at least when the second plurality of survey results indicates that the subject has experienced, since receiving their last provision of the dipeptidyl peptidase-4 inhibitor pharmaceutical composition, a symptom of heart failure.

Fig. 4I

Are you or do you plan to become pregnant? Are you breastfeeding or planning to breastfeed? ⸺ 502

Saxagliptin OTC should be used in pregnancy only if the potential benefits justifies the potential risk to the baby. Only a doctor can decide that. Do not breast-feed while taking Saxagliptin OTC. ⸺ 504

Thank you for visiting the site.

Are you taking an HIV medication, an AIDS medication, an antifungal medication, an antibiotic, or a medication for diabetes? — 506

— 508

HbA1c Level

Saxagliptin OTC may not be right for you. Based on your answers, it is important to talk to your doctor about potential risks of taking Saxagliptin OTC. It may be helpful to have your summary of answers when talking to your doctor.

Has your doctor said it is OK for you to take Saxagliptin OTC?

— 602

METHODS FOR LOWERING BLOOD SUGAR WITH A DIPEPTIDYL PEPTIDASE-4 INHIBITOR PHARMACEUTICAL COMPOSITION

CROSS REFERENCE TO RELATED APPLICATIONS

This application claims priority to U.S. Provisional Patent Application Ser. No. 62/685,206, filed Jun. 14, 2018, which is hereby incorporated by reference in its entirety.

TECHNICAL FIELD

The present disclosure relates generally to methods for lowering blood sugar, e.g., thereby, treating Type 2 diabetes and/or maintaining sub-diabetic blood sugar levels, by administering an over-the-counter dipeptidyl peptidase-4 inhibitor pharmaceutical composition to a subject in need thereof, who has been qualified for over-the-counter access to the composition.

BACKGROUND

Diabetes is a leading cause of death and increasing health care costs worldwide. NCD Risk Factor Collaboration, The Lancet, 387: 1513-1530 (2016). Since 1980, the number of people living with diabetes worldwide has nearly quadrupled. Id. As of 2015, according to the CDC, about 12% of all adults in the United States had diabetes and nearly 35% of all adults in the U.S. had prediabetes. Centers for Disease Control and Prevention, 'National Diabetes Statistics Report 2017' (2017). Further, nearly half of diabetes patients do not have their blood sugar under control. Polonsky et al., Patient Prefer. Adherence, 10:1299-1307 (2016). Moreover, diabetes poses a significant economical challenge. The American Diabetes Association estimated that in 2012, $245 billion was spent in direct and indirect medical expenses relating to diagnosed diabetes in the U.S. American Diabetes Association, Diabetes Care, 36(4): 1033-46 (2013).

Fortunately, diabetes (and specifically, type 2 diabetes) can be managed by, for example, using dipeptidyl peptidase-4 inhibitors, which are well established prescription pharmaceuticals used for lowering blood sugar, e.g., thereby, treating Type 2 diabetes and/or maintaining sub-diabetic blood sugar levels. For instance, the efficacy and safety of saxagliptin, which was first approved in the U.S. for the treatment of diabetes in 2009, has been demonstrated in at least 10 double-blind, placebo-controlled, randomized studies (e.g., as described in Jain, Adv Ther., 32(11): 1065-1084 (2015)). However, access to dipeptidyl peptidase-4 inhibitors is restricted by the requirement for a prescription. Unfortunately, long-term trends demonstrate many people avoid prescription medications, including dipeptidyl peptidase-4 inhibitors.

One approach to making dipeptidyl peptidase-4 inhibitors more accessible is to make them available without a prescription, e.g., over-the-counter ("OTC"). There are a variety of health benefits derived from switching a drug from prescription to OTC including, but not limited to, generating wider availably to therapies, providing a greater number of therapeutic approaches, providing direct and rapid access to treatments, providing patients with an active role in their own health care, and allowing patients to become self-reliant in preventing and relieving minor symptoms or conditions World Health Organization, "Guidelines for the Regulatory Assessment of Medicinal Products for use in Self-Medication," 2000. Given the large number of individuals with uncontrolled high blood sugar, providing access to OTC dipeptidyl peptidase-4 inhibitors could provide significant societal health benefits.

However, switching distribution of a pharmaceutical from prescription-only to OTC creates a significant risk that the patient population will be unable to appropriately self-select themselves for safe use of the pharmaceutical and then self-medicate using the drug in a responsible manner. The manifestations embodied within these concerns include incorrect self-diagnosis, incorrect drug-qualification, unrecognized drug-drug interactions (DDI), unanticipated adverse drug reactions and/or side-effects, improper dosing and/or administration, masking of a disease, addiction, inappropriate drug dependency, substance abuse, and patient delay in seeking necessary medical attention. Ruiz et al., Current Drug Safety, 5(4):315 (2010).

Because dipeptidyl peptidase-4 inhibitors cause adverse effects in certain patients, the population receiving the drug should be carefully selected and monitored. In order to ensure the safety of OTC distribution of dipeptidyl peptidase-4 inhibitor, prospective patients must effectively self-select themselves for the drug. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey," Oct. 15 (2015) (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Currently, there are two regulatory pathways for legal marketing of an OTC drug in the United States. In the first pathway, marketing occurs in compliance with an OTC drug monograph, that sets regulatory standards for non-prescription drugs that are not covered by human drug applications, e.g., a New Drug Application (NDA) or Abbreviated New Drug Application (ANDA). An OTC monograph is created as a result of a three phase OTC drug review by the FDA. In phase I of the review, an advisory review panel determines whether ingredients in the proposed OTC composition could be generally recognized as safe and effective for use in self-treatment. In the second pathway, marketing occurs under the authority of an approved product-specific new drug application (NDA), or an abbreviated new drug application (ANDA). In order to support an over-the-counter label for a drug for which regulatory approval is being sought through an NDA, a consumer research study is required to assess the consumer's ability to select and deselect themselves as appropriate users of the drug, based on the proposed labeling for the drug. Oliver, A., Regulatory Rapporteur, 10(3):4-9 (2013), which is incorporated by reference herein.

However, attempts at switching distribution of drugs having potentially far-reaching benefits for societal health, from prescription-only to an OTC model, have repeatedly failed, in large part due to concerns over inappropriate patient selection and medication. Possibly the best documented cases relate to statins used to treat high cholesterol. For instance, Merck has had at least three applications for sale of over-the-counter lovastatin rejected by the FDA, in 2000, 2005, and 2007. In 2005, their proposal to permit over-the-counter sales of lovastatin was rejected by an expert advisory panel at the FDA in 2005. The panel was concerned by a marketing study performed to support the proposal in which approximately one third of 3316 customers who were offered the drug over-the-counter decided they would purchase the drug. After reviewing the data, the panel concluded that 45% of the purchases would have been inappropriate for a variety of reasons, including the age of the subject, the subject's lack of knowledge about their condition, and contraindications associated with their condition. Dyer et al., BMJ, 330(7484): 164 (2005). In 2007, the board again concluded that the ability of consumers to appropriately self-select and to adequately comply with chronic MEVACOR® therapy without the intervention of a physician had not been demonstrated. Division of Metabolic and Endocrine Drug Products, 2005, "NDA 21-213 Nonprescription MEVACOR® 20 mg Joint Advisory Committee Meeting."

Similarly, Pfizer announced in 2011 its intention to switch LIPITOR® from prescription-only to OTC status. Sett OTC bulletin, 16 Nov. 2011, page 7. However, they abandoned their attempt in 2014 when a phase 3 "actual use" trial, intended to simulate the OTC use of LIPITOR® (atorvastatin calcium) 10 mg, failed to meet its primary objectives on the basis that patient compliance with the direction to check their low-density lipoprotein cholesterol (LDL-C) level and, after checking their LDL-C level, take appropriate action based on their test results was unsatisfactory. Pfizer Inc., "Pfizer Reports Second-Quarter 2015 Results," (2015).

In fact, in the nearly two decades since Bristol-Myers Squibb and Merck & Co first failed in their attempts to switch PRAVACHOL® and lovastatin, respectively, to OTC, a statin has never been granted OTC status in the United States. This is despite that nearly ⅙th of the adult population in the U.S. is eligible for cholesterol-lowering medications, under the current guidelines, but are not taking anything.

The information disclosed in this Background section is only for enhancement of understanding of the general background of the invention and should not be taken as an acknowledgment or any form of suggestion that this information forms the prior art already known to a person skilled in the art.

SUMMARY

Given the above background, what is needed in the art are systems and methods for qualifying a human subject for delivery of a dipeptidyl peptidase-4 inhibitor pharmaceutical composition over-the-counter for lowering blood sugar, e.g., thereby, treating Type 2 diabetes and/or maintaining sub-diabetic blood sugar levels.

The present disclosure addresses the need in the art for systems and methods configured for qualifying a human subject for over-the-counter delivery of a dipeptidyl peptidase-4 inhibitor pharmaceutical composition (e.g., saxagliptin) for lowering blood sugar levels, e.g., thereby, treating Type 2 diabetes and/or maintaining sub-diabetic blood sugar levels. In the present disclosure, systems and methods are provided for over-the-counter delivery of a dipeptidyl peptidase-4 inhibitor pharmaceutical composition to a subject. Survey results from the subject are run against a first plurality of filters. When a filter in the first plurality is fired, the subject is deemed not qualified for delivery of the dipeptidyl peptidase-4 inhibitor pharmaceutical composition. The survey results are also run against a second plurality of filters. When a respective filter in the second plurality is fired, the subject is provided with a corresponding warning. The method proceeds to a fulfillment process when no filter in the first plurality is fired and the subject has acknowledged each warning associated with each fired filter in the second plurality of filters. The fulfillment process stores the composition order, communicates a drug facts label for the dipeptidyl peptidase-4 inhibitor pharmaceutical composition to the subject, and authorizes, upon subject confirmation that the label has been read, provision of the dipeptidyl peptidase-4 inhibitor pharmaceutical composition to the subject.

Accordingly, one aspect of the present disclosure provides a method for qualifying a subject for over-the-counter delivery of a dipeptidyl peptidase-4 inhibitor pharmaceutical composition for lowering the blood sugar of the subject, e.g., thereby, treating Type 2 diabetes and/or maintaining sub-diabetic blood sugar levels. The method includes conducting a first survey of the subject in order to obtain a variety of survey results. In some embodiments, the survey results indicate one or more of: whether the subject is pregnant, breastfeeding, or planning to become pregnant, a Type 1 diabetes status of the subject, a ketoacidosis status of the subject, an age of the subject, a blood sugar level of the subject, whether the subject has a pancreatic problem, an alcohol consumption status of the subject, whether the subject has ever had a gallstone, whether the subject has ever had high triglycerides, and whether the subject is taking a medication that interacts with the dipeptidyl peptidase-4 inhibitor pharmaceutical composition.

The method also includes running all or a portion of the survey results against a first plurality of filters of a first category class. Filters in the first category class correspond to contraindications. When a respective filter in the first plurality of filters is fired, the subject is deemed not qualified for delivery of the dipeptidyl peptidase-4 inhibitor pharmaceutical composition. The method is terminated accordingly without delivery of the dipeptidyl peptidase-4 inhibitor pharmaceutical composition to the subject. In some embodiments, the first plurality of filters includes one or more of: a pregnancy filter, a Type 1 diabetes filter, a ketoacidosis filter, an age filter, and a blood sugar filter.

The method also includes running all or a portion of the survey results against a second plurality of filters of a second category class. Filters in the second category class correspond to risk factors. When a respective filter in the second plurality of filters is fired, the subject is provided with a warning corresponding to the respective filter. In some embodiments, the second plurality of filters includes one or more of: a pancreatic disease filter, an alcohol consumption filter, a gallstone filter, a triglyceride filter, and a drug interaction filter. However, unlike filters in the first plurality of filters, filters in the second plurality of filters do not automatically terminate the process without delivery of the dipeptidyl peptidase-4 inhibitor pharmaceutical composition to the subject.

The method continues by obtaining acknowledgment from the subject for the warning issued to the subject by any filter in the second plurality of filters. In some embodiments, acknowledgment from the subject is a written acknowledgement, a verbal acknowledgment, or an electronic acknowledgment such as an electronic signature.

The method continues by proceeding with a fulfillment process when no filter in the first plurality of filters has been fired and the subject has acknowledged each warning associated with each filter in the second plurality of filters that was fired.

In some embodiments, the fulfillment process includes storing an indication in a subject profile of an initial order for the dipeptidyl peptidase-4 inhibitor pharmaceutical composition, communicating an over-the-counter drug label for the dipeptidyl peptidase-4 inhibitor pharmaceutical composition, and authorizing, upon confirmation from the subject that the over-the-counter drug label has been received and read, provision of the dipeptidyl peptidase-4 inhibitor pharmaceutical composition to the subject.

In some embodiments, e.g., where the dipeptidyl peptidase-4 inhibitor pharmaceutical composition includes saxagliptin and/or alogliptin, the first plurality of survey results further includes whether the subject has ever had heart failure, and the second plurality of filters includes a heart failure filter.

In some embodiments, the dipeptidyl peptidase-4 inhibitor pharmaceutical composition has the structure of structure (I):

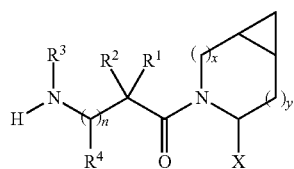

wherein x is 0 or 1 and y is 0 or 1, provided that:
x=1 when y=0 and
x=0 when y=1; and
wherein:
n is 0 or 1;
X is H or CN;
$R^1$, $R^2$, $R^3$ and $R^4$ are the same or different and are independently selected from hydrogen, alkyl, alkenyl, alkynyl, cycloalkyl, cycloalkylalkyl, bicycloalkyl, tricycloalkyl, alkylcycloalkyl, hydroxyalkyl, hydroxyalkylcycloalkyl, hydroxycycloalkyl, hydroxybicycloalkyl, hydroxytricycloalkyl, bicycloalkylalkyl, alkylthioalkyl, arylalkylthioalkyl, cycloalkenyl, aryl, aralkyl, heteroaryl, heteroarylalkyl, cycloheteroalkyl or cycloheteroalkylalkyl; all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfinyl, aminosulfonyl, alkylsulfinyl, sulfonamido or sulfonyl; and
$R^1$ and $R^3$ may optionally be taken together to form —$(CR^5R^6)_m$— where m is 2 to 6, and R and R are the same or different and are independently selected from hydroxy, alkoxy, H, alkyl, alkenyl, alkynyl, cycloalkyl, halo, amino, substituted amino, cycloalkylalkyl, cycloalkenyl, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or $R^1$ and $R^4$ may optionally be taken together to form —$(CR^7R^8)_p$— wherein p is 2 to 6, and $R^7$ and $R^8$ are the same or different and are independently selected from hydroxy, alkoxy, cyano, H, alkyl, alkenyl, alkynyl, cycloalkyl, cycloalkylalkyl, cycloalkenyl, halo, amino, substituted amino, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino;
or optionally $R^1$ and $R^3$ together with

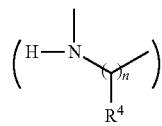

form a 5 to 7 membered ring containing a total of 2 to 4 heteroatoms selected from N, O, S, SO, or $SO_2$;
or optionally $R^1$ and $R^3$ together with

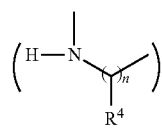

form a 4 to 8 membered cycloheteroalkyl ring wherein the cycloheteroalkyl ring has an optional aryl ring fused thereto or an optional 3 to 7 membered cycloalkyl ring fused thereto;
including all stereoisomers thereof;
and a pharmaceutically acceptable salt thereof, or a prodrug ester thereof, and all stereoisomers thereof.

In some embodiments, the dipeptidyl peptidase-4 inhibitor pharmaceutical composition includes saxagliptin or a pharmaceutically acceptable salt thereof. In some embodiments, the dipeptidyl peptidase-4 inhibitor pharmaceutical composition is selected from the group consisting of sitagliptin, linagliptin, and alogliptin.

In some embodiments, the warning corresponding to a respective filter in the second plurality of filters includes a prompt for the subject to indicate whether they have discussed the risk factor underlying the respective filter in the second plurality of filters that was fired with a heath care provider. Acknowledgement is obtained from the subject when the subject indicates that they have discussed the risk factor underlying the respective filter in the second plurality of filters that was fired with a health care provider.

In some embodiments, the fulfillment process further includes storing a destination associated with the subject in the subject profile.

In some embodiments, the fulfillment process further includes coordinating shipping of the dipeptidyl peptidase-4 inhibitor pharmaceutical composition to a physical address associated with the subject.

In one aspect, the present disclosure provides a method for qualifying a subject (e.g., a subject who was previously qualified to receive a provision of the dipeptidyl peptidase-4 inhibitor pharmaceutical composition) for a re-order of the dipeptidyl peptidase-4 inhibitor pharmaceutical composition (e.g., which is optionally performed in conjunction with a method for qualifying the subject for a first order of the dipeptidyl peptidase-4 inhibitor pharmaceutical composition). The method includes a re-fulfillment procedure. The re-fulfillment procedure includes conducting a second survey of the subject in order to obtain a second plurality of survey results. In some embodiments, the second survey results indicates one or more of: whether the subject is one of pregnant, breastfeeding, or planning to become pregnant, whether the subject has developed ketoacidosis since receiving their last provision of the dipeptidyl peptidase-4 inhibitor pharmaceutical composition, whether the subject has experienced a skin problem since receiving their last provision of the dipeptidyl peptidase-4 inhibitor pharmaceutical composition, whether the subject has experienced stomach pain since receiving their last provision of the dipeptidyl peptidase-4 inhibitor pharmaceutical composition, whether the subject has experienced joint pain since receiving their last provision of the dipeptidyl peptidase-4 inhibitor pharmaceutical composition, whether the subject has developed hypoglycemia since receiving their last provision of the dipeptidyl peptidase-4 inhibitor pharmaceutical composition, whether the subject is experiencing a bodily stress, whether the subject has started taking a medication that interacts with the dipeptidyl peptidase-4 inhibitor pharmaceutical composition since receiving their last provision of the dipeptidyl peptidase-4 inhibitor pharmaceutical composition, and if a threshold amount of time has passed since the subject received a provision of the dipeptidyl peptidase-4 inhibitor pharmaceutical, a blood sugar level of the subject.

The method also includes running all or a portion of the second plurality of survey results against a third plurality of filters of the first category class. Filters in the first category class correspond to contraindications. When a respective filter in the third plurality of filters is fired, the subject is deemed not qualified for the dipeptidyl peptidase-4 inhibitor pharmaceutical composition. Accordingly, the re-fulfillment process is terminated without delivery of the dipeptidyl peptidase-4 inhibitor pharmaceutical composition to the subject. In some embodiments, the third plurality of filters includes one or more of: a pregnancy filter, a ketoacidosis filter, a skin problem filter, a stomach pain filter, a joint pain filter, and a blood sugar filter.

The method also includes running all or a portion of the second plurality of survey results against a fourth plurality of filters of the second category class. Filters in the second category class correspond to risk factors. When a respective filter in the fourth plurality of filters is fired the subject is provided with a warning corresponding to the respective filter. In some embodiments, the fourth plurality of filters includes one or more of: a hypoglycemia filter, a bodily stress filter, and a drug interaction filter.

The method continues by obtaining acknowledgment from the subject for the warning issued to the subject by any filter in the fourth plurality of filters. When the re-fulfillment process is not already terminated by the firing of a filter in the third plurality of filters and the subject has acknowledged each warning associated with each filter in the fourth plurality of filters that was fired, the method continues with a re-fulfillment procedure.

In some embodiments, the re-fulfillment procedure includes storing an indication in the subject profile of a re-order for the dipeptidyl peptidase-4 inhibitor pharmaceutical composition, communicating an over-the-counter drug facts label for the dipeptidyl peptidase-4 inhibitor pharmaceutical composition to the subject, and authorizing, upon confirmation from the subject that the over-the-counter drug facts label has been received and read, a re-order provision of the dipeptidyl peptidase-4 inhibitor pharmaceutical composition to the subject.

In some embodiments, e.g., where the dipeptidyl peptidase-4 inhibitor pharmaceutical composition includes saxagliptin and/or alogliptin, the second plurality of survey results further indicates whether the subject has developed heart failure since receiving their last provision of the dipeptidyl peptidase-4 inhibitor pharmaceutical composition. The third plurality of filters further includes a heart failure filter.

In some embodiments, the lowering of blood sugar is to treat Type 2 diabetes and/or maintain sub-diabetic blood sugar levels.

BRIEF DESCRIPTION OF THE DRAWINGS

FIGS. 4A, 4B, 4C, 4D, 4E, 4F, 4G, 4H, and 4I collectively provide a flow chart of processes for qualifying a human subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, where elements in dashed boxes are optional, in accordance with various embodiments of the present disclosure.

Figure 1:
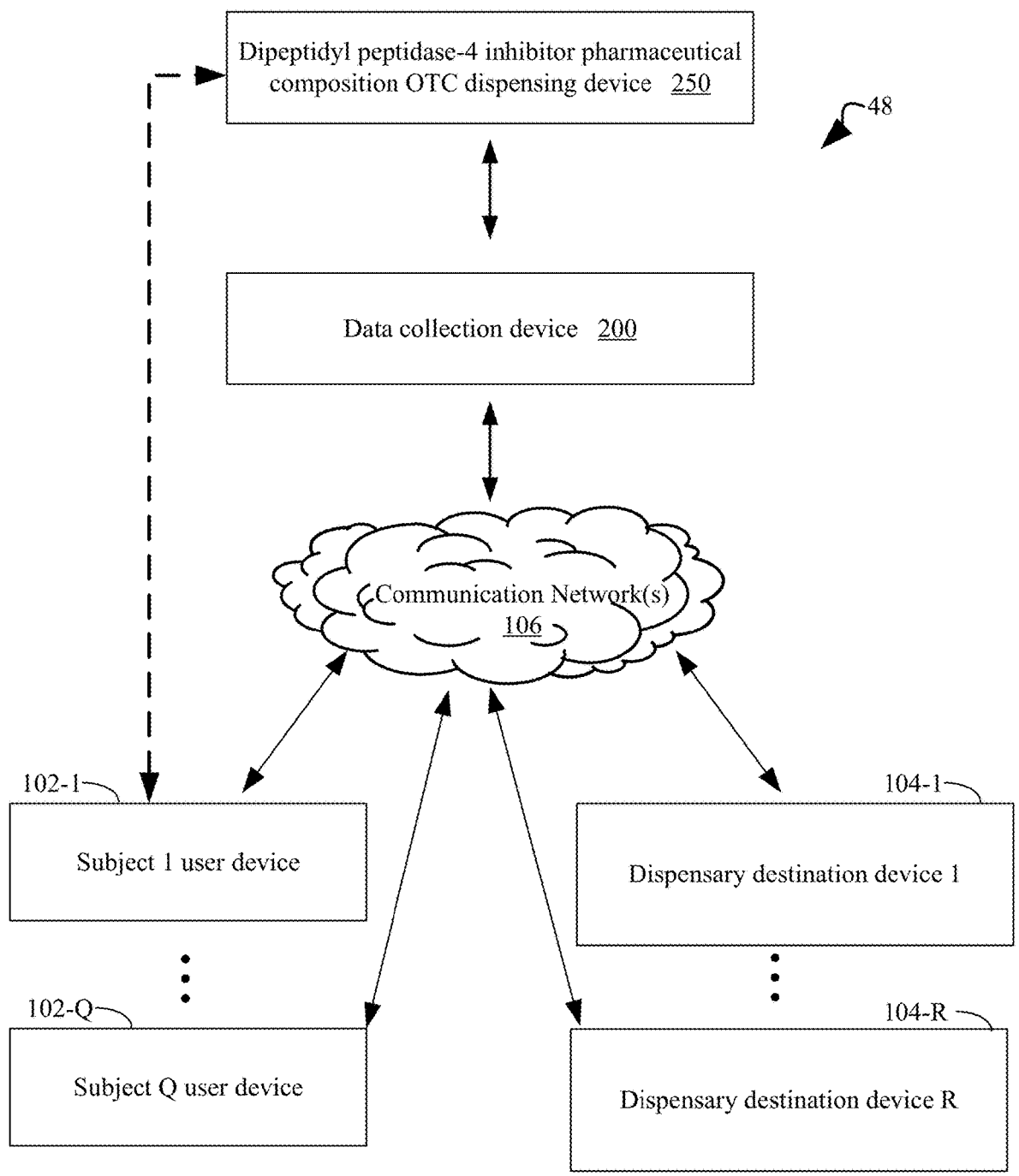
FIG. 1 illustrates an exemplary system topology that includes a dipeptidyl peptidase-4 inhibitor pharmaceutical composition over-the-counter (OTC) dispensing device for qualifying a human subject for over-the-counter delivery of a dipeptidyl peptidase-4 inhibitor pharmaceutical composition for lowering blood sugar (e.g., thereby, treating Type 2 diabetes and/or maintaining sub-diabetic blood sugar levels), a data collection device for collecting subject data, one or more user devices associated with human subjects, and one or more dispensary destination devices for distributing the dipeptidyl peptidase-4 inhibitor pharmaceutical composition over-the-counter, where the above-identified components are interconnected, optionally through a communications network, in accordance with an embodiment of the present disclosure.

In the figures, reference numbers refer to the same or equivalent parts of the present invention throughout the several figures of the drawing.

DETAILED DESCRIPTION

Diabetes is a growing health problem, in the United States and worldwide. Although diabetes can be effectively treated and/or prevented using established pharmaceutical compositions, access to these drugs is hindered by to the requirement for a prescription, as many individuals do not have adequate access and/or avoid the healthcare system for a variety of reasons. Accordingly, many people are not managing their diabetes or prediabetes conditions appropriately. While over-the-counter alternatives to these prescription pharmaceuticals would increase access to these compositions, thereby improving population management of diabetes and prediabetes around the world, patients often have difficulty self-selecting themselves for an appropriate over-the-counter medication. Because inappropriate use of these drugs can result in ineffective treatment and/or serious side-effects, better methods for selecting for, and treating patients with, other-the-counter diabetes medications are needed. The present disclosure provides, among other aspects, methods, systems, and computer readable media that solve these problems.

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over-the-counter" means to provide by retail purchase, subject to the constraints disclosed herein, but without a prescription or license from a physician or medical practitioner.

As used herein, the term "pharmaceutical compound" refers to any physical state of a material. Pharmaceutical compounds include capsules, tablets, liquids, topical formulations, and inhaled formulations.

As used herein, the term "contraindication" refers to a condition that makes a treatment, e.g., over-the-counter use of a dipeptidyl peptidase-4 inhibitor pharmaceutical composition, inadvisable. Contraindications include physical characteristics of a subject, e.g., pregnancy or kidney disease, and contemporaneous drug use, e.g., dipeptidyl peptidase-4 inhibitor pharmaceutical composition use. In the present context, identification of a contraindication fires a filter of a first category class, which prevents authorizing provision of a dipeptidyl peptidase-4 inhibitor pharmaceutical composition, in accordance with some implementations of the methods, systems, and software disclosed herein.

As used herein, the term "risk factor" refers to a condition that makes a treatment, e.g., over-the-counter use of a dipeptidyl peptidase-4 inhibitor pharmaceutical composition, possibly inadvisable. Risk factors include physical characteristics of a subject, e.g., a blood sugar reading, and contemporaneous drug use, e.g., use of a diabetes medication. In the present context, identification of a risk factor fires a filter of a second category class, which prevents authorizing provision of a dipeptidyl peptidase-4 inhibitor pharmaceutical composition without confirmation that the subject has discussed the risk factor with a medical professional, in accordance with some implementations of the methods, systems, and software disclosed herein.

As used herein, "drug interactions," e.g., with a dipeptidyl peptidase-4 inhibitor, include pharmacokinetic drug interactions and pharmacodynamics drug interactions. Generally, a pharmacokinetic drug interaction is an interaction between two drugs (e.g., a dipeptidyl peptidase-4 inhibitor and a second drug) that result in alterations in the absorption, transport, distribution, metabolism, and/or excretion of either drug. Generally, a pharmacokinetic drug interaction is an interaction between two drugs (e.g., a dipeptidyl peptidase-4 inhibitor and a second drug) that result in a direct change in the effect or either drug. For a more comprehensive summary of pharmacokinetic drug interactions and pharmacodynamics drug interactions, see, Cascorbi, I, Dtsch Arztebl Int., 109(33-34):546-55 (2012), the content of which is hereby incorporated by reference.

In the context of the present disclosure, classification of a condition as either a contraindication or a risk factor is specific to a particular identity and dose of a dipeptidyl peptidase-4 inhibitor pharmaceutical composition being authorized for over-the-counter use. Classification of a particular condition, e.g., contemporaneous dipeptidyl peptidase-4 inhibitor pharmaceutical composition use, may vary between different dipeptidyl peptidase-4 inhibitor pharmaceutical compositions (e.g., it may be classified as a contraindication for a first dipeptidyl peptidase-4 inhibitor, a risk factor for a second dipeptidyl peptidase-4 inhibitor, and/or neither for a third dipeptidyl peptidase-4 inhibitor). Likewise, a particular condition may be classified as a contraindication for use of a particular dipeptidyl peptidase-4 inhibitor at a first over-the-counter dosage, classified as a risk factor for the same particular dipeptidyl peptidase-4 inhibitor at a second (e.g., lower) over-the-counter dosage, and/or classified as neither for the same particular dipeptidyl peptidase-4 inhibitor at a third (e.g., lowest) over-the-counter dosage.

As used herein, whether a subject "has developed" a condition since receiving their last provision of a dipeptidyl peptidase-4 inhibitor refers to both conditions that are new to the subject, i.e., a condition that the subject did not have at the time they received their last provision of the dipeptidyl peptidase-4 inhibitor, and conditions that have been newly diagnosed, regardless of whether the condition existed when the subject received their last provision of the dipeptidyl peptidase-4 inhibitor, i.e., a condition that the subject was not aware of when they received their last provision of the dipeptidyl peptidase-4 inhibitor.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (e.g. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "bicycloalkyl," "tricycloalkyl," "cycloalkyl," and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$) alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy) propyl, and the like).

Each of the above terms (e.g., "alkyl," "heteroalkyl," "aryl, and "heteroaryl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", NR C(NR'R")=NR''', —S(O)R', —S(O)$_2$R', —S(O)$_2$NR'R", NRSO$_2$R', —CN and —NO₂ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like). These terms encompass groups considered exemplary "alkyl group substituents," which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —CO₂R', —CONR'R", —OC(O)NR'R", —NR"C(O)R', NR'C(O)NR"R''', —NR"C(O)₂R', NR—C(NR'R"R''')=NR'''', NR C(NR'R")=NR', —S(O)R', —S(O)₂R', —S(O)2NR'R", NRSO2R', —CN and —NO₂, —R', —N₃, —CH(Ph)₂, fluoro(C₁-C₄)alkoxy, and fluoro (C₁-C₄)alkyl, in a number ranging from zero to the total number of open valences on the aromatic ring system. Each of the above-named groups is attached to the heteroarene or heteroaryl nucleus directly or through a heteroatom (e.g., P, N, O, S, Si, or B); and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

As used herein, the term "heteroatom" includes oxygen (O), nitrogen (N), sulfur (S) and silicon (Si), boron (B) and phosphorous (P).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

In one aspect of the present disclosure a survey of a subject is conducted to obtain survey results, in order to determine if the subject qualifies for an over-the-counter (OTC) dipeptidyl peptidase-4 inhibitor pharmaceutical composition for lowering blood sugar, e.g., thereby, treating Type 2 diabetes and/or maintaining sub-diabetic blood sugar levels. The survey results are used as the basis for running filters of a first category class. If the triggering conditions of any of the filters in the first category class are fired, the subject does not qualify for the OTC dipeptidyl peptidase-4 inhibitor pharmaceutical composition. The survey results are also used as the basis for running filters of a second category class. If the triggering conditions of any of the filters in the second category class are fired, the subject is provided with warning messages associated with the respective filters of the second category class that have been fired. If none of the filters in the first category class are fired and the subject successfully addresses the warning messages associated with the respective filters of the second category class that have been fired a fulfillment process is initiated for OTC delivery of the dipeptidyl peptidase-4 inhibitor pharmaceutical composition.

FIG. 1 illustrates an example of an integrated system 48 for conducting one or more surveys of subjects in order to qualifying the subjects for OTC delivery of a dipeptidyl peptidase-4 inhibitor pharmaceutical composition. The integrated system 48 includes one or more connected user devices 102. The user devices 102 are configured for entering survey data and making requests for the dipeptidyl peptidase-4 inhibitor pharmaceutical composition. The system 48 also includes one or more dispensary destination devices 104 that are configured to receive instructions in order to provide the dipeptidyl peptidase-4 inhibitor pharmaceutical composition to qualifying subjects. Furthermore, the system 48 includes a dipeptidyl peptidase-4 inhibitor pharmaceutical composition over-the-counter (OTC) dispensing device 250 and one or more data collection devices 200 that are configured for collecting subject data.

Throughout the present disclosure, the data collection device 200 and the dipeptidyl peptidase-4 inhibitor pharmaceutical composition OTC dispensing device 250 will be referenced as separate devices solely for purposes of clarity. That is, the disclosed functionality of the data collection device 200 and the disclosed functionality of the dipeptidyl peptidase-4 inhibitor pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the dipeptidyl peptidase-4 inhibitor pharmaceutical composition OTC dispensing device 250 are contained in a single device.

With the integrated system 48, survey results from the subjects are run against a first plurality of filters (e.g., filter 216-1, filter 216-2, filter 216-4, etc.) When a filter in the first plurality of filters (e.g., filter 216) is fired for a respective subject, the respective subject is deemed not qualified for the dipeptidyl peptidase-4 inhibitor pharmaceutical composition. The survey results are also run against a second plurality of filters (e.g., filter 222-1, filter 222-2, filter 222-6, etc.) When a respective filter in the second plurality is fired for a respective subject, the respective subject is provided with a warning (e.g., filter warning 226) associated with the respective filter. In some embodiments the survey results are run against the first plurality of filters and the second plurality of filters concurrently. In some embodiments the survey results are run against the first plurality of filters and then against the second plurality of filters. The method enabled by the integrated system 48 proceeds to a fulfillment process when no filter in the first plurality fires and the subject has acknowledged, or otherwise successfully addressed, each warning associated with each filter in the second plurality of filters that fired. As part of the fulfillment process, the composition order is stored (e.g., in a subject profile 232 associated with the subject to receive the drug), a drug facts label (e.g., over-the-counter drug facts label 230) for the dipeptidyl peptidase-4 inhibitor is communicated to the qualifying subject. Upon subject confirmation that the label has been read, authorization is granted to dispense the dipeptidyl peptidase-4 inhibitor.

Referring to FIG. 1, the dipeptidyl peptidase-4 inhibitor pharmaceutical composition OTC dispensing device 250 qualifies a subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels. To accomplish this, the data collection device 200, which is in electrical communication with the dipeptidyl peptidase-4 inhibitor pharmaceutical composition OTC dispensing device 250, receives survey results originating from one or more user devices 102 associated with corresponding subjects. In some embodiments, the data collection device 200 receives such survey results directly from the user devices 102. For instance, in some embodiments the data collection device 200 receives this data wirelessly through radio-frequency signals. In some embodiments, such signals are in accordance with an 802.11 (Wi-Fi), Bluetooth, or ZigBee standard. In some embodiments, the data collection device 200 receives such data directly, analyzes the data, and passes the analyzed data to the dipeptidyl peptidase-4 inhibitor pharmaceutical composition OTC dispensing device 250.

In some embodiments, the data collection device 200 and/or the dipeptidyl peptidase-4 inhibitor pharmaceutical composition OTC dispensing device 250 is not proximate to the subject and/or does not have wireless capabilities or such wireless capabilities are not used for the purpose of acquiring survey results. In such embodiments, a communication network 106 may be used to survey questions (e.g., survey questions 208, 212) from the dipeptidyl peptidase-4 inhibitor pharmaceutical composition OTC dispensing device 250 to user devices 102 and the answers to such survey questions from the user devices 102 to the data collection device 200 and/or the dipeptidyl peptidase-4 inhibitor pharmaceutical composition OTC dispensing device 250. Further, in some embodiments the communication network 106 is used to communicate authorization to dispense the dipeptidyl peptidase-4 inhibitor survey questions from the dipeptidyl peptidase-4 inhibitor pharmaceutical composition OTC dispensing device 250 to dispensary destination devices 104.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the dipeptidyl peptidase-4 inhibitor pharmaceutical composition OTC dispensing device 250. Further, the data collection device 200 and/or the dipeptidyl peptidase-4 inhibitor pharmaceutical composition OTC dispensing device 250 may constitute a portable electronic device, a server computer, or in fact constitute several computers that are linked together in a network, be a virtual machine in a cloud computing context, be a container in a cloud computer context, or a combination thereof. As such, the exemplary topology shown in FIG. 1 merely serves to describe the features of an embodiment of the present disclosure in a manner that will be readily understood to one of skill in the art.

Figure 2:
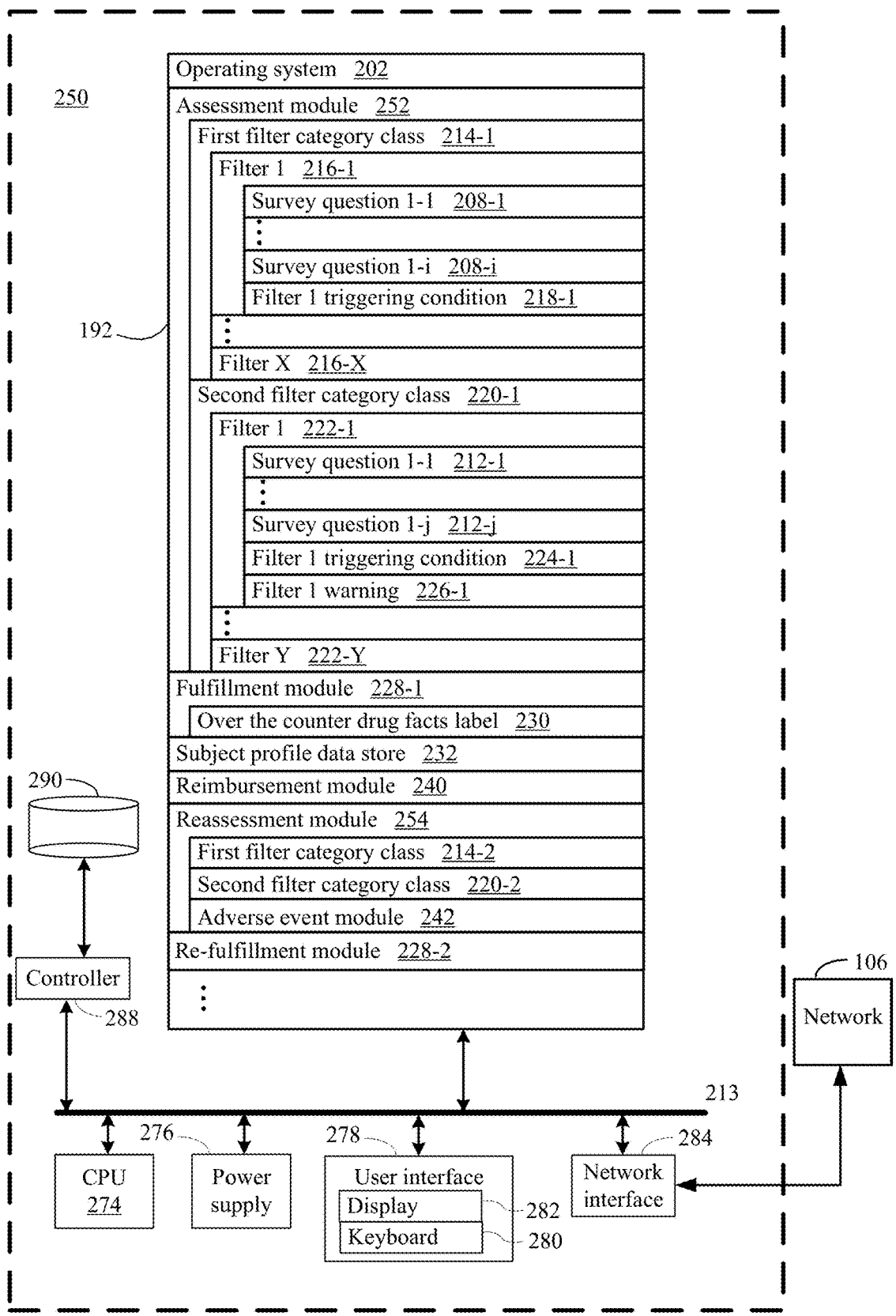
FIG. 2 illustrates an example device for qualifying a human subject for delivery of a dipeptidyl peptidase-4 inhibitor pharmaceutical composition over-the-counter for lowering blood sugar, e.g., thereby, treating Type 2 diabetes and/or maintaining sub-diabetic blood sugar levels, in accordance with various embodiments of the present disclosure.

Turning to FIG. 2 with the foregoing in mind, an exemplary dipeptidyl peptidase-4 inhibitor pharmaceutical composition OTC dispensing device 250 configured for determining whether a subject is qualified for OTC delivery of a dipeptidyl peptidase-4 inhibitor is depicted. Referring to FIG. 2, in typical embodiments, the dipeptidyl peptidase-4 inhibitor pharmaceutical composition OTC dispensing device 250 includes one or more computers. For purposes of illustration in FIG. 2, the dipeptidyl peptidase-4 inhibitor pharmaceutical composition OTC dispensing device 250 is represented as a single computer that includes all of the functionality for qualifying a human subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels. However, the present disclosure is not limited thereto. In some embodiments, the functionality for qualifying a human subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, is spread across any number of networked computers and/or resides on each of several networked computers, is hosted on one or more virtual machines at a remote location accessible across the communications network 106, and/or is hosted on one or more containers at a remote location accessible across the communications network 106. One of skill in the art will appreciate that any of a wide array of different computer topologies are used for the application and all such topologies are within the scope of the present disclosure.

The dipeptidyl peptidase-4 inhibitor pharmaceutical composition OTC dispensing device 250 of FIG. 2 is configured to conduct a first survey (e.g., using assessment module 252 to perform an initial qualification of the subject for provision of a the dipeptidyl peptidase-4 inhibitor pharmaceutical composition) and/or a second survey (e.g., using reassessment module 254 to perform a re-qualification of the subject for provision of a the dipeptidyl peptidase-4 inhibitor pharmaceutical composition). The first survey (e.g., the assessment) includes a variety of survey questions 208-1, 212-1 associated with filters 216, 222 within a plurality of filters of the first filter category class 214-1 and a plurality of filters in the second filter category class 220-1, respectively. Answers to the questions in the first survey received by the device are run against filters of a first category class 214-1, and filters of a second category class 220-1 within the first and second pluralities of filters 214-1, 216-1, respectively. Similarly, the second survey (e.g., the re-assessment) also includes a variety of questions associated with filters 216, 222 within a plurality of filters of a first category class 214-2 and a plurality of filters of a second category class 220-2, respectively. Answers to the questions in the second survey received by the device are run against filters of a first category class 216-2 and filters of a second category class 220-2, e.g., within the first and second pluralities of filters, respectively. Filters 216 of the first filter category class 214 are configured to terminate the qualification process when fired. Filters 222 of the second filter category class 220 are configured to provide the subject with a warning associated with a corresponding survey question. In other words, the device of FIG. 2 is configured to accumulate results from a survey (e.g., survey questions 208 and survey questions 212) and run the results against corresponding filters (e.g., filters 216 and filters 222, respectively) in order to determine if a subject is qualified for OTC delivery of a dipeptidyl peptidase-4 inhibitor pharmaceutical composition.

In the present disclosure, a plurality of filters refers to a series, or set, or filters in either the first filter category class or the second category class. For instance, in some embodiments, a plurality of filters of the first filter category class 214 can include any subset of filters 216 of the first filter category class. As an example, in some embodiments a plurality of filters of the first category class includes filters 216-1, 216-2, 216-3, . . . , 216-i, or any combination thereof.

Similarly, a plurality of filters of the second filter category class 220 can include any set of filters 222 of the second filter category class. Moreover, in some embodiments a plurality of filters of the second category class includes filters 222-1, 222-2, 222-3, . . . , 222-i, or any combination thereof.

Continuing to refer to FIG. 2, in some embodiments, the dispensing device 250 includes one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the dipeptidyl peptidase-4 inhibitor pharmaceutical composition OTC dispensing device 250 but that can be electronically accessed by the dipeptidyl peptidase-4 inhibitor pharmaceutical composition OTC dispensing device 250 over an Internet, intranet, or other form of network or electronic cable (illustrated as element 106 in FIG. 2) using network interface 284.

In some embodiments, the memory 192 of the dipeptidyl peptidase-4 inhibitor pharmaceutical composition OTC dispensing device 250 stores one or more of:

an operating system 202 that includes procedures for handling various basic system services;

an assessment module 252 for qualifying a subject for an initial over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, by communicating survey questions, obtaining results therefrom, and applying the results to qualifying filters, the assessment module including:

a first filter category class 214-1, including filters 216 (e.g., a first plurality of filters), each respective filter 216 in the first filter category class 214-1 associated with one or more survey questions 208 and one or more triggering conditions 218;

a second filter category class 220-1, including filters 222 (e.g., a second plurality of filters), each respective filter 222 in the second filter category class 220-1 associated with one or more survey questions 212, triggering conditions 224, and warnings 226;

a fulfillment module 228-1 for executing a fulfillment process when no filter 216 in the first filter category class 214-1 has been fired for a subject and the subject has acknowledged each warning 226 associated with each filter 222 in the second filter category class 220-1 that was fired as a result of answers by the subject to the survey questions 212, where the fulfillment process includes communicating an over-the-counter drug facts label 230 for the dipeptidyl peptidase-4 inhibitor pharmaceutical composition to the subject and receiving confirmation from the subject that the over-the-counter drug facts label has been received and read;

a reassessment module 254 for qualifying a subject for a subsequent over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, by communicating survey questions, obtaining results therefrom, and applying the results to qualifying filters, the assessment module including:
  a first filter category class 214-2, including filters 216 (e.g., a third plurality of filters), each respective filter 216 in the first filter category class 214-2 associated with one or more survey questions 208 and one or more triggering conditions 218;
  a second filter category class 220-2, including filters 222 (e.g., a second plurality of filters), each respective filter 222 in the second filter category class 220-2 associated with one or more survey questions 212, triggering conditions 224, and warnings 226;
a re-fulfillment module 228-2 for executing a re-fulfillment process when no filter 216 in the first filter category class 214-2 has been fired for a subject and the subject has acknowledged each warning 226 associated with each filter 222 in the second filter category class 220-2 that was fired as a result of answers by the subject to the survey questions 212, where the fulfillment process includes communicating an over-the-counter drug facts label 230 for the dipeptidyl peptidase-4 inhibitor pharmaceutical composition to the subject and receiving confirmation from the subject that the over-the-counter drug facts label has been received and read;
a subject profile data store 232 comprising a subject profile 232 for each of a plurality of subjects, each respective subject profile 232 including information (e.g., shipping information, billing information, biometric information, etc.) about a corresponding subject in the plurality of subjects, an initial order date and destination 236, and any re-order date and the destination 238 for the dipeptidyl peptidase-4 inhibitor pharmaceutical composition made by the corresponding subject using the dipeptidyl peptidase-4 inhibitor pharmaceutical composition OTC dispensing device 250;
an adverse event module 242 for identifying and aggregating records of adverse events associated with a plurality of subjects, e.g., corresponding to the firing of a filter 216 in the first filter category class 214-2 during a re-fulfillment process;
a reimbursement module 240 for determining eligibility and/or communicating an insurance claim associated with dipeptidyl peptidase-4 inhibitor, e.g., based on insurance information stored in a respective subject profile 232.

In some embodiments, the assessment module 252, reassessment module 254, and/or fulfillment module 228 are accessible within any browser (e.g., phone, tablet, laptop/desktop, or smartwatch). In some embodiments the assessment module 252, reassessment module 254, and/or fulfillment module 228 run on native device frameworks, and are available for download onto a user device 102 running an operating system 202 such as Android, iOS, or WINDOWS.

In some implementations, one or more of the above identified data elements or modules (e.g., assessment module 252, fulfillment module 228-1, etc.) of the dipeptidyl peptidase-4 inhibitor pharmaceutical composition OTC dispensing device 250 for qualifying a human subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a dipeptidyl peptidase-4 inhibitor pharmaceutical composition OTC dispensing device 250 for qualifying a human subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, is a smart phone (e.g., an iPhone, Blackberry, etc.), a laptop, a tablet computer, a desktop computer, a smart watch, or another form of electronic device (e.g., a gaming console). In some embodiments, the dipeptidyl peptidase-4 inhibitor pharmaceutical composition OTC dispensing device 250 is not mobile. In some embodiments, the dipeptidyl peptidase-4 inhibitor pharmaceutical composition OTC dispensing device 250 is mobile.

In some embodiments, the dipeptidyl peptidase-4 inhibitor pharmaceutical composition OTC dispensing device 250 is not a smart phone but rather is a tablet computer, desktop computer, emergency vehicle computer, or other form or wired or wireless networked device. In the interest of brevity and clarity, only a few of the possible components of the dipeptidyl peptidase-4 inhibitor pharmaceutical composition OTC dispensing device 250 are shown in FIG. 2 in order to better emphasize the additional software modules that are installed on the dipeptidyl peptidase-4 inhibitor pharmaceutical composition OTC dispensing device 250.

Figure 3:
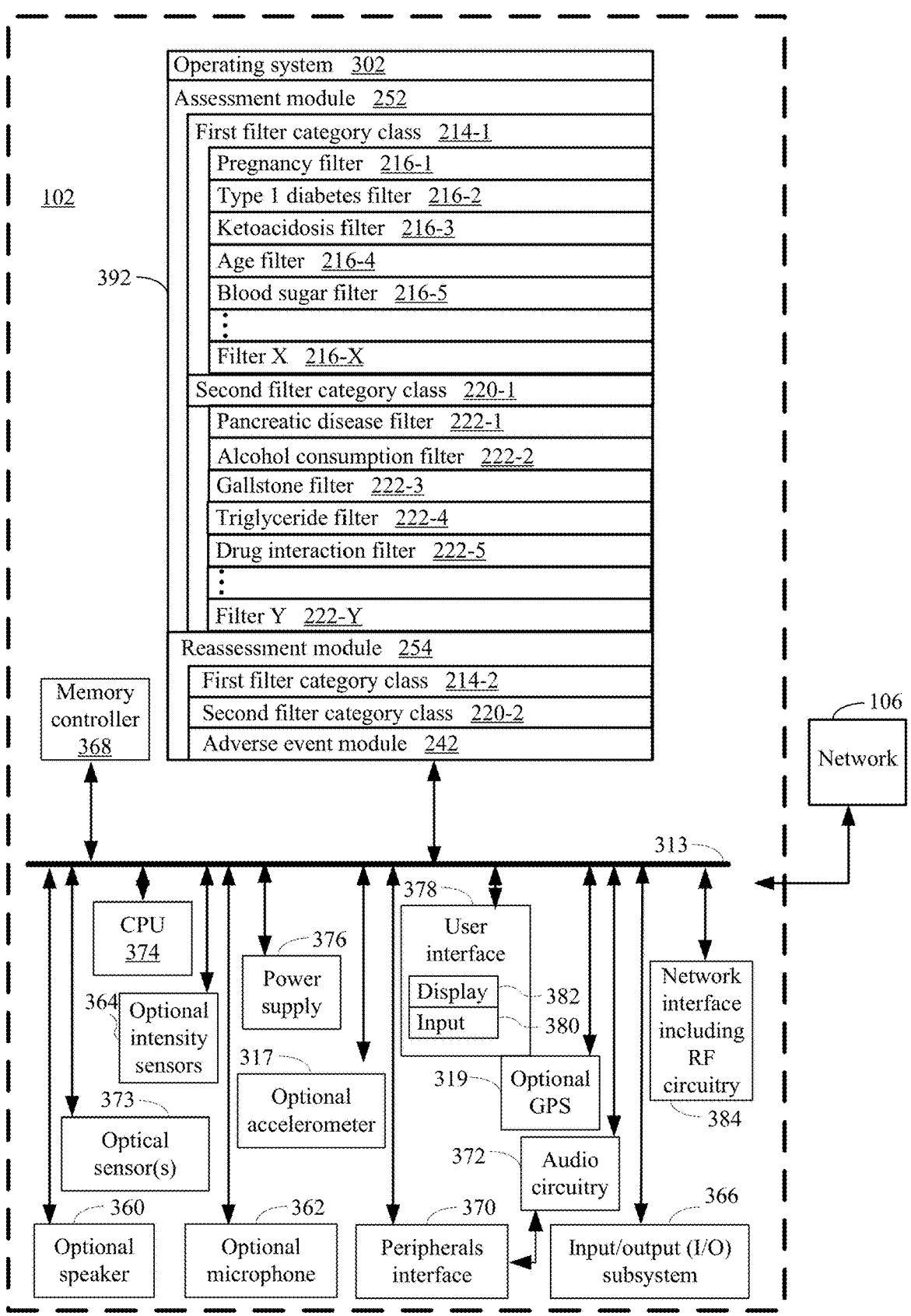
FIG. 3 illustrates an example device associated with a human subject for qualifying the human subject for over-the-counter delivery of a dipeptidyl peptidase-4 inhibitor pharmaceutical composition for lowering blood sugar, in accordance with an embodiment of the present disclosure, where it will be appreciated that the example device of FIG. 3 works in conjunction with the device of FIG. 2 to perform the methods illustrated in FIGS. 4 through 8 in some embodiments by, for instance providing the device of FIG. 2 with survey results and/or the results of firing filters of the present disclosure against such survey results but that, in alternative embodiments, the device of FIG. 2 performs all the methods of the present disclosure and the device of FIG. 3 is not used. In still further alternative embodiments, the device of FIG. 3 performs the methods of the present disclosure and the device of FIG. 2 is not used.

FIG. 3 provides a description of a user device 102 that can be used with the present disclosure. The user device 102 illustrated in FIG. 3 has one or more processing units (CPU's) 374, peripherals interface 370, memory controller 368, a network or other communications interface 384, a memory 392 (e.g., random access memory), a user interface 378, the user interface 378 including a display 382 and input 380 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 382 of the user device 102), an optional input/output (I/O) subsystem 366, one or more optional optical sensors 373, one or more communication busses 313 for interconnecting the aforementioned components, and a power supply 376 for powering the aforementioned components.

In some embodiments, the input 380 is a touch-sensitive display, such as a touch-sensitive surface. In some embodiments, the user interface 378 includes one or more soft keyboard embodiments. The soft keyboard embodiments may include standard (e.g., QWERTY) and/or non-standard configurations of symbols on the displayed icons.

The user device 102 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the user device 102 and/or for determining an amount of physical exertion by the subject.

It should be appreciated that the user device 102 illustrated in FIG. 3 is only one example of a multifunction device that may be used for performing a survey (e.g., first survey 206) in order to qualify for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, and that the user device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 392 of the user device 102 illustrated in FIG. 3 optionally includes high-speed random access memory and optionally also includes non-volatile memory, such as one or more magnetic disk storage devices, flash memory devices, or other non-volatile solid-state memory devices. Access to memory 392 by other components of the dipeptidyl peptidase-4 inhibitor pharmaceutical composition OTC dispensing device 250, such as CPU(s) 374 is, optionally, controlled by the memory controller 368. In some embodiments, the memory 392 of the user device 102 illustrated in FIG. 3 optionally includes:
  an operating system 302 that includes procedures for handling various basic system services;
  the assessment module 252 described above in conjunction with the dipeptidyl peptidase-4 inhibitor pharmaceutical composition OTC dispensing device 250;
  the first category class 214 described above in conjunction with the dipeptidyl peptidase-4 inhibitor pharmaceutical composition OTC dispensing device 250 further comprising a first pregnancy filter 216-1, a Type 1 diabetes filter 216-2, a ketoacidosis filter 216-3, an age filter 216-4, and a first blood sugar filter 216-5; and
  the second category class 220 described above in conjunction with the dipeptidyl peptidase-4 inhibitor pharmaceutical composition OTC dispensing device 250 comprising a pancreatic disease filter 222-1, an alcohol consumption filter 222-2, a gallstone filter 222-3, a triglyceride filter 222-4, and a first drug interaction filter 222-5;

In some embodiments, the optional accelerometer 317, optional GPS 319, and/or magnetometer (not shown) of the user device 102 or such components are used to recommend to qualifying subjects one or more suitable destinations for delivery of the dipeptidyl peptidase-4 inhibitor pharmaceutical composition over-the-counter. In some embodiments, the GPS 319 is used to determine if a subject is geographically restricted for OTC delivery of the dipeptidyl peptidase-4 inhibitor pharmaceutical composition. Geographical restrictions include a subject residing outside of delivery or shipping regions, marketing restrictions, and/or government regulations.

The peripherals interface 370 can be used to couple input and output peripherals of the device to CPU(s) 374 and memory 392. The one or more processors 374 run or execute various software programs and/or sets of instructions stored in memory 392, such as the survey module 204, to perform various functions for the user device 102 and to process data.

In some embodiments, the peripherals interface 370, CPU(s) 374, and memory controller 368 are, optionally, implemented on a single chip. In some other embodiments, they are implemented on separate chips.

RF (radio frequency) circuitry of network interface 384 receives and sends RF signals, also called electromagnetic signals. In some embodiments, the survey module 204, survey questions 208/212, answers to survey questions 208/212, and/or the over-the-counter drug facts label 230 are communicated to the subject device 102 using this RF circuitry. In some embodiments, the RF circuitry 384 converts electrical signals to/from electromagnetic signals and communicates with communications networks and other communications devices and/or the data collection device 200 and/or the dipeptidyl peptidase-4 inhibitor pharmaceutical composition OTC dispensing device 250 via the electromagnetic signals. The RF circuitry 384 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 384 optionally communicates with the communication network 106. In some embodiments, the circuitry 384 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. In some embodiments, the speaker 360 converts the electrical signals to human-inaudible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 392 and/or the RF circuitry 384 by the peripherals interface 370.

In some embodiments, the power supply 376 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 382 on the front of the user device 102, so that the input 380 is enabled for use as a viewfinder for still and/or video image acquisition. In some embodiments, another optical sensor 373 is located on the front of the user device 102 so that the subject's image is obtained (e.g., to verify the health, condition, or identity of the subject as part of qualifying the subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels), to help diagnose a subject's condition remotely, or to acquire visual physiological measurements of the subject, etc.).

As illustrated in FIG. 3, the user device 102 preferably includes an operating system 302 that includes procedures for handling various basic system services. The operating system 302 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the user device 102 is a smart phone or a smart watch. In other embodiments, the user device 102 is not a smart phone or a smart watch but rather is a tablet computer, a desktop computer, an emergency vehicle computer, or other form or wired or wireless networked device. In the interest of brevity and clarity, only a few of the possible components of the user device 102 are shown in FIG. 3 in order to better emphasize the additional software modules that are installed on the user device 102.

While the system 48 disclosed in FIG. 1 can work standalone, in some embodiments it can also be linked with electronic medical record systems to exchange information in any way.

Now that details of a system 48 for qualifying a human subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, have been disclosed, details regarding a method (400), including processes and features to performed by the system, in accordance with an embodiment of the present disclosure, are disclosed with reference to FIGS. 4A through 4I. In some embodiments, such processes and features of the system are carried out by the assessment module 252, reassessment module 254, fulfillment module 228-1, and/or re-fulfillment module 228-2 illustrated in FIGS. 2 and 3. In some embodiments, the assessment module 252, reassessment module 254, fulfillment module 228-1, and/or re-fulfillment module 228-1 are a single software module. In the flow chart, elements in dashed boxes are considered to be optional.

Blocks 402-406.

Referring to block 402 in FIG. 4A, a goal of the present disclosure is to qualify subjects for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels, using a computer system such as a dipeptidyl peptidase-4 inhibitor pharmaceutical composition OTC dispensing device 250. The dipeptidyl peptidase-4 inhibitor pharmaceutical composition OTC dispensing device (e.g., device 250) includes one or more processors (e.g., processor 274) and a memory (e.g., memory 192). The memory stores non-transitory instructions that, when executed by the one or more processors, perform a method.

Referring to block 403, in some embodiments the dipeptidyl peptidase-4 inhibitor pharmaceutical composition the dipeptidyl peptidase-4 inhibitor pharmaceutical composition has a structure of structure (I):

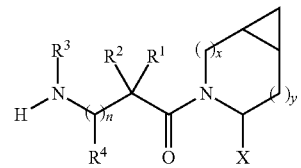

wherein x is 0 or 1 and y is 0 or 1, provided that
x=1 when y=0 and
x=0 when y=1; and wherein
n is 0 or 1;
X is H or CN;
$R^1$, $R^2$, $R^3$ and $R^4$ are the same or different and are independently selected from hydrogen, alkyl, alkenyl, alkynyl, cycloalkyl, cycloalkylalkyl, bicycloalkyl, tricycloalkyl, alkylcycloalkyl, hydroxyalkyl, hydroxyalkylcycloalkyl, hydroxycycloalkyl, hydroxybicycloalkyl, hydroxytricycloalkyl, bicycloalkylalkyl, alkylthioalkyl, arylalkylthioalkyl, cycloalkenyl, aryl, aralkyl, heteroaryl, heteroarylalkyl, cycloheteroalkyl or cycloheteroalkylalkyl; all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfinyl, aminosulfonyl, alkylsulfinyl, sulfonamido or sulfonyl; and
$R^1$ and $R^3$ may optionally be taken together to form —$(CR^5R^6)_m$— where m is 2 to 6, and R and R are the same or different and are independently selected from hydroxy, alkoxy, H, alkyl, alkenyl, alkynyl, cycloalkyl, halo, amino, substituted amino, cycloalkylalkyl, cycloalkenyl, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or $R^1$ and $R^4$ may optionally be taken together to form —$(CR^7R^8)_p$— wherein p is 2 to 6, and $R^7$ and $R^8$ are the same or different and are independently selected from hydroxy, alkoxy, cyano, H, alkyl, alkenyl, alkynyl, cycloalkyl, cycloalkylalkyl, cycloalkenyl, halo, amino, substituted amino, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino;
or optionally $R^1$ and $R^3$ together with

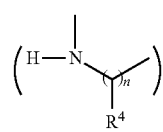

form a 5 to 7 membered ring containing a total of 2 to 4 heteroatoms selected from N, O, S, SO, or SO$_2$;
or optionally R$^1$ and R$^3$ together with

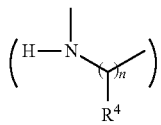

form a 4 to 8 membered cycloheteroalkyl ring wherein the cycloheteroalkyl ring has an optional aryl ring fused thereto or an optional 3 to 7 membered cycloalkyl ring fused thereto;
including all stereoisomers thereof;

Referring to blocks 404-405, in some embodiments the dipeptidyl peptidase-4 inhibitor pharmaceutical composition includes saxagliptin, or a pharmaceutically acceptable salt thereof. In some embodiments, the dipeptidyl peptidase-4 inhibitor pharmaceutical composition includes one of saxagliptin (e.g., (1S,3S,5 S)-2-[(2S)-2-amino-2-(3-hydroxy-1-adamantyl)acetyl]-2-azabicyclo[3.1.0]hexane-3-carbonitrile), sitagliptin (e.g., (3R)-3-amino-1-[3-(trifluoromethyl)-6,8-dihydro-5H-[1,2,4]triazolo[4,3-a]pyrazin-7-yl]-4-(2,4,5-trifluorophenyl)butan-1-one), linagliptin (e.g., 8-[(3R)-3-aminopiperidin-1-yl]-7-but-2-ynyl-3-methyl-1-[(4-methylquinazolin-2-yl)methyl]purine-2,6-dione), alogliptin (e.g., 2-[[6-[(3R)-3-aminopiperidin-1-yl]-3-methyl-2,4-dioxopyrimidin-1-yl]methyl]benzonitrile), or a pharmaceutically acceptable salt thereof. These, and other, dipeptidyl peptidase-4 inhibitor pharmaceutical compositions are described, for example, in Messori et al., Diabetes Ther, 5:341-344 (2014), the content of which is hereby incorporated by reference.

In some embodiments, the dipeptidyl peptidase-4 inhibitor pharmaceutical composition includes any compound disclosed in U.S. Pat. No. 6,395,767, entitled "Cyclopropyl-fused pyrrolidine-based inhibitors of dipeptidyl peptidase IV and method," which is hereby incorporated by reference. In some embodiments, the dipeptidyl peptidase-4 inhibitor pharmaceutical composition includes any compound disclosed in U.S. Pat. No. 7,186,846, entitled "Process for preparing a dipeptidyl peptidase IV inhibitor and intermediates employed therein," which is hereby incorporated by reference.

In some embodiments, the dipeptidyl peptidase-4 inhibitor pharmaceutical composition includes any compound disclosed in U.S. Pat. No. 8,598,347, entitled "Method for manufacturing dipeptidyl peptidase-IV inhibitor and intermediate," which is hereby incorporated by reference. In some embodiments, the dipeptidyl peptidase-4 inhibitor pharmaceutical composition includes any compound disclosed in U.S. Pat. No. 7,470,700, entitled "Dipeptidyl peptidase inhibitors," which is hereby incorporated by reference.

In some embodiments, the dipeptidyl peptidase-4 inhibitor pharmaceutical composition includes any compound disclosed in U.S. Pat. No. 7,420,079, entitled "Methods and compounds for producing dipeptidyl peptidase IV inhibitors and intermediates thereof," which is hereby incorporated by reference. In some embodiments, the dipeptidyl peptidase-4 inhibitor pharmaceutical composition includes any compound disclosed in U.S. Pat. No. 6,812,350, entitled "Synthesis of 3,3,4,4-tetrafluoropyrrolidine and novel dipeptidyl peptidase-IV inhibitor compounds," which is hereby incorporated by reference In some embodiments, the dipeptidyl peptidase-4 inhibitor pharmaceutical composition includes any compound disclosed in U.S. Pat. No. 7,214,702, entitled "Process for producing a dipeptidyl peptidase IV inhibitor," which is hereby incorporated by reference. In some embodiments, the dipeptidyl peptidase-4 inhibitor pharmaceutical composition includes any compound disclosed in U.S. Pat. No. 9,593,119, entitled "Process for the preparation of dipeptidylpeptidase inhibitors," which is hereby incorporated by reference.

Referring to block 406, in some embodiments, the lowering of blood sugar is to treat type 2 diabetes. Typically, this is accomplished by a reduction in blood sugar amount or absorption.

In some embodiments, in response to receiving a first request from a user to be qualified for provision of a dipeptidyl peptidase-4 inhibitor pharmaceutical composition, the system creates a corresponding subject profile, e.g., containing biographic information about the subject, e.g., one or more of a subject name, date of birth, residence, delivery address, social security number, medical record number, insurance information, user name, identification password, etc. In some embodiments, the system registers a subject that has not previously received an over-the-counter provision of a dipeptidyl peptidase-4 inhibitor pharmaceutical composition as a new user of the dipeptidyl peptidase-4 inhibitor pharmaceutical composition, and the device will perform an initial assessment method for qualifying the subject for a provision of the dipeptidyl peptidase-4 inhibitor pharmaceutical composition, e.g., regardless of whether the subject previously received a prescription provision of the dipeptidyl peptidase-4 inhibitor pharmaceutical composition via prescription.

In some embodiments, the system registers a subject that has previously received a provision of a dipeptidyl peptidase-4 inhibitor pharmaceutical composition via prescription as a previous user of the dipeptidyl peptidase-4 inhibitor pharmaceutical composition, and the device will perform a reassessment method for re-qualifying the subject for a provision of the dipeptidyl peptidase-4 inhibitor pharmaceutical composition.

In some embodiments, where the subject previously received a provision of a different dipeptidyl peptidase-4 inhibitor pharmaceutical composition via prescription, the system will perform a modified method for qualifying the subject for provision of dipeptidyl peptidase-4 inhibitor pharmaceutical composition that accounts for differences in the contraindications and risk factors of the two dipeptidyl peptidase-4 inhibitor pharmaceutical composition. For example, in response to receiving a request to qualify a user that previously received a provision of a pharmaceutical composition containing linagliptin via prescription, for an over-the-counter provision of saxagliptin, the system performs a modified method for re-qualifying (e.g., a reassessment) the subject for the dipeptidyl peptidase-4 inhibitor pharmaceutical composition that includes a survey question and corresponding filter relating to whether the subject has ever had heart failure (e.g., regardless of whether a reassessment for a pharmaceutical composition containing saxagliptin would normally consider a subject's history of heart failure), because that factor may not have been considered when the subject received the prescription for the composition containing linagliptin.

In some embodiments, in response to receiving a second or subsequent request from a user to be qualified for provision of a dipeptidyl peptidase-4 inhibitor pharmaceutical composition, the system registers the subject as a returning customer, e.g., when the subject has previously received an over-the-counter provision of the dipeptidyl peptidase-4 inhibitor pharmaceutical composition and a corresponding subject profile 232 already exists for the subject.

Figure 7A:
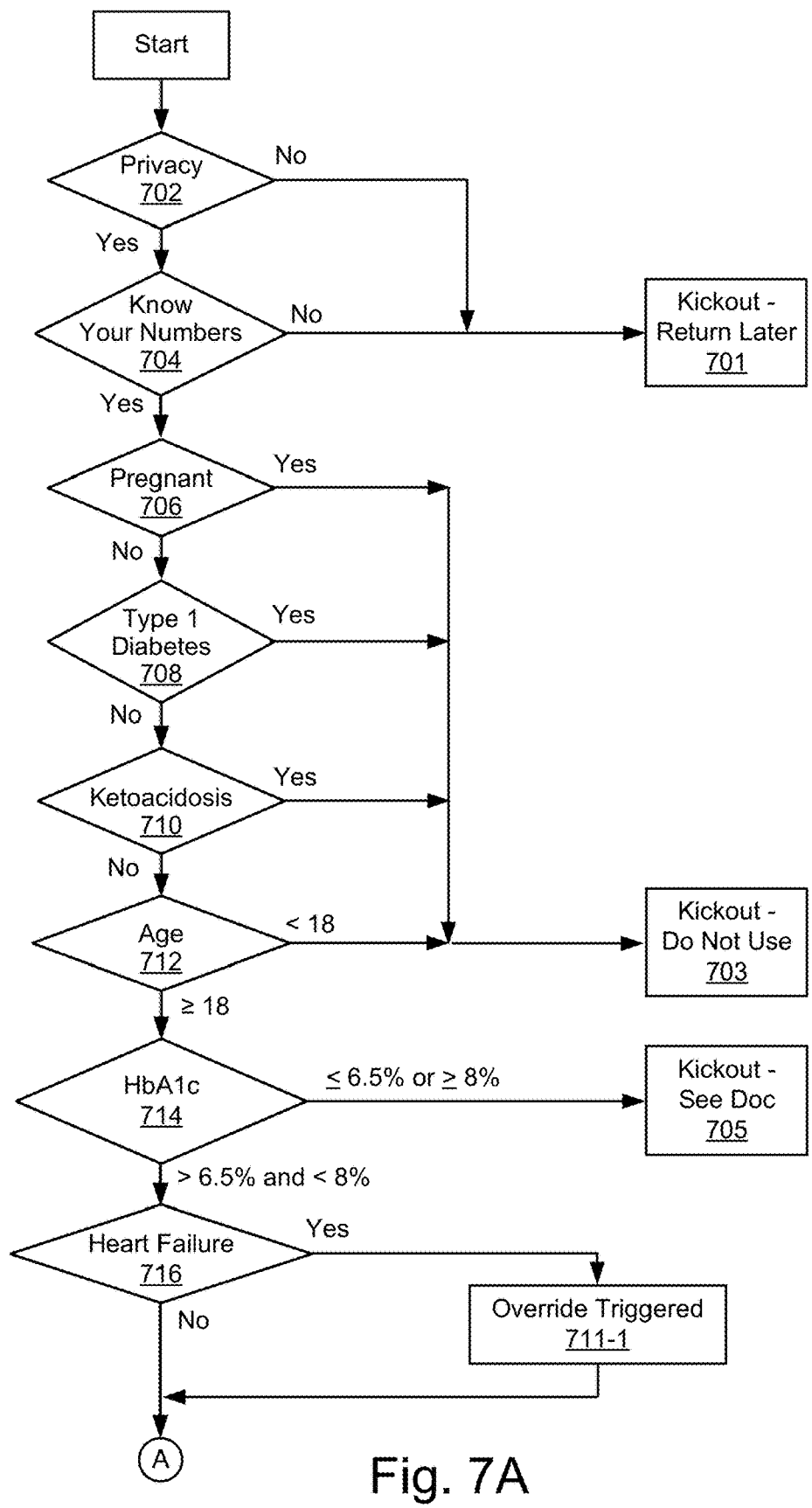
FIGS. 7A, 7B, and 7C collectively illustrate an example method for qualifying a subject for an over-the-counter provision of a dipeptidyl peptidase-4 inhibitor pharmaceutical composition, in accordance with an embodiment of the present disclosure.

In some embodiments, prior to proceeding with the qualification or re-qualification method, the device prompts (702, 704) the user to confirm that they have adequate privacy to provide sensitive medical information (e.g., prompt 702 in FIG. 7A) and/or that they are in possession of medical information required to complete the qualification process (e.g., prompt 704 to confirm that they have knowledge of their blood sugar level, in FIG. 7A).

Blocks 407-411.

Referring to block 407 in FIGS. 4A-4B, the method includes conducting a first survey of the subject thereby obtaining a first plurality of survey results (e.g., in response to survey questions 208, 212, e.g., one or more of the survey questions set forth in Table 1). In some embodiments, the device transmits one or more survey questions to the subject, prompting a response, and then receives a response to the one or more survey questions back from the subject. In some embodiments, the first survey results include, or at least indicate, some or all of the subject characteristics listed in Table 1. For example, in some embodiments, the first plurality of survey results includes, or at least indicates, 2, 3, 4, 5, 6, 7, 8, 9, 10, 11, or all 12 of the characteristics listed in Table 1. In one embodiment, the first survey questions 208, 212 and results include, or indicate, at least characteristics 1-10 as provided in Table 1.

Figures 5A, 5B:
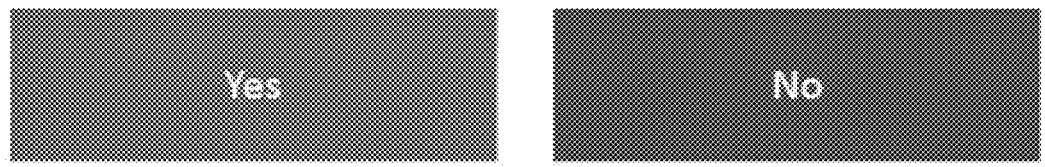
FIGS. 5A, 5B, 5C, and 5D illustrate example survey questions for obtaining survey results, in accordance with an embodiment of the present disclosure.
Figure 5C:
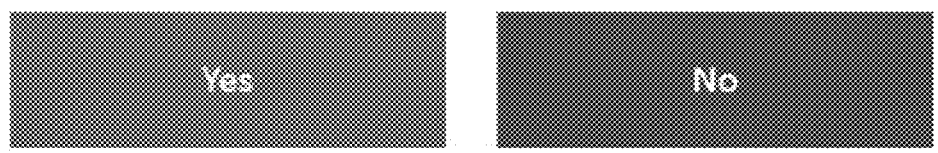
Figure 5D:
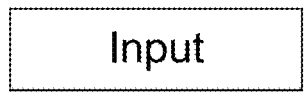
Figure 7B:
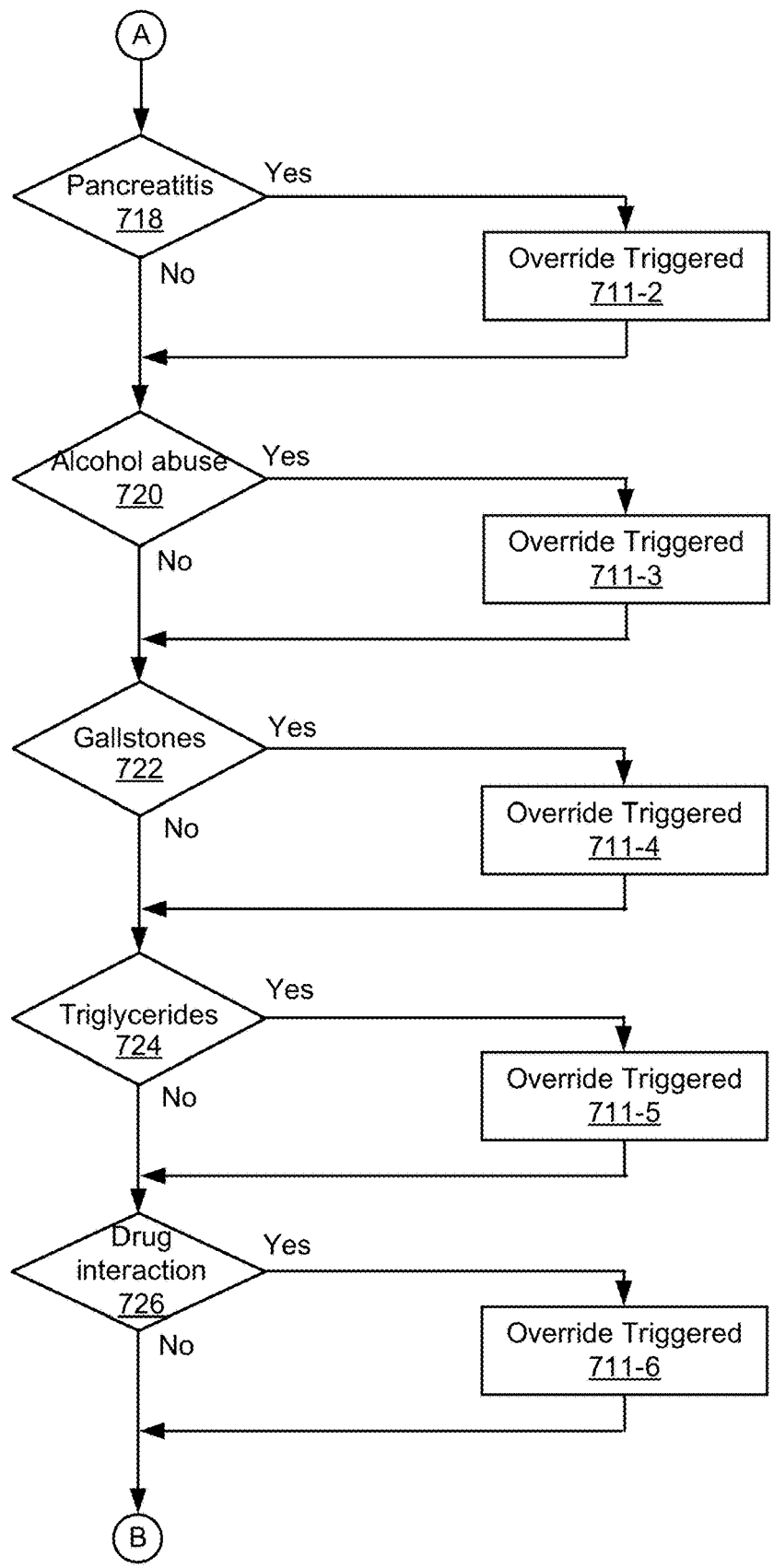
Figure 7C:
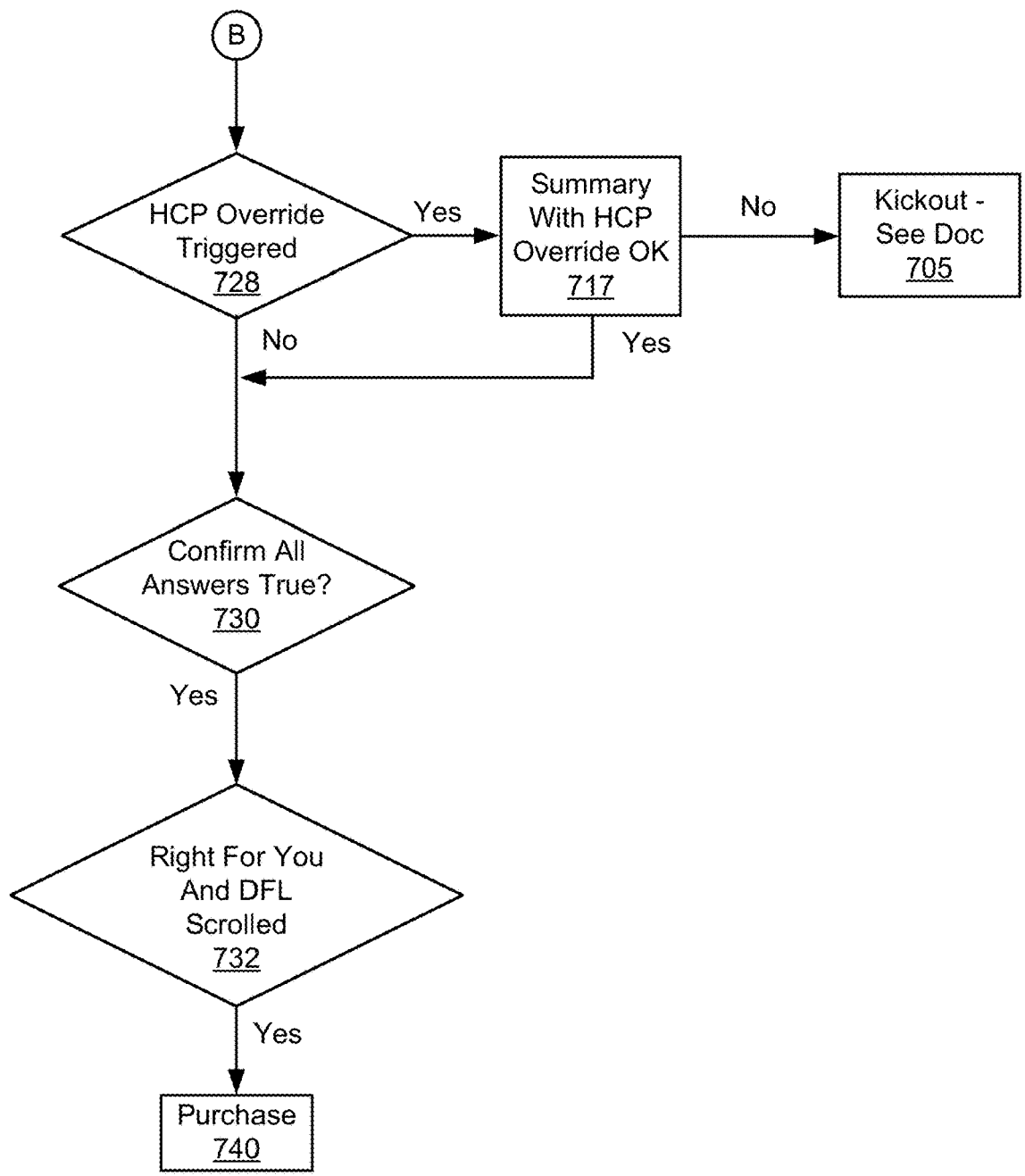

Referring to block 408 in FIG. 4A, e.g., as illustrated in FIGS. 7A-7C, in some embodiments the first survey results indicate whether the subject is one of pregnant, breastfeeding, or planning to become pregnant (e.g., responsive to a survey question 208 such as a question 502 illustrated in FIG. 5A, e.g., that is associated with and/or applied to (706) a pregnancy filter 216-1 of a first category class), whether the subject has Type 1 diabetes (e.g., responsive to a survey question 208 that is associated with and/or applied to (708) a Type 1 diabetes filter 216-2 of a first category class), a ketoacidosis status of the subject (e.g., responsive to a survey question 208 that is associated with and/or applied to (710) a ketoacidosis filter 216-3 of a first category class), an age of the subject (e.g., responsive to a survey question 208 that is associated with and/or applied to (712) an age filter 216-4 of a first category class), a blood sugar level of the subject (e.g., responsive to a survey question 208 such as a question 508 illustrated in FIG. 5D, e.g., that is associated with and/or applied to (714) a blood sugar filter 216-5 of a first category class), whether the subject has ever had a pancreatic problem (e.g., responsive to a survey question 212 that is associated with and/or applied to (718) a pancreatic disease filter 222-1 of a second category class), an alcohol consumption status of the subject, (e.g., responsive to a survey question 212 that is associated with and/or applied to (720) an alcohol consumption filter 222-2 of a second category class), whether the subject has ever has a gallstone, (e.g., responsive to a survey question 212 that is associated with and/or applied to (722) a gallstone filter 222-3 of a second category class), whether the subject has ever had high triglycerides, (e.g., responsive to a survey question 212 that is associated with and/or applied to (724) a triglyceride filter 222-4 of a second category class), and whether the subject is taking a medication that interacts with the dipeptidyl peptidase-4 inhibitor pharmaceutical composition (e.g., responsive to a survey question 212 such as a question 506 illustrated in FIG. 5C, e.g., that is associated with and/or applied to (726) a drug interaction filter 222-5 of a second category class).

In some embodiments, the first survey includes questions that elicit responses providing or indicating some or all of the characteristics listed in Table 1. In some embodiments, the survey includes questions corresponding to each of the survey results required for the methods described herein. In other embodiments, the survey includes questions corresponding to only a subset of the survey results required for the methods described herein. In such embodiments, other survey results required for the methods described herein are acquired through other means (e.g., upon registration/subscription for a service associated with qualifying the subject for over-the-counter medication, from a healthcare professional, from a prior survey, from a database associated with a pharmacy, from an electronic health record associated with the subject, from the subject profile data store 232, etc.) For example, in some embodiments, the subject provides a personal medical identification associated with an insurer, a hospital, or other healthcare professional and information about the subject required for the methods described herein, e.g., one or more survey results, is acquired from a preexisting database associated with the personal medical identification (e.g., a last blood sugar measurement determined for the subject).

TABLE 1

Example characteristics for qualifying a subject for an over-the-counter provision of a dipeptidyl peptidase-4 inhibitor pharmaceutical composition

| Result | Example Characteristics |
| --- | --- |
| 1 | whether the subject is one of pregnant, breastfeeding, or planning to become pregnant |
| 2 | a Type 1 diabetes status of the subject |
| 3 | a ketoacidosis status of the subject |
| 4 | an age of the subject |
| 5 | a blood sugar level of the subject |
| 6 | whether the subject has ever had a pancreatic problem |
| 7 | an alcohol consumption status of the subject |
| 8 | whether the subject has ever had a gallstone |
| 9 | whether the subject has ever had high triglyceride levels |
| 10 | whether the subject is taking a medication that interacts with the dipeptidylpeptidase-4 inhibitor pharmaceutical composition |
| 11 | whether the subject is allergic to the dipeptidyl peptidase-4 inhibitor pharmaceutical composition |
| 12 | whether the subject has ever had heart failure |

It is contemplated that, in some embodiments, survey questions eliciting any one or more of the subject characteristics provided in Table 1 will not be included in the first survey (e.g., will not be used for the assessment). For example, in some embodiments, a characteristic associated with a particular survey questions will be informative when qualifying a subject for one particular dipeptidyl peptidase-4 inhibitor but not for another dipeptidyl peptidase-4 inhibitor. For instance, in one embodiment, a process for qualifying a subject for a pharmaceutical composition containing saxagliptin includes a survey question relating to whether the subject has ever been diagnosed with heart failure, while a process for qualifying a subject for a pharmaceutical composition containing sitagliptin does not have such a question because heart failure is not a risk factor for sitagliptin. The skilled artisan will recognize that different dipeptidyl peptidase-4 inhibitors carry different risks, contraindications, and drug interaction profiles. Accordingly, survey information required for qualifying a subject for access to one different dipeptidyl peptidase-4 inhibitor with a known adverse drug interaction may not be necessary for qualifying the same subject for access to a second, different dipeptidyl peptidase-4 inhibitor.

Accordingly, it is contemplated that the first survey questions 208 include questions eliciting any subset of the subject characteristics provided in Table 1. For brevity, all possible combinations of survey questions 208, 212, eliciting all possible combinations of subject characteristics provided in Table 1, are not specifically delineated here. However, the skilled artisan will be able to envision any particular subset of survey questions 208, 212 eliciting any particular subset of subject characteristics provided in Table 1. Likewise, the skilled artisan may know of survey questions eliciting other subject characteristics, not provided in Table 1, that may be combined with any subset of survey questions eliciting subject characteristics provided in Table 1, to form the first survey questions used in the methods described herein.

In some embodiments, the first and/or second survey is conducted by transmitting a plurality of questions to the subject, e.g., some or all of the survey questions, and receiving answers to the plurality of survey questions before applying any of the answers to respective filters. For example, with reference to the workflow in FIG. 7, the device transmits questions relating to all of the filters of the first category class, all of the filters of the second category class, or all of the filters in the workflow (e.g., as a virtual survey where all of the questions are displayed in a single user interface, or as a series of questions displayed in consecutive user interfaces). After receiving answers to all of the survey questions, the device applies the answers to all of the filters, e.g., sequentially or concurrently, to determine whether the subject is qualified to receive provision of the dipeptidyl peptidase-4 inhibitor pharmaceutical composition.

In alternative embodiments, the device transmits questions relating to just those filters of the first category class for which it could not obtain answers to the questions from an electronic database associated with the subject, such as electronic health record of the subject, and just those filters of the second category class it could not obtain answers to the questions from an electronic database associated with the subject (e.g., as a virtual survey where such unanswered questions are displayed in a single user interface, or as a series of questions displayed in consecutive user interfaces). After receiving answers to all of the survey questions, the device applies the answers to all of the filters (e.g., sequentially or concurrently) to determine whether the subject is qualified to receive provision of the dipeptidyl peptidase-4 inhibitor pharmaceutical composition.

In some embodiments, the first and/or second survey is conducted in a serial fashion, e.g., by transmitting a first question or a first group of survey questions (e.g., associated with a single filter) to the subject, receiving an answer to the single survey question or small group of survey questions, and applying the answer or answers to a filter, prior to transmitting a second question or second group of questions to the subject. For example, with reference to the workflow in FIG. 7, in some embodiments the device transmits a first question to the subject, relating to the pregnancy and/or breastfeeding status of the subject (e.g., question 502 'Are you or do you plan to become pregnant? Are you breastfeeding or planning to breastfeed?' in FIG. 5A). After receiving the answer to the survey question (e.g., 'yes or no'), the device applies the answer to a first pregnancy filter (706). If the first pregnancy filter is fired (e.g., in response to a "yes" answer), the device terminates (703) the process, and optionally provides the user with a message relating to why they are being denied a provision of the dipeptidyl peptidase-4 inhibitor pharmaceutical composition (e.g., as illustrated in FIG. 5B, message 504, advising the subject that taking the dipetidyl peptidase-4 inhibitor pharmaceutical composition creates a risk for the fetus/baby).

Referring to block 409 in FIG. 4A, in some embodiments, the first plurality of survey results further indicates whether the subject is allergic to the dipeptidyl peptidase-4 inhibitor pharmaceutical composition (e.g., subject characteristic 11 in Table 1). In some embodiments, the first plurality of filters further includes an adverse reaction filter that is fired when the first plurality of survey results indicates that the subject is allergic to the dipeptidyl peptidase-4 inhibitor pharmaceutical composition (e.g., filter 6a in Table 2). If the adverse reaction filter is fired, the subject is not permitted to obtain the dipeptidyl peptidase-4 inhibitor pharmaceutical composition pharmaceutical composition over-the-counter (e.g., the method is terminated without authorizing provision of the dipeptidyl peptidase-4 inhibitor pharmaceutical composition to the subject).

Referring to blocks 410-411 in FIG. 4B, in some embodiments the first plurality of survey results further indicates whether the subject has ever had heart failure (e.g., subject characteristic 12 in Table 1). In some embodiments, (and as described below referring to block 423), the second plurality of filters further includes a heart failure filter that is fired when the first plurality of survey results indicates that the subject has had heart failure (e.g., filter 6a in Table 3). In some embodiments, a symptom of heart failure that is capable of firing the heart failure symptom filter is selected from the group consisting of increased shortness of breath, trouble breathing, a rapid increase in weight, swelling of the feet, swelling of the ankles, and swelling of the legs. When the heart failure filter is fired, the device transmits a warning corresponding to the heart failure filter, and requires the user to acknowledge the warning before authorizing a provision of the dipeptidyl peptidase-4 inhibitor pharmaceutical composition.

Blocks 412-421.

Referring to block 412 in FIGS. 4B-4C, all or a portion of the first survey results are run against a first plurality of filters of a first category class 214. As previously described, the first plurality of filters includes a subset of filters 216 of the first filter category class 214. When a respective filter in the first plurality of filters is fired (e.g., when a survey result indicates that a triggering condition 218 has been met), the subject is deemed not qualified for delivery of the dipeptidyl peptidase-4 inhibitor pharmaceutical composition and the method is terminated without delivery of the dipeptidyl peptidase-4 inhibitor pharmaceutical composition.

In some embodiments, when the method is terminated without delivery of the dipeptidyl peptidase-4 inhibitor pharmaceutical composition, the subject is prevented from attempting to requalify for the dipeptidyl peptidase-4 inhibitor pharmaceutical composition for a predetermined period of time, e.g., at least a day, at least a week, at least a month, etc. This prevents the subject from abusing the systems and methods of the present disclosure.

Referring to blocks 413-422, specific filters 216 in the first plurality of filters and their exemplary triggering conditions 218 that cause the corresponding filter to fire are detailed below.

In some embodiments, the first plurality of filters of the first category class 214 includes some or all of the filters 216 listed in Table 2. For example, in some embodiments, the first plurality of filters results includes 2, 3, 4, 5, or all 6, of the filters listed in Table 2. In one embodiment, the first plurality of filters includes at least filters 1-5 as provided in Table 2.

TABLE 2

Example filters for contraindications associated with qualifying a subject for an over-the-counter provision of a dipeptidyl peptidase-4 inhibitor pharmaceutical composition

| Filter | Example Criteria |
|---|---|
| 1a | a pregnancy filter |
| 2a | a Type 1 diabetes filter |
| 3a | a ketoacidosis filter |
| 4a | an age filter |
| 5a | a blood sugar filter |
| 6a | an adverse reaction filter |

It is contemplated that, in some embodiments, any one or more of the filters 216 provided in Table 2 will not be included in the first plurality of filters. For example, in some embodiments, a characteristic associated with a particular survey result will be informative when qualifying a subject for one particular dipeptidyl peptidase-4 inhibitor but not for another dipeptidyl peptidase-4 inhibitor.

Accordingly, it is contemplated that the first plurality of filters includes any sub-set of filters 216 provided in Table 2. Likewise, the skilled artisan may know of other filters 216, not provided in Table 2, which may be combined with any subset of the filters 216 provided in Table 2 to form the first plurality of filters results used in the methods described herein. For brevity, all possible combinations of the filters 216 provided in Table 2 are not specifically delineated here.

Referring to blocks 413-414 in FIG. 4B, in some embodiments the first plurality of filters includes a pregnancy filter (e.g., pregnancy filter 216-1 in FIG. 3 and/or filter 1a in Table 2). In some embodiments, the first pregnancy filter is configured to be fired at least when the first plurality of survey results indicates that the subject is pregnant or the subject is breastfeeding. In some embodiments, the first pregnancy filter is also configured to be fired when the subject is planning on becoming pregnant, e.g., within a predetermined period of time. When the first pregnancy filter is fired, the subject is not permitted to obtain the dipeptidyl peptidase-4 inhibitor pharmaceutical composition over-the-counter (e.g., the method is terminated without authorizing provision of the dipeptidyl peptidase-4 inhibitor pharmaceutical composition to the subject). For example, the device transmits prompt 502, as illustrated in FIG. 5A, to the subject and the device applies the subject's answer to the first pregnancy filter. If the subject's answer indicates that they are pregnant, they are planning on becoming pregnant, they are breastfeeding, or they are planning to breastfeeding, the pregnancy filter is fired, and the method is terminated without authorizing provision of the dipeptidyl peptidase-4 inhibitor pharmaceutical composition to the subject. In some embodiments, the device transmits a message explaining why authorization was denied, e.g., message 504 illustrated in FIG. 5B.

Referring to block 415 in FIG. 4B, in some embodiments the first plurality of filters includes a Type 1 diabetes filter (e.g., Type 1 diabetes filter 216-2 in FIG. 3 and/or filter 2a in Table 2). The Type 1 diabetes filter is configured to be fired at least when the first plurality of survey results indicates that the subject has Type 1 diabetes. If the Type 1 diabetes filter is fired, the subject is not permitted to obtain the dipeptidyl peptidase-4 inhibitor pharmaceutical composition pharmaceutical composition over-the-counter (e.g., the method is terminated without authorizing provision of the dipeptidyl peptidase-4 inhibitor pharmaceutical composition to the subject).

Referring to block 416 in FIG. 4B, in some embodiments the first plurality of filters includes a ketoacidosis filter (e.g., ketoacidosis filter 216-3 in FIG. 3 and/or filter 3a in Table 2). The ketoacidosis filter is configured to be fired at least when the first plurality of survey results indicates that the subject has ketoacidosis. If the ketoacidosis filter is fired, the subject is not permitted to obtain the dipeptidyl peptidase-4 inhibitor pharmaceutical composition pharmaceutical composition over-the-counter (e.g., the method is terminated without authorizing provision of the dipeptidyl peptidase-4 inhibitor pharmaceutical composition to the subject).

Referring to blocks 417-418 in FIG. 4C, in some embodiments the first plurality of filters includes an age filter (e.g., age filter 216-4 in FIG. 3 and/or filter 4a in Table 2). In some embodiments, the age filter is fired when the first plurality of survey results indicates that the subject is less than eighteen years old. If the age filter is fired, the subject is not permitted to obtain the dipeptidyl peptidase-4 inhibitor pharmaceutical composition pharmaceutical composition over-the-counter (e.g., the method is terminated without authorizing provision of the dipeptidyl peptidase-4 inhibitor pharmaceutical composition to the subject).

Referring to blocks 419-421 in FIG. 4C, in some embodiments the first plurality of filters includes a first blood sugar filter (e.g., blood sugar filter 216-5 in FIG. 3 and/or filter 5a in Table 2). In some embodiments, the first blood sugar filter is fired when the first plurality of survey results indicates that the subject does not have a moderately elevated blood sugar level, e.g., a blood sugar level that is either below a first floor blood sugar level (e.g., in a normal range that does not warrant treatment with a dipeptidyl peptidase-4 inhibitor containing composition), or above a ceiling blood sugar level (e.g., in a highly elevated range that warrants treatment with a stronger, prescription medication). If the first blood sugar filter is fired, the subject is not permitted to obtain the dipeptidyl peptidase-4 inhibitor pharmaceutical composition over-the-counter (e.g., the method is terminated without authorizing provision of the dipeptidyl peptidase-4 inhibitor pharmaceutical composition to the subject). In some embodiments, the floor blood sugar level used in the first blood sugar filter is 6.5% glycated hemoglobin. In some embodiments, the first ceiling blood sugar level used in the first blood sugar filter is 7.5% glycated hemoglobin.

Blocks 423-431.

Referring to block 423 in FIGS. 4C-4D, the method also includes running all or a portion of the first survey results against a second plurality of filters of a second category class 220. When a respective filter in the second plurality of filters is fired, the subject is provided with a warning 226 corresponding to the respective filter (e.g., filter warning 226-4 corresponds to filter 222-4). In some embodiments, the warning 226 is provided as a next step, e.g., prior to applying survey results to any subsequent filters, after the corresponding filter is fired. For example, with respect to FIG. 7B in some embodiments, when the pancreatitis filter is triggered at 718, the device would provide the subject with a warning prior to proceeding to the alcohol consumption filter at 720, e.g., requiring the subject confirm they have discussed their history of pancreatitis with a health care professional, e.g., and the healthcare professional still recommends taking a dipeptidyl peptidase-4 inhibitor pharmaceutical composition. In some embodiments the warning 226 is provided after applying survey results to all subsequent filters. For example, as illustrated in FIG. 7B-7B, in some embodiments, when the lever pancreatitis filter is triggered at 718, the device would proceed to the alcohol consumption filter at 720 prior to transmitting a warning to the subject, and transmit all warnings corresponding to filters of the second category class, at 717, as illustrated in FIG. 7C, after survey results have been applied to all subsequent filters.

In some embodiments, the second plurality of filters 222 of the second category class 220 includes some or all of the filters listed in Table 3. For example, in some embodiments, the first plurality of filters results includes 2, 3, 4, 5, or all 6, of the filters listed in Table 3. In one embodiment, the first plurality of filters includes at least characteristics 1-5 as provided in Table 3.

TABLE 3

Example filters for risk factors associated with qualifying a subject for an over-the- counter provision of a dipeptidyl peptidase-4 inhibitor pharmaceutical composition

| Filter | Example Criteria |
|---|---|
| 1a | a pancreatic disease filter |
| 2a | an alcohol consumption filter |
| 3a | a gallstone filter |
| 4a | a triglyceride filter |
| 5a | a drug interaction filter |
| 6a | a heart failure filter |

Referring to block 425 in FIG. 4C, in some embodiments, the second plurality of filters includes a pancreatic disease filter (e.g., pancreatic disease filter 222-1 in FIG. 3 and/or filter 1a in Table 3). The pancreatic disease filter is configured to be fired at least when the first plurality of survey results indicate that the subject has pancreatitis. When the pancreatic disease filter is fired, the device transmits a warning corresponding to the pancreatic disease filter, and requires the user to acknowledge the warning before authorizing a provision of the dipeptidyl peptidase-4 inhibitor pharmaceutical composition.

Referring to blocks 426-427 in FIG. 4D, in some embodiments, the second plurality of filters includes an alcohol consumption filter (e.g., alcohol consumption filter 222-2 in FIG. 3 and/or filter 2a in Table 3). The alcohol consumption filter is configured to be fired when the first plurality of survey results indicates that that the subject drinks alcohol very often, e.g., on average consumes at least a predetermined number of alcoholic drinks over a predetermined period of time. In some embodiments, the predetermined number of alcoholic drinks over a predetermined period of time is at least one alcoholic drink per day, at least two alcoholic drinks per day, at least three alcoholic drinks per day, or four or more alcoholic drinks per day. In some embodiments, the predetermined number of alcoholic drinks over a predetermined period of time is at least four, five, six, seven, eight, nine, ten, or more drinks per week. In some embodiments, the alcohol consumption filter is configured to be fired when the first plurality of survey results indicates that the subject has a history of binge drinking, e.g., drinking a lot of alcohol in a short time. When the alcohol consumption filter is fired, the device transmits a warning corresponding to the alcohol consumption filter, and requires the user to acknowledge the warning before authorizing a provision of the dipeptidyl peptidase-4 inhibitor pharmaceutical composition.

Referring to block 428 in FIG. 4D, in some embodiments, the second plurality of filters includes a gallstone filter (e.g., gallstone filter 222-3 in FIG. 3 and/or filter 3a in Table 3). The gallstone filter is configured to be fired at least when the first plurality of survey results indicates that the subject has had a gallstone. When the gallstone filter is fired, the device transmits a warning corresponding to the gallstone filter, and requires the user to acknowledge the warning before authorizing a provision of the dipeptidyl peptidase-4 inhibitor pharmaceutical composition.

Referring to block 429 in FIG. 4D, in some embodiments, the second plurality of filters includes a triglyceride filter (e.g., triglyceride filter 222-4 in FIG. 3 and/or filter 4a in Table 3). The triglyceride filter is configured to be fired when the first plurality of survey results indicates that the subject has a high triglyceride level (e.g., greater than 500 mg/dL). In some embodiments, the first plurality of survey results indicates that the subject has a high triglyceride level when they indicate that the subject has been told by a medical professional that they have high triglyceride levels (e.g., regardless of whether the subject provides a value for their triglyceride levels). In some embodiments, the first plurality of survey results indicates that the subject has a high triglyceride level when they indicate that the subject's triglyceride levels are above a threshold level (e.g., 500 mg/dL). In some embodiments, a threshold triglyceride level is set according to guidelines provided for managing diabetes, e.g., the American Diabetes Association "Standards of Medical Care in Diabetes—2018", Diabetes Care, 41(S1): S1-S159, which is incorporated by reference herein. When the triglyceride filter is fired, the device transmits a warning corresponding to the triglyceride filter, and requires the user to acknowledge the warning before authorizing a provision of the dipeptidyl peptidase-4 inhibitor pharmaceutical composition.

Referring to blocks 430-431 in FIG. 4D, in some embodiments, the second plurality of filters includes a first drug interaction filter (e.g., first drug interaction filter 222-5 in FIG. 3 and/or filter 5a in Table 3). The first drug interaction filter is configured to be fired at least when the first plurality of survey results indicates that the subject is taking a medication that interacts with the dipeptidyl peptidase-4 inhibitor pharmaceutical composition. When the first drug interaction filter is fired, the device transmits a warning corresponding to the first drug interaction filter, and requires the user to acknowledge the warning before authorizing a provision of the dipeptidyl peptidase-4 inhibitor pharmaceutical composition. In some embodiments, the medication that interacts with the dipeptidyl peptidase-4 inhibitor pharmaceutical composition, which is capable of firing the first drug interaction filter, is selected from the group consisting of an HIV medication, an AIDS medication, an antifungal medication, an antibiotic, or a medication for diabetes.

The skilled artisan will recognize that different dipeptidyl peptidase-4 inhibitors exhibit different drug interaction profiles. Accordingly, survey questions and information required for qualifying a subject for access to one dipeptidyl peptidase-4 inhibitor with a known adverse drug interaction may not be necessary for qualifying the same subject for access to a second dipeptidyl peptidase-4 inhibitor. For example, sitagliptin has known adverse interactions with the antibiotic gatifloxacin. Both alogliptin and linagliptin have warnings about adverse interactions with other medications intended to lower blood sugar (e.g., other medications used to treat type 2 diabetes and/or maintain sub-diabetic blood sugar levels). Linagliptin further has known adverse interactions with the antibiotic rifampicin. Saxagliptin also has known adverse interactions with antifungals (e.g., ketoconazole), HIV medications, and AIDS medications.

It is contemplated that, in some embodiments, any one or more of the filters provided in Table 3 will not be included in the second plurality of filters. For example, in some embodiments, a characteristic associated with a particular survey result will be informative when qualifying a subject for one particular dipeptidyl peptidase-4 inhibitor pharmaceutical composition but not for another dipeptidyl peptidase-4 inhibitor pharmaceutical composition. Accordingly, it is contemplated that the second plurality of filters includes any sub-set of filters provided in Table 3. Likewise, the skilled artisan may know of other filters, not provided in Table 3, that may be combined with any subset of the filters provided in Table 3 to form the second plurality of filters results used in the methods described herein.

Contraindications and risk factors described in the present disclosure are non-exhaustive. The skilled artisan may know of other contraindications for a particular the dipeptidyl peptidase-4 inhibitor pharmaceutical composition and/or treat risk factors as contraindications dependent upon the intended use of the dipeptidyl peptidase-4 inhibitor pharmaceutical composition. In some embodiments, contraindications for use of a prescription-strength pharmaceutical agent are treated only as risk factors, or not at all, when qualifying a subject for a lower-dose OTC use of a dipeptidyl peptidase-4 inhibitor pharmaceutical composition.

Accordingly, it will be appreciated that the survey questions 208, 212, and filters 216, 222 applied to the survey answers thereof, may vary depending upon the dipeptidyl peptidase-4 inhibitor pharmaceutical composition being distributed. This is due to differences in the contraindication profiles of the various the dipeptidyl peptidase-4 inhibitor pharmaceutical compositions, e.g., due to different drug-drug interactions, routes of drug clearance, etc. of the different the dipeptidyl peptidase-4 inhibitor pharmaceutical compositions.

Referring to block 433 in FIG. 4D, the method includes obtaining acknowledgment from the subject for any warning 226 issued to the subject by any filter 222 in the second plurality of filters.

Figure 6:
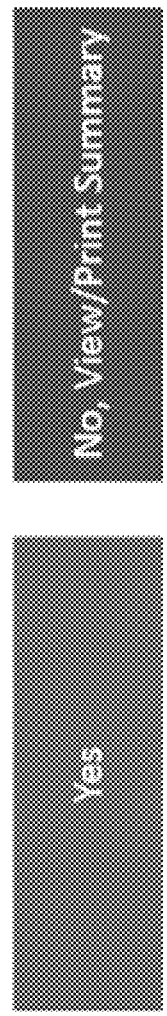
FIG. 6 illustrates feedback from a first survey in accordance with an embodiment of the present disclosure.

Referring to block 424, in some embodiments the warning 226 corresponding to a respective filter 222 in the second plurality of filters includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a dipeptidyl peptidase-4 inhibitor pharmaceutical composition in view of the underlying risk factor. Accordingly, acknowledgement is obtained from the subject when the subject indicates that they have discussed the risk factor underlying the respective filter in the second plurality of filters that was fired with a health care professional. For example, message 602 in FIG. 6 illustrates a warning that is generic to any fired filters. In some embodiments, the warning is specific to a particular filter (e.g., filter warning 226 in FIG. 2), communicating to the user why the filter was fired.

In some embodiments, an acknowledgment from the user is verified by the health care practitioner (e.g., the method requires verification in order for authorization of the provision of the dipeptidyl peptidase-4 inhibitor pharmaceutical composition), for example in order to verify an accuracy of the survey results of the subject. In some embodiments, when the acknowledgment is verified by the heath care practitioner, the subject is deemed a trusted subject, such that verification of future results is not required.

Blocks 435-439.

Referring to block 435 in FIG. 4E, the process control proceeds to the fulfillment process when no filter 216 in the first plurality of filters has been fired and the subject has acknowledged each warning 226 associated with each filter 222 in the second plurality of filters that was fired.

Referring to blocks 436-437 in FIG. 4E, in some embodiments, the fulfillment process includes storing an indication in a subject profile 232 of an initial order date and/or destination for the dipeptidyl peptidase-4 inhibitor pharmaceutical composition. The initial order date is utilized, for example, to verify at least a refill status of a provision of the dipeptidyl peptidase-4 inhibitor. The initial order date is also utilized, for example, to verify at least an elapsed period of time between an initial order and a future re-order. Such verification is required in order to ensure that certain tests (e.g., blood sugar tests) are taken regularly.

The fulfillment process further includes communicating an over-the-counter drug facts label 230 for the dipeptidyl peptidase-4 inhibitor pharmaceutical composition to the subject and authorizing, upon confirmation from the subject that the over the counter drug facts label has been received and read, provision of the dipeptidyl peptidase-4 inhibitor pharmaceutical composition to the subject. In some embodiments, the drug facts label is communicated to the subject in real-time, e.g., within the same user interface as used for the qualification process. In some embodiments, the over-the-counter drug facts label 230 specifies what the dipeptidyl peptidase-4 inhibitor pharmaceutical composition is for (e.g., for lowering blood sugar, e.g., thereby, treating Type 2 diabetes and/or maintaining sub-diabetic blood sugar levels) and any risks associated with taking the dipeptidyl peptidase-4 inhibitor pharmaceutical composition (e.g., drug-drug interactions, pharmacokinetic interactions, adverse reactions, etc.). In some embodiments, upon confirmation from the subject that the over the counter drug facts label has been received and read, the subject is authorized for provision of a dosage of 2.5 mg per day of saxagliptin (block 437).

Referring to block 438 in FIG. 4E, in some embodiments the fulfillment process further includes storing the destination associated with the subject in the subject profile 232. In some embodiments, the destination associated with the subject is a physical address including a street address, a Post Office box, a pharmacy associated with the subject, a health care professional associated with the subject, and/or one or more coordinates (e.g., longitude, latitude, elevation).

Referring to block 439 in FIG. 4E, in some embodiments, the provision of the dipeptidyl peptidase-4 inhibitor pharmaceutical composition to the subject includes shipping the dipeptidyl peptidase-4 inhibitor pharmaceutical composition to the physical address associated with the subject. In some embodiments, the provision of the dipeptidyl peptidase-4 inhibitor pharmaceutical composition to the subject includes shipping the dipeptidyl peptidase-4 inhibitor pharmaceutical composition to a pharmacy associated and/or a location associated with a health care professional of the subject and/or an office of a medical practitioner associated with the subject.

Blocks 442-469.

Referring to blocks 442-469 in FIGS. 4E-4I, a re-fulfillment process will be described infra. In some embodiments, the present disclosure provides a method for qualifying a subject for a refill of a dipeptidyl peptidase-4 inhibitor pharmaceutical composition. In some embodiments, the qualification for a refill of the dipeptidyl peptidase-4 inhibitor pharmaceutical composition follows an initial qualification of the subject, as described herein. In some embodiments, the qualification for a refill of the dipeptidyl peptidase-4 inhibitor pharmaceutical composition follows issuance of a prescription to the subject for a dipeptidyl peptidase-4 inhibitor pharmaceutical composition. For example, in some embodiments, a subject who is new to the qualification process is asked whether they previously received a prescription for the dipeptidyl peptidase-4 inhibitor pharmaceutical composition and, if the subject indicates that they have not previously received a prescription, the subject is directed to an initial qualification method and, if the subject indicates that they have previously received a prescription, the subject is directed to the refill qualification method, e.g., as described below.

Referring to block 442 in FIG. 4E, in some embodiments a re-fulfillment procedure is performed. The re-fulfillment procedure is responsive to receiving a re-order request from the subject for the dipeptidyl peptidase-4 inhibitor pharmaceutical composition. In some embodiments, a prompt to initiate the re-fulfillment procedure is sent to user device 102 associated with the subject after a predetermined amount of time associated with a duration of dosages previously delivered to the subject (e.g., the user is reminded to fulfill their order of the dipeptidyl peptidase-4 inhibitor pharmaceutical composition just before, or just after, the user is scheduled to run out of a previously delivered provision).

Referring to blocks 443-444 in FIG. 4F, in some embodiments the re-fulfillment procedure includes conducting a second survey of the subject. The second survey is configured to obtain a second plurality of survey results. These results are derived from corresponding survey questions (e.g., the device transmits one or more survey questions to the user, prompting a response, and receives a response to the one or more survey questions back from the subject). In some embodiments, the second plurality of survey results indicate some or all of the characteristics listed in Table 4. For example, in some embodiments, the second plurality of survey results indicates 1, 2, 3, 4, 5, 6, 7, 8, 9, 10, 11, or all 12 of the characteristic listed in Table 4. In one embodiment, the second survey results indicate at least characteristics 1-8, as provided in Table 4. In one embodiment, the second survey results indicate at least characteristics 1-9, as provided in Table 4.

In some embodiments, the second survey results indicates at least one of: whether the subject is one of pregnant, breastfeeding, or planning to become pregnant (e.g., responsive to a survey question that is associated with and/or applied to (808) a pregnancy filter of a first category class 214-2), whether the subject has developed ketoacidosis since receiving their last provision of the dipeptidyl peptidase-4 inhibitor pharmaceutical composition (e.g., responsive to a survey question that is associated with and/or applied to (810), a ketoacidosis filter of a first category class 214-2), whether the subject has experienced a skin problem since receiving their last provision of the dipeptidyl peptidase-4 inhibitor pharmaceutical composition (e.g., responsive to a survey question that is associated with and/or applied to (814), a skin problem filter of a first category class 214-2), whether the subject has experienced stomach pain since receiving their last provision of the dipeptidyl peptidase-4 inhibitor pharmaceutical composition (e.g., responsive to a survey question that is associated with and/or applied to (816), a stomach pain filter of a first category class 214-2), whether the subject has experienced joint pain since receiving their last provision of the dipeptidyl peptidase-4 inhibitor pharmaceutical composition (e.g., responsive to a survey question that is associated with and/or applied to (818), a joint pain filter of a first category class 214-2), whether the subject has developed hypoglycemia since receiving their last provision of the dipeptidyl peptidase-4 inhibitor pharmaceutical composition (e.g., responsive to a survey question that is associated with and/or applied to (820) a hypoglycemia filter of a second category class 220-2), whether the subject is experiencing a bodily stress (e.g., responsive to a survey question that is associated with and/or applied to (822) a bodily stress filter of a second category class 220-2), whether the subject is taking a medication that interacts with the dipeptidyl peptidase-4 inhibitor pharmaceutical composition (e.g., responsive to a survey question that is associated with and/or applied to (824) a drug interaction filter of a second category class 220-2), and if a predetermined period of time (826) has passed since the user received a provision of the dipeptidyl peptidase 4 inhibitor blocker pharmaceutical composition, a blood sugar level of the subject (e.g., responsive to a survey question that is associated with and/or applied to (827) a blood sugar filter of a second category class 220-2).

In some embodiments, the second survey includes questions that elicit responses providing some or all of the characteristics listed in Table 4. In some embodiments, the second survey includes questions corresponding to each of the survey results required for the methods described herein. In other embodiments, the second survey includes questions corresponding to only a subset of the survey results required for the methods described herein. In such embodiments, other survey results required for the methods described herein are acquired through other means (e.g., upon registration/subscription for a service associated with qualifying the subject for over-the-counter medication, from a healthcare professional, from a prior survey, from a database associated with a pharmacy, etc.) For example, in some embodiments, the subject provides a personal medical identification associated with an insurer, a hospital, or other healthcare professional and information about the subject required for the methods described herein, e.g., one or more survey results, is acquired from a preexisting database associated with the personal medical identification (e.g., a last blood sugar measurement determined for the subject).

TABLE 4

Example characteristics for qualifying a subject for an over-the-counter provision of a dipeptidyl peptidase-4 inhibitor pharmaceutical composition

| Result | Example Characteristics |
|---|---|
| 1 | whether the subject is one of (i) pregnant, (ii) breastfeeding, or (iii) planning tobecome pregnant |
| 2 | whether the subject has developed ketoacidosis |
| 3 | whether the subject has experienced a skin problem |
| 4 | whether the subject has experienced stomach pain |
| 5 | whether the subject has experienced joint pain |
| 6 | whether the subject has developed hypoglycemia |
| 7 | whether the subject is experiencing a bodily stress |
| 8 | whether the subject is taking a medication that interacts with the dipeptidyl peptidase-4 inhibitor pharmaceutical composition |
| 9 | a blood sugar level of the subject |
| 10 | whether the subject has experienced a side effect from the dipeptidyl peptidase-4 inhibitor pharmaceutical composition |
| 11 | whether the subject has developed heart failure |

It is contemplated that, in some embodiments, survey questions eliciting any one or more of the subject characteristics provided in Table 4 will not be included in the second survey (e.g., will not be used for the reassessment). For example, in some embodiments, a characteristic associated with a particular survey questions will be informative when qualifying a subject for one particular dipeptidyl peptidase-4 inhibitor but not for another dipeptidyl peptidase-4 inhibitor. For instance, in one embodiment, a process for re-qualifying a subject for a pharmaceutical composition containing saxagliptin includes a survey question relating to whether the subject has ever been diagnosed with heart failure, while a process for qualifying a subject for a pharmaceutical composition containing sitagliptin does not have such a question because heart failure is not a risk factor for sitagliptin. Accordingly, survey information required for qualifying a subject for access to one dipeptidyl peptidase-4 inhibitor with a known adverse drug interaction may not be necessary for qualifying the same subject for access to a second dipeptidyl peptidase-4 inhibitor.

Accordingly, it is contemplated that the second survey questions elicit responses corresponding to any sub-set of subject characteristics provided in Table 4. For brevity, all possible combinations of the characteristics provided in Table 4 are not specifically delineated here. However, the skilled artisan will easily be able to envision any particular subset of survey questions designed to elicit responses to any subset of characteristics provided in Table 4. Likewise, the skilled artisan may know of survey questions eliciting other subject characteristics, not provided in Table 4, that may be combined with any subset of the survey questions eliciting subject characteristics provided in Table 4, to form the second survey questions used in the methods described herein.

Referring to blocks 445-454 in FIG. 4F-4G, all or a portion the results from the second survey are run against a third plurality of filters of the first category class. When a respective filter in the third plurality of filters is fired (e.g., when a survey result indicates that a triggering condition 218 has been met), the subject is deemed not qualified for the dipeptidyl peptidase-4 inhibitor pharmaceutical composition and the method is terminated without delivery of the dipeptidyl peptidase-4 inhibitor pharmaceutical composition. Specific filters in the third plurality of filters and their exemplary triggering conditions that cause the corresponding filter to fire are detailed.

In some embodiments, the third plurality of filters of the first category class include some or all of the filters listed in Table 5. For example, in some embodiments, the first plurality of filters results includes 2, 3, 4, 5, 6, or all 7 of the filters listed in Table 5. In one embodiment, the first plurality of filters includes at least filters 1-6 as provided in Table 5.

TABLE 5

Example filters for contraindications associated with qualifying a subject for an over-the-counter provision of a dipeptidyl peptidase-4 inhibitor pharmaceutical composition

| Filter | Example Criteria |
|---|---|
| 1a | a pregnancy filter |
| 2a | a ketoacidosis symptom filter |
| 3a | a skin problem filter |
| 4a | a stomach pain filter |
| 5a | a joint pain filter |
| 6a | a blood sugar status filter |
| 7a | a heart failure symptom filter |

It is contemplated that, in some embodiments, any one or more of the filters provided in Table 5 will not be included in the third plurality of filters. For example, in some embodiments, a characteristic associated with a particular survey result will be informative when qualifying a subject for one particular dipeptidyl peptidase-4 inhibitor but not for another dipeptidyl peptidase-4 inhibitor. Likewise, the skilled artisan may know of other filters, not provided in Table 5, which may be combined with any subset of the filters provided in Table 2 to form the third plurality of filters results used in the methods described herein. For brevity, all possible combinations of the filters provided in Table 5 are not specifically delineated here.

Referring to blocks 446-447 in FIG. 4F, in some embodiments the third plurality of filters includes a pregnancy filter. In some embodiments, the second pregnancy filter is configured to be fired at least when the first plurality of survey results indicates that the subject is pregnant or the subject is breastfeeding. In some embodiments, the second pregnancy filter is also configured to be fired when the subject is planning on becoming pregnant within a predetermined period of time. When the pregnancy filter is fired, the subject is not permitted to obtain the dipeptidyl peptidase-4 inhibitor pharmaceutical composition over-the-counter (e.g., the method is terminated without authorizing re-provision of the dipeptidyl peptidase-4 inhibitor pharmaceutical composition to the subject).

Referring to blocks 448-449 in FIG. 4G, in some embodiments the third plurality of filters includes a ketoacidosis symptom filter. In some embodiments, the ketoacidosis filter is configured to be fired at least when the second plurality of survey results indicates that the subject has developed ketoacidosis since receiving their last provision of the dipeptidyl peptidase-4 inhibitor pharmaceutical composition. In some embodiments, the second plurality of survey results indicates that the subject has developed ketoacidosis when the second plurality of survey results indicate that the subject has been diagnosed with ketoacidosis since receiving their last provision of the dipeptidyl peptidase-4 inhibitor pharmaceutical composition. In some embodiments, the second plurality of survey results indicates that the subject has developed ketoacidosis when the second plurality of survey results indicate that the subject has experienced a symptom (e.g., a new and/or worsening symptom) of ketoacidosis since receiving their last provision of the dipeptidyl peptidase-4 inhibitor pharmaceutical composition, e.g., an increase of ketones in the blood of the subject, an increase of ketones in the urine of the subject, nausea, tiredness, vomiting, trouble breathing, and/or stomach pain including in the abdominal area. When the ketoacidosis filter is fired, the subject is not permitted to obtain the dipeptidyl peptidase-4 inhibitor pharmaceutical composition over-the-counter (e.g., the method is terminated without authorizing re-provision of the dipeptidyl peptidase-4 inhibitor pharmaceutical composition to the subject).

Referring to block 450 in FIG. 4G, in some embodiments the third plurality of filters includes a skin problem filter. In some embodiments, the second plurality of survey results indicates that the subject has developed ketoacidosis when the second plurality of survey results indicate that the subject has been diagnosed with blistering or an exfoliative skin condition since receiving their last provision of the dipeptidyl peptidase-4 inhibitor pharmaceutical composition. In some embodiments, the skin problem filter is configured to be fired at least when the second plurality of survey results indicates that the subject has experienced blistering or an exfoliative skin condition since receiving their last provision of the dipeptidyl peptidase-4 inhibitor pharmaceutical composition. When the skin problem filter is fired, the subject is not permitted to obtain the dipeptidyl peptidase-4 inhibitor pharmaceutical composition over-the-counter (e.g., the method is terminated without authorizing re-provision of the dipeptidyl peptidase-4 inhibitor pharmaceutical composition to the subject).

Referring to block 451 in FIG. 4G, in some embodiments the third plurality of filters includes a stomach pain filter. In some embodiments, the stomach pain filter is configured to be fired at least when the second plurality of survey results indicates that the subject has experienced stomach pain since receiving their last provision of the dipeptidyl peptidase-4 inhibitor pharmaceutical composition. When the stomach pain filter is fired, the subject is not permitted to obtain the dipeptidyl peptidase-4 inhibitor pharmaceutical composition over-the-counter (e.g., the method is terminated without authorizing re-provision of the dipeptidyl peptidase-4 inhibitor pharmaceutical composition to the subject).

Referring to block 452 in FIG. 4G, in some embodiments the third plurality of filters includes a joint pain filter. In some embodiments, the joint pain filter is configured to be fired at least when the second plurality of survey results indicates that the subject has experienced joint pain since receiving their last provision of the dipeptidyl peptidase-4 inhibitor pharmaceutical composition. When the joint pain filter is fired, the subject is not permitted to obtain the dipeptidyl peptidase-4 inhibitor pharmaceutical composition over-the-counter (e.g., the method is terminated without authorizing re-provision of the dipeptidyl peptidase-4 inhibitor pharmaceutical composition to the subject).

Referring to blocks 453-454 in FIG. 4G, in some embodiments, the third plurality of filters includes a blood sugar maintenance filter. In some embodiments, the blood sugar maintenance filter is configured to be fired at least when the second plurality of survey results indicate that administration of the dipeptidyl peptidase-4 inhibitor pharmaceutical composition is not providing a sufficient therapeutic effect, e.g., the subject's blood sugar levels are above a blood sugar maintenance threshold (e.g., a second blood sugar ceiling level). In some embodiments, the blood sugar maintenance threshold is selected from a level of from 6.5% to 7.0% glycated hemoglobin. In some embodiments, the blood sugar maintenance threshold is 7% glycated hemoglobin. When the blood sugar filter is fired, the subject is not permitted to obtain the metformin pharmaceutical composition over-the-counter (e.g., the method is terminated without authorizing re-provision of the metformin pharmaceutical composition to the subject).

In some embodiments, the blood sugar maintenance filter is only fired if a threshold amount of time has passed since the subject started taking the dipeptidyl peptidase-4 inhibitor pharmaceutical composition, e.g., to allow time for the blood sugar-lowering effects of the composition to occur before determining whether the composition is working effectively, or a threshold amount of time has passed since the subject last reported a status of their blood sugar level (e.g., in connection with a qualification or re-qualification for a provision of the metformin pharmaceutical composition), e.g., to avoid stopping the subject's use of the drug due to short-term fluctuations in the subject's blood sugar level. In some embodiments, the device does not run the blood sugar maintenance filter (e.g., apply one or more survey results), or query the user to provide an indication of their blood sugar level, when a predetermined period of time has not passed. For example, in some embodiments, the device determines whether the user received their first provision of the dipeptidyl peptidase-4 inhibitor pharmaceutical composition within a first threshold amount of time (e.g., in the past 2, 3, 4, 5, or 6 months) and/or whether the user reported an indication of their blood sugar level within a second threshold period of time (e.g., where their last provision of the dipeptidyl peptidase-4 inhibitor pharmaceutical composition was not their first provision of the composition). In some embodiments, the first threshold amount of time, e.g., since the user received their first provision of the dipeptidyl peptidase-4 inhibitor pharmaceutical composition, is three months. In some embodiments, the second threshold period of time, e.g., since the user last reported a provision of the dipeptidyl peptidase-4 inhibitor pharmaceutical composition, is six months. In some embodiments, the first and/or second threshold amount of time are independently one of one, two, three, four, five, six, seven, eight, nine, ten, eleven, twelve months, or more.

In some embodiments, the device accounts for gaps in the subject's use of the metformin pharmaceutical composition when determining whether the subject's blood sugar is being effectively managed by administration of the composition (e.g., in some embodiments, where the device determines that the user has been without a provision of the metformin pharmaceutical composition for a threshold period of time, the device bypasses the blood sugar maintenance filter, or relaxes the requirements of the filter, for example, to a blood sugar level below that of the first ceiling blood sugar level).

Referring to block 469 in FIG. 4I, in some embodiments (e.g., where the dipeptidyl peptidase-4 inhibitor pharmaceutical composition includes saxagliptin or alogliptin), the third plurality of filters includes a heart failure filter. In some embodiments, the heart failure filter is configured to be fired at least when the second plurality of survey results indicates that the subject has developed heart since receiving their last provision of the dipeptidyl peptidase-4 inhibitor pharmaceutical composition. In some embodiments, the second plurality of survey results indicates that the subject has developed heart failure when the second plurality of survey results indicate that the subject has been diagnosed with heart failure since receiving their last provision of the dipeptidyl peptidase-4 inhibitor pharmaceutical composition. In some embodiments, the second plurality of survey results indicates that the subject has developed heart failure when the second plurality of survey results indicate that the subject has experienced a symptom (e.g., a new and/or worsening symptom) of heart failure since receiving their last provision of the dipeptidyl peptidase-4 inhibitor pharmaceutical composition, e.g., increased shortness of breath, trouble breathing, a rapid increase in weight, swelling of the feet, swelling of the ankles, and swelling of the legs. When the heart failure filter is fired, the subject is not permitted to obtain the dipeptidyl peptidase-4 inhibitor pharmaceutical composition over-the-counter (e.g., the method is terminated without authorizing re-provision of the dipeptidyl peptidase-4 inhibitor pharmaceutical composition to the subject).

Figure 8A:
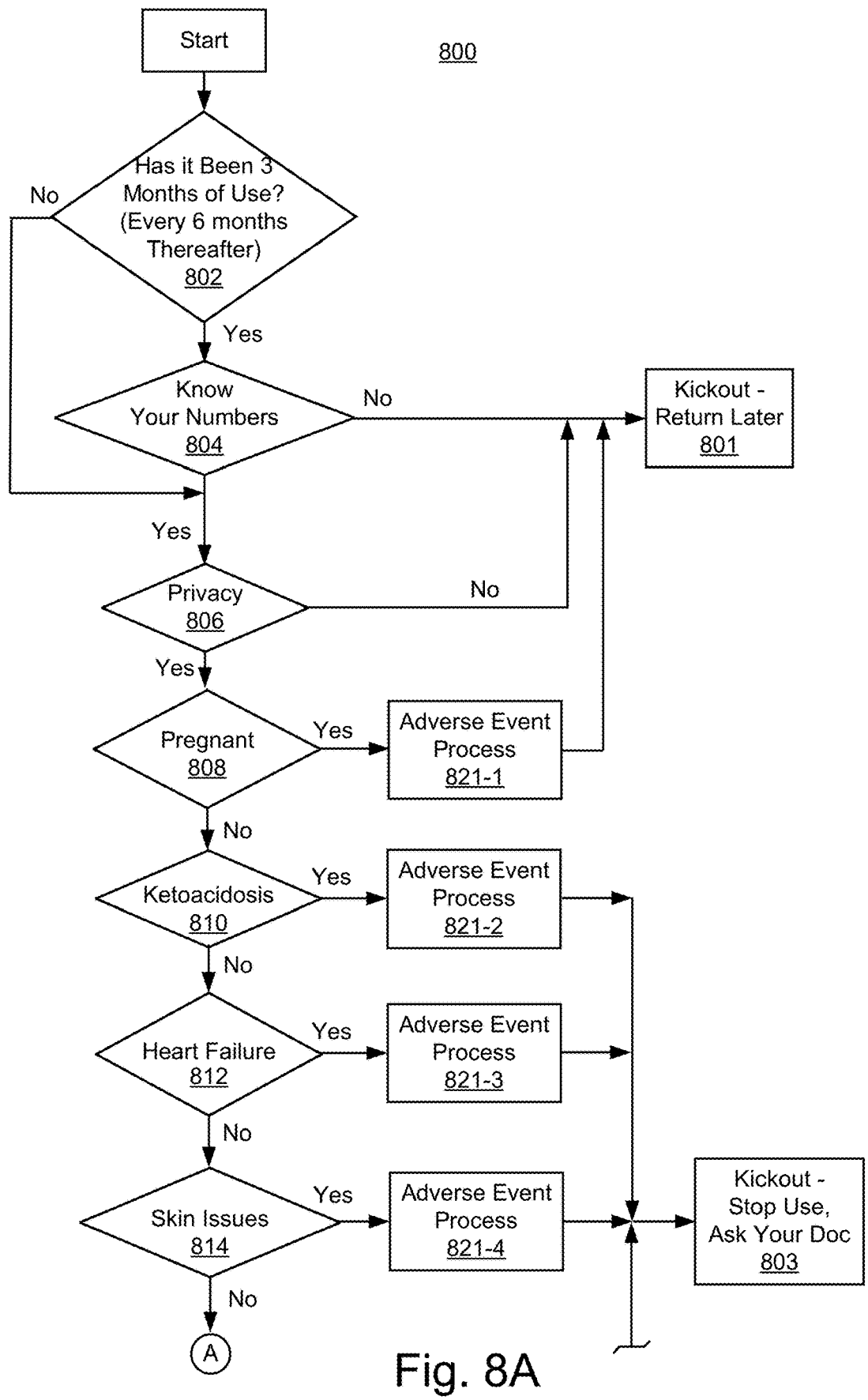
FIGS. 8A, 8B, and 8C collectively illustrate an example method for qualifying a subject for a refill of an over-the-counter dipeptidyl peptidase-4 inhibitor pharmaceutical composition, in accordance with an embodiment of the present disclosure.
Figure 8B:
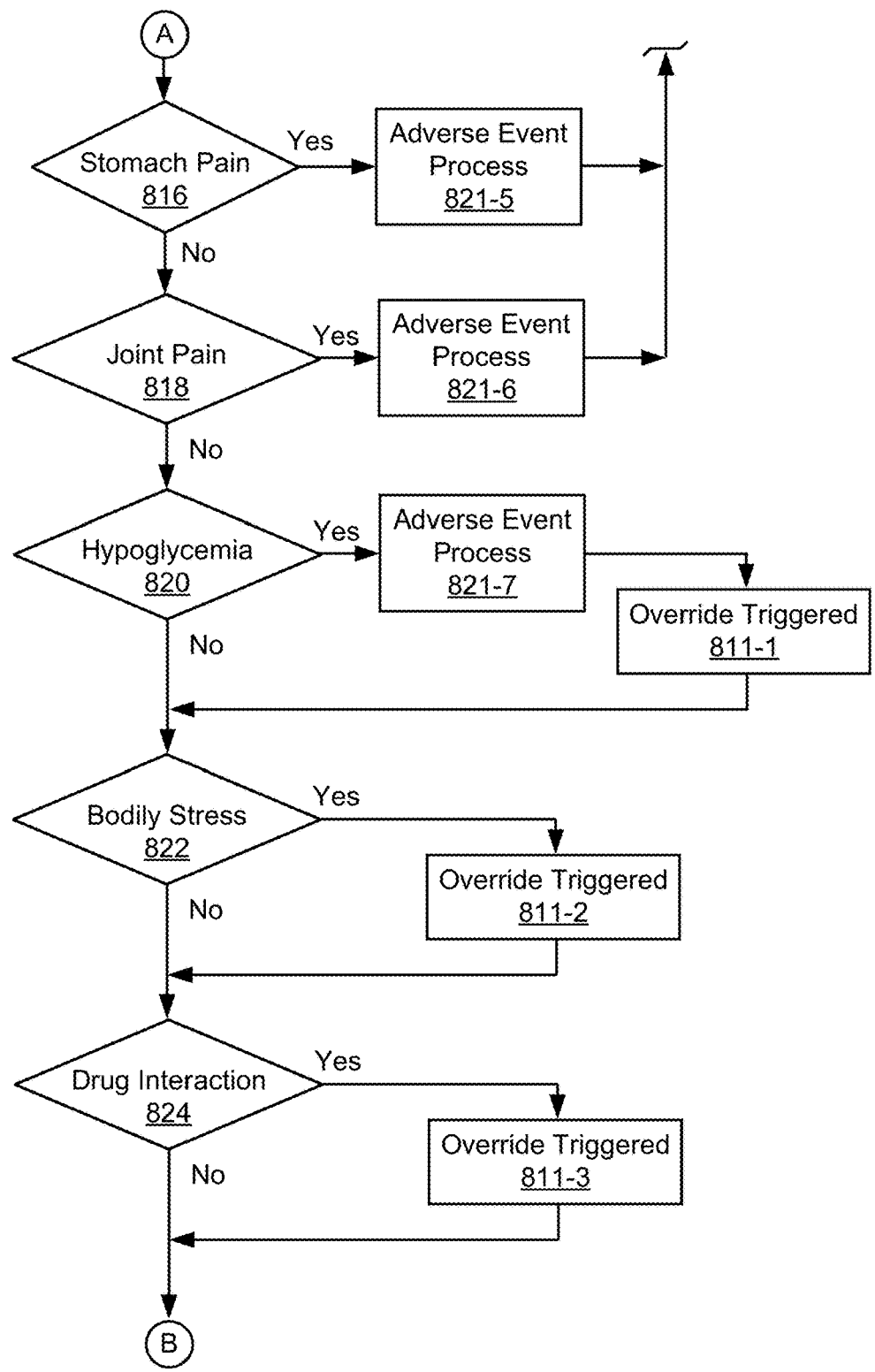
Figure 8C:
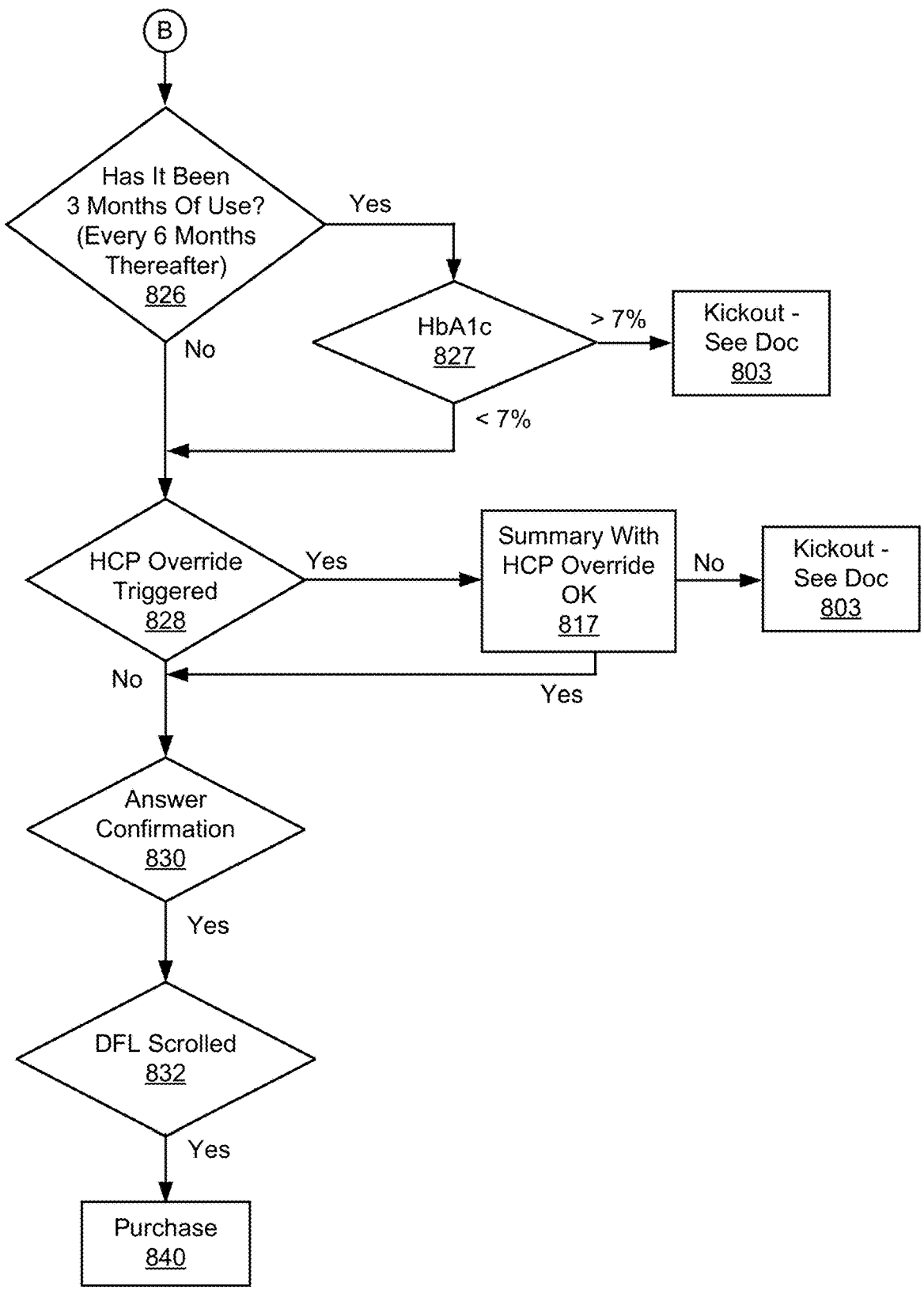

Referring to blocks 456-462 in FIG. 4H, the method also includes running all or a portion of the second survey results against a fourth plurality of filters of the second category class 220-2. When a respective filter in the fourth plurality of filters is fired, the subject is provided with a warning corresponding to the respective filter. In some embodiments, the warning is provided as a next step, e.g., prior to applying survey results to any subsequent filters, after the corresponding filter is fired. For example, with respect to FIGS. 8A-8C, in some embodiments, when the bodily stress filter is triggered at 822, the device would provide the subject with a warning prior to proceeding to the drug interaction filter at 824, e.g., requiring the subject confirm they have discussed their bodily stress with a health care professional, e.g., and the healthcare professional still recommends taking a dipeptidyl peptidase-4 inhibitor pharmaceutical composition. In some embodiments the warning is provided after applying survey results to all subsequent filters. For example, in some embodiments, when the bodily stress filter is triggered at

822, the device proceeds to the drug interaction filter at 824 prior to transmitting a warning to the subject, and transmits all warnings corresponding to filters of the second category class, at 817, after survey results have been applied to all subsequent filters.

In some embodiments, the fourth plurality of filters of the second category class 220-2 includes some or all of the filters listed in Table 6. For example, in some embodiments, the fourth plurality of filters includes 2, 3, or all 4 of the filters listed in Table 6. In one embodiment, the fourth plurality of filters includes at least filters 1-3, as listed in Table 6.

TABLE 6

Example filters for risk factors associated with qualifying a subject for an over-the-counter provision of a dipeptidyl peptidase-4 inhibitor pharmaceutical composition

| Filter | Example Criteria |
| --- | --- |
| 1a | a hypoglycemia filter |
| 2a | a bodily stress filter |
| 3a | a drug interaction filter |
| 4a | a side effect filter |

In one embodiment, the fourth plurality of filters includes at least filters 1a-3a as provided in Table 6. It is contemplated that, in some embodiments, any one or more of the filters provided in Table 6 will not be included in the fourth plurality of filters. For example, in some embodiments, a characteristic associated with a particular survey result will be informative when qualifying a subject for one particular dipeptidyl peptidase-4 inhibitor pharmaceutical composition but not for another dipeptidyl peptidase-4 inhibitor pharmaceutical composition. Accordingly, it is contemplated that the fourth plurality of filters includes any sub-set of filters provided in Table 6. Likewise, the skilled artisan may know of other filters, not provided in Table 6, that may be combined with any subset of the filters 222 provided in Table 6 to form the fourth plurality of filters results used in the methods described herein.

Referring to blocks 457-458 in FIG. 4H, in some embodiments, the fourth plurality of filters includes a hypoglycemia filter. In some embodiments, the hypoglycemia symptom filter is configured to be fired at least when the second plurality of survey results indicates that the subject has developed hypoglycemia since receiving their last provision of the dipeptidyl peptidase-4 inhibitor pharmaceutical composition. In some embodiments, the second plurality of survey results indicates that the subject has developed hypoglycemia when the survey results indicate that the subject has been diagnosed with hypoglycemia since receiving their last provision of the dipeptidyl peptidase-4 inhibitor pharmaceutical composition. In some embodiments, the second plurality of survey results indicates that the subject has developed hypoglycemia when the survey results indicate that the subject has experienced a symptom (e.g., a new and/or worsening symptom) of hypoglycemia, e.g., shaking, sweating, rapid heartbeat, change in vision, hunger, headaches, and/or a change in mood.

Referring to blocks 459-460 in FIG. 4H, in some embodiments, the fourth plurality of filters includes a bodily stress filter. In some embodiments, the bodily stress filter is configured to be fired at least when the second plurality of survey results indicates that the subject is experiencing a bodily stress. A bodily stress, which is capable of firing the bodily stress filter, is selected from the group consisting of fever, a recent trauma, an infection, and a recent surgery.

Referring to blocks 461-462 in FIG. 4H, in some embodiments, the fourth plurality of filters includes a drug interaction filter. In some embodiments, the second drug interaction filter is configured to be fired at least when the second plurality of survey results indicates that the subject has begun taking a medication that interacts with the dipeptidyl peptidase-4 inhibitor pharmaceutical composition, since receiving their last provision of the dipeptidyl peptidase-4 inhibitor pharmaceutical composition. A medication that interacts with the dipeptidyl peptidase-4 inhibitor pharmaceutical composition, which is capable of firing the drug interaction filter, is selected from the group consisting of an HIV medication, an AIDS medication, an antifungal medication, an antibiotic, or a medication for diabetes. Example drugs that interact with various dipeptidyl peptidase-4 inhibitors are outlined above, with reference to the drug interaction filter applied during an initial qualification of the subject.

Referring to block 464 in FIG. 4I, in some embodiments the method also includes obtaining acknowledgment from the subject for each warning issued to the subject by any filter in the fourth plurality of filters. As described with respect to the warnings issued in conjunction with the second plurality of filters of the second category class, in some embodiments, the warning includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a dipeptidyl peptidase-4 inhibitor pharmaceutical composition in view of the underlying risk factor. Accordingly, acknowledgement is obtained from the subject when the subject indicates that they have discussed the risk factor underlying the respective filter in the fourth plurality of filters that was fired with a health care professional.

Referring to blocks 466-467 in FIG. 4I, in some embodiments when a respective filter in the third plurality of filters or fourth plurality of filters is fired, a record associated with the firing of the respective filter is stored (e.g., memorializing an adverse event that is required to be reported to a regulatory agency). This record is stored in an adverse event module 242 which includes records of filter firing events associated with a plurality of subjects (e.g., an aggregation of adverse events associated with the dipeptidyl peptidase-4 inhibitor pharmaceutical composition across a population of subjects taking the dipeptidyl peptidase-4 inhibitor pharmaceutical composition over-the-counter). In some embodiments, a record of an adverse event is generated upon firing of one or more of a pregnancy filter, a ketoacidosis filter, a heart failure filter, a skin issue filter, a stomach pain filter, a join pain filter, or a hypoglycemia filter, as applied during a re-qualification of a subject. In some embodiments, an indication pf the adverse event is communicated to a third party (e.g., a medical practitioner associated with the subject, a health care professional of the subject, and/or a manufacturer/promoter of the dipeptidyl peptidase-4 inhibitor pharmaceutical composition). In some embodiments, the indication is automatically stored in the adverse event module 242 when submitted by a subject as part of the second survey.

Referring to block 466 in FIG. 4I, in some embodiments the procedure further includes proceeding with the re-fulfillment process when the re-fulfillment process is not already terminated by the firing of a filter in the third plurality of filters (e.g., the second pregnancy filter). In order for the re-fulfillment process to complete the subject is required to acknowledge each warning associated with each filter 222 in the fourth plurality of filters that was fired.

Referring to block 467 in FIG. 4I, in some embodiments the re-fulfillment process also includes storing an indication in the subject profile 232 of the subject of a re-order for the dipeptidyl peptidase-4 inhibitor pharmaceutical composition. The re-fulfillment process further includes communicating an over-the-counter drug facts label 230 for the dipeptidyl peptidase-4 inhibitor pharmaceutical composition to the subject. As previously described, the communication of the over-the-counter drug facts label 230 can occur in a variety of means. Upon confirmation from the subject that the over-the-counter drug facts label 230 has been received and read, the method includes authorizing a re-order provision of the dipeptidyl peptidase-4 inhibitor pharmaceutical composition to the subject. In some embodiments, this re-order provision includes the destination of the subject.

Referring to block 468 in FIG. 4I, in some embodiments, the second plurality of survey results further includes whether the subject has experienced a side effect from the dipeptidyl peptidase-4 inhibitor pharmaceutical composition since receiving their last provision of the dipeptidyl peptidase-4 inhibitor pharmaceutical composition, and the fourth plurality of filters further includes a side effect filter that is fired at least when the second plurality of survey results indicates that the subject has experienced a side effect of the dipeptidyl peptidase-4 inhibitor pharmaceutical composition. A side effect that is capable of firing the side effect filter is selected from the group consisting of an upper respiratory tract infection, a urinary tract infection, and headaches.

FIG. 7 illustrates an example method (700) (e.g., performed at an electric device 102 or 250) for qualifying a subject for an over-the-counter dipeptidyl peptidase-4 inhibitor pharmaceutical composition (e.g., containing saxagliptin or alogliptin). In some embodiments, the method of FIG. 7 is utilized when the subject has not been previously qualified for the dipeptidyl peptidase-4 inhibitor pharmaceutical composition. In some embodiments, the method of FIG. 7 is utilized when the subject was previously qualified for the dipeptidyl peptidase-4 inhibitor pharmaceutical composition but a predetermined period of time elapsed since the previous qualification occurred (e.g., the most recent qualification/re-qualification of the subject was greater than one year ago).

Referring to FIG. 7, the device prompts (702) the subject to acknowledge a privacy notice. Since the present disclosure requires the subject to know and input sensitive medical information (e.g., information only the subject and a medical practitioner have access to), privacy of this information is important. Once the subject has acknowledged they have the requisite privacy for continuing, the device prompts (704) the user to confirm that they know their blood sugar levels (e.g., because the subject must know their blood values in order to complete the qualification process). If the subject indicates they do not know their blood sugar level, the process terminates 701 without authorizing a provision of the dipeptidyl peptidase-4 inhibitor pharmaceutical composition, and optionally transmits advice to the user to return later, e.g., once they know their blood sugar levels. In some embodiments, the device does not prompt the user to confirm they know their numbers, but includes a selection for indicating they don't know a value when asking the subject for a particular value.

If the subject indicates they know their blood sugar levels, the device prompts the subject to provide information about their pregnancy status and applies (706) the answer received from the subject to a pregnancy filter. When the pregnancy filter is fired (e.g., when the answer indicates the subject is pregnant, breastfeeding, or planning to become pregnant), the device terminates (703) the qualification process without authorizing a provision of the dipeptidyl peptidase-4 inhibitor pharmaceutical composition and, optionally, transmits advice to the user as to why they should not take the dipeptidyl peptidase-4 inhibitor pharmaceutical composition.

When the pregnancy filter is not fired, the device proceeds with the qualification process, prompting the subject to indicate whether they have type 1 diabetes and applies (708) the answer received from the subject to a type 1 diabetes filter. When the type 1 diabetes filter is fired (e.g., when the answer indicates the subject has type 1 diabetes), the device terminates (703) the qualification process without authorizing a provision of the dipeptidyl peptidase-4 inhibitor pharmaceutical composition and, optionally, transmits advice to the user as to why they should not take the dipeptidyl peptidase-4 inhibitor pharmaceutical composition.

When the type 1 diabetes filter is not fired, the device proceeds with the qualification process, prompting the subject to indicate whether they have ketoacidosis and applies (710) the answer received from the subject to a ketoacidosis filter. When the ketoacidosis filter is fired (e.g., when the answer indicates the subject has ketoacidosis), the device terminates (703) the qualification process without authorizing provision of the dipeptidyl peptidase-4 inhibitor pharmaceutical composition and, optionally, transmits advice to the user as to why they should not take the dipeptidyl peptidase-4 inhibitor pharmaceutical composition.

When the ketoacidosis filter is not fired, the device proceeds with the qualification process, prompting the subject to provide information about their age (712). When the age filter is fired (e.g., when the answer to the prompt indicates the subject is younger than eighteen years old) the device terminates (703) the qualification process without authorizing provision of the dipeptidyl peptidase-4 inhibitor pharmaceutical composition and, optionally, transmits advice to the user as to why they should not take the dipeptidyl peptidase-4 inhibitor pharmaceutical composition and/or to return once they have obtained an age at which it would be appropriate to take a dipeptidyl peptidase-4 inhibitor pharmaceutical composition.

When the age filter is not fired, the device proceeds with the qualification process, prompting the subject to provide their blood sugar level status and applies (714) the answer received from the subject to a blood sugar filter. When the blood sugar filter is fired (e.g., when the answer to the prompt indicates the subject has a blood sugar level that is either too low (e.g., below a pre-diabetic and/or diabetic level, e.g., less than 6.5% glycated hemoglobin) or too high (e.g., above a threshold at which a stronger, prescription medication would be more appropriate, e.g., greater than 7.5% glycated hemoglobin)), the device terminates (703) the qualification process without authorizing provision of the dipeptidyl peptidase-4 inhibitor pharmaceutical composition and, optionally, transmits advice to the user as to why they should not take the dipeptidyl peptidase-4 inhibitor pharmaceutical composition (e.g., because they do not need blood lowering medication or because they need a stronger, prescription medication).

When the blood sugar filter is not fired, the device proceeds with the qualification process, prompting the subject to indicate whether they have heart failure and applies (716) the answer received from the subject to a heart failure filter. When the heart failure filter is fired (e.g., when the answer indicates the subject has had heart failure), an override procedure (711-1) is initiated (e.g., the device creates a record indicating that the user must confirm they have discussed taking a dipeptidyl peptidase-4 inhibitor pharmaceutical composition with a health care professional).

The device proceeds with the qualification process, prompting the subject to indicate whether they have ever had a pancreatic problem and applies (718) the answer received from the subject to a pancreatic disease filter. When the pancreatic disease filter is fired (e.g., when the answer indicates the subject has had pancreatitis), an override procedure (711-2) is initiated (e.g., the device creates a record indicating that the user must confirm they have discussed taking a dipeptidyl peptidase-4 inhibitor pharmaceutical composition with a health care professional).

The device proceeds with the qualification process, prompting the subject to indicate their alcohol consumption status and applies (720) the answer received from the subject to an alcohol consumption filter. When the alcohol consumption filter is fired (e.g., when the answer indicates the subject abuses alcohol), an override procedure (711-3) is initiated (e.g., the device creates a record indicating that the user must confirm they have discussed taking a dipeptidyl peptidase-4 inhibitor pharmaceutical composition with a health care professional).

The device proceeds with the qualification process, prompting the subject to indicate their gallstone status and applies (722) the answer received from the subject to a gallstone filter. When the gallstone filter is fired (e.g., when the answer indicates the subject has had a gallstone), an override procedure (711-4) is initiated (e.g., the device creates a record indicating that the user must confirm they have discussed taking a dipeptidyl peptidase-4 inhibitor pharmaceutical composition with a health care professional).

The device proceeds with the qualification process, prompting the subject to indicate their triglyceride level and applies (724) the answer received from the subject to a triglyceride filter. When the triglyceride filter is fired (e.g., when the answer indicates the subject has had a high triglyceride level), an override procedure (711-5) is initiated (e.g., the device creates a record indicating that the user must confirm they have discussed taking a dipeptidyl peptidase-4 inhibitor pharmaceutical composition with a health care professional).

The device proceeds with the qualification process, prompting the subject to indicate whether they are taking a medication that interacts with the dipeptidyl peptidase-4 inhibitor pharmaceutical composition and applies (726) the answer received from the subject to a first drug interaction filter. When the first drug interaction filter is fired (e.g., when the answer indicates the subject are taking a medication that interacts with the dipeptidyl peptidase-4 inhibitor pharmaceutical composition), an override procedure (711-6) is initiated (e.g., the device creates a record indicating that the user must confirm they have discussed taking a dipeptidyl peptidase-4 inhibitor pharmaceutical composition with a health care professional).

The device proceeds with the qualification process, determining (728) whether the override procedure has been triggered (e.g., by firing of any one of the heart failure filter, pancreatic disease filter, the alcohol consumption filter, the gallstone filter, the triglyceride filter, or the first drug interaction filter). If the override procedure was triggered, the device prompts (717) the user to confirm that they have spoken with a medical professional about taking a dipeptidyl peptidase-4 inhibitor pharmaceutical composition (e.g., in view of the underlying risk factor that triggered the heart failure, pancreatic disease, alcohol consumption, gallstone, triglyceride, and/or drug interaction filter(s)), e.g., and the medical professional recommended (or did not advise against) taking the dipeptidyl peptidase-4 inhibitor pharmaceutical composition. If the user's response indicates they have not spoken with a medical professional or the medical professional did not recommend taking the dipeptidyl peptidase-4 inhibitor pharmaceutical composition, the device terminates (705) the process and, optionally, transmits advice for the subject to consult a medical professional If the override procedure was not triggered, or the override procedure was triggered and the subject's response (717) indicates that they discussed taking a dipeptidyl peptidase-4 inhibitor pharmaceutical composition with a medical professional (e.g., in view of the underlying risk factor triggering the override procedure), e.g., and the medical professional recommended taking (or did not advise against) a dipeptidyl peptidase-4 inhibitor pharmaceutical composition, the device proceeds with the qualification process, prompting (730) the subject to confirm their answers. If the user confirms their answers, the device transmits (732) a drug facts label for the dipeptidyl peptidase-4 inhibitor pharmaceutical composition and prompts the user to read the drug facts label. If the subject confirms they have read the drug facts label (and/or the device determines the user scrolled through the drug facts label), the device proceeds to authorize (740) purchase of the dipeptidyl peptidase-4 inhibitor pharmaceutical composition.

FIG. 8 illustrates an example method (800) for qualifying a subject for a refill of an over-the-counter dipeptidyl peptidase-4 inhibitor pharmaceutical composition (e.g., containing saxagliptin or alogliptin), e.g., following a prescription from a medical professional or initial qualification by a method described herein. Referring to FIG. 8, when the device determines (802) that it has been at least three months since the user first received a provision of the dipeptidyl peptidase-4 inhibitor pharmaceutical composition, the device prompts (804) the user to confirm that they know their blood sugar levels (e.g., because the subject must know their blood values in order to complete the qualification process). If the subject indicates they do not know their blood sugar level, the process terminates (801) without authorizing provision of the dipeptidyl peptidase-4 inhibitor pharmaceutical composition, and optionally transmits advice to the user to return later, e.g., once they know their blood sugar levels. In some embodiments, e.g., where the user has recently begun taking the metformin pharmaceutical compound and/or the device has access to a recent a blood sugar measurement from the subject, the device bypasses prompting the user to confirm that they know their blood sugar levels. When the subject indicates they know their blood sugar levels, the process continues, prompting (806) the subject to acknowledge a privacy notice. If the subject indicates they do not have privacy, the process terminates (801) without authorizing provision of the dipeptidyl peptidase-4 inhibitor pharmaceutical composition, and optionally transmits advice to the user to return later (e.g., when they have adequate privacy).

Once the subject has acknowledged they have the requisite privacy for continuing, the device prompts the subject to provide information about their pregnancy status and applies (808) the answer received from the subject to a pregnancy filter. When the pregnancy filter is fired (e.g., when the answer indicates the subject is pregnant, breastfeeding, or planning to become pregnant), the device creates (821-1) a record of an adverse event (e.g., aggregated in an adverse event data store having records of adverse events from a plurality of users), terminates (801) the qualification process and, optionally, transmits advice to the user as to why they should not take the dipeptidyl peptidase-4 inhibitor pharmaceutical composition and/or to return once they are not pregnant, breastfeeding, or planning on becoming pregnant.

When the pregnancy filter is not fired, the device proceeds with the qualification process, prompting the subject to provide information indicating whether they have developed ketoacidosis and applies (810) the answer to a ketoacidosis symptom filter. When the ketoacidosis symptom filter is fired (e.g., when the subject's answer indicates the subject has developed ketoacidosis since receiving their last provision of the dipeptidyl peptidase-4 inhibitor pharmaceutical composition), the device creates (821-2) a record of an adverse event (e.g., aggregated in an adverse event data store having records of adverse events from a plurality of users) and the device terminates (803) the qualification process, optionally transmitting advice for the subject to discuss taking a dipeptidyl peptidase-4 inhibitor pharmaceutical composition with a medical professional.

When the ketoacidosis symptom filter is not fired, the device proceeds with the qualification process, prompting the subject to provide information indicating whether they have developed heart failure and applies (812) the answer to a heart failure symptom filter. When the heart failure symptom filter is fired (e.g., when the subject's answer indicates the subject has developed heart failure since receiving their last provision of the dipeptidyl peptidase-4 inhibitor pharmaceutical composition), the device creates (821-3) a record of an adverse event (e.g., aggregated in an adverse event data store having records of adverse events from a plurality of users) and the device terminates (801) the qualification process, optionally transmitting advice for the subject to discuss taking dipeptidyl peptidase-4 inhibitor pharmaceutical composition with a medical professional.

When the heart failure symptom problem filter is not fired, the device proceeds with the qualification process, prompting the subject to provide information indicating whether they have experienced a skin problem and applies (814) the answer to a skin problem filter. When the skin problem filter is fired (e.g., when the subject's answer indicates the subject has experienced blistering or an exfoliative skin condition since receiving their last provision of the dipeptidyl peptidase-4 inhibitor pharmaceutical composition), the device creates (821-4) a record of an adverse event (e.g., aggregated in an adverse event data store having records of adverse events from a plurality of users) and the device terminates (801) the qualification process, optionally transmitting advice for the subject to discuss taking dipeptidyl peptidase-4 inhibitor pharmaceutical composition with a medical professional.

When the skin problem filter is not fired, the device proceeds with the qualification process, prompting the subject to provide information indicating whether they have experienced stomach pain and applies (816) the answer to a stomach pain filter. When the stomach pain filter is fired (e.g., when the subject's answer indicates the subject has experienced stomach pain since receiving their last provision of the dipeptidyl peptidase-4 inhibitor pharmaceutical composition), the device creates (821-5) a record of an adverse event (e.g., aggregated in an adverse event data store having records of adverse events from a plurality of users) and the device terminates (801) the qualification process, optionally transmitting advice for the subject to discuss taking dipeptidyl peptidase-4 inhibitor pharmaceutical composition with a medical professional.

When the stomach pain filter is not fired, the device proceeds with the qualification process, prompting the subject to provide information indicating whether they have experienced joint pain and applies (818) the answer received from the subject to a joint pain filter. When the joint pain filter is fired (e.g., when the answer indicates the subject has experienced joint pain since receiving their last provision of the dipeptidyl peptidase-4 inhibitor pharmaceutical composition), the device creates (821-6) a record of an adverse event (e.g., aggregated in an adverse event data store having records of adverse events from a plurality of users) and the device terminates (801) the qualification process, optionally transmitting advice for the subject to discuss taking dipeptidyl peptidase-4 inhibitor pharmaceutical composition with a medical professional.

When the joint pain filter is not fired, the device proceeds with the qualification process, prompting the subject to provide information indicating whether they have developed hypoglycemia and applies (820) the answer received from the subject to hypoglycemia symptom filter. When the hypoglycemia symptom filter is fired (e.g., when the answer indicates the subject has developed hypoglycemia since receiving their last provision of the dipeptidyl peptidase-4 inhibitor pharmaceutical composition), the device creates (821-7) a record of an adverse event (e.g., aggregated in an adverse event data store having records of adverse events from a plurality of users) and initiates (811-1) an override procedure (e.g., creates a record indicating that the user must confirm they have discussed taking a dipeptidyl peptidase-4 inhibitor pharmaceutical composition with a health care professional).

The device proceeds with the qualification process, prompting the subject to provide information indicating their bodily stress status and applies (822) the answer received from the subject to a bodily stress filter. When the bodily stress filter is fired (e.g., when the answer indicates the subject is experiencing a bodily stress), the device initiates (811-2) an override procedure (e.g., creates a record indicating that the user must confirm they have discussed taking a dipeptidyl peptidase-4 inhibitor pharmaceutical composition with a health care professional).

The device proceeds with the qualification process, prompting the subject to indicate whether they are taking a medication that interacts with the dipeptidyl peptidase-4 inhibitor pharmaceutical composition and applies (824) the answer received from the subject to a second drug interaction filter. When the second drug interaction filter is fired (e.g., when the answer indicates the subject has begun taking a medication that interacts with the dipeptidyl peptidase-4 inhibitor pharmaceutical composition since receiving their last provision of the dipeptidyl peptidase-4 inhibitor pharmaceutical composition), the device initiates (811-3) an override procedure (e.g., creates a record indicating that the user must confirm they have discussed taking a dipeptidyl peptidase-4 inhibitor pharmaceutical composition with a health care professional).

The device proceeds with the qualification process, determining whether the subject has been taking the dipeptidyl peptidase-4 inhibitor pharmaceutical composition for at least a threshold amount of time (e.g., at least three months since receiving their first provision of the dipeptidyl peptidase-4 inhibitor pharmaceutical composition and every six months thereafter), e.g., without providing a blood sugar level. If the device determines that a threshold amount of time has passed (e.g., since a last stored blood sugar level measurement), the device prompts the subject to provide information about their blood sugar level (e.g., an actual value or whether it is below a threshold level) and applies (827) the answer received from the subject to a blood sugar filter. When the blood sugar filter is fired (e.g., when the answer indicates that the subject has a blood sugar level above a threshold level, e.g., 7% glycated hemoglobin) the device terminates (803) the qualification process and, optionally, transmits advice to the user to seek medical attention.

The device proceeds with the qualification process, determining (828) whether the override procedure has been triggered (e.g., by firing of any one of the hypoglycemia, bodily stress, and/or drug interaction filter(s)). If the override procedure has been triggered, the device prompts (817) the subject to confirm that they have spoken with a medical professional about taking a dipeptidyl peptidase-4 inhibitor pharmaceutical composition (e.g., in view of the underlying risk factor triggering the override procedure), e.g., and the medical professional recommended (or did not advise against) taking the dipeptidyl peptidase-4 inhibitor pharmaceutical composition. If the user's response indicates they have not spoken with a medical professional or the medical professional did not recommend taking the dipeptidyl peptidase-4 inhibitor pharmaceutical composition, the device terminates (803) the process and, optionally, transmits advice for the subject to consult a medical professional.

If the override procedure was not triggered, or the override procedure was triggered and the subject's response (817) indicated that the subject spoke with a medical professional, e.g., who recommended, or did not advise against, taking a dipeptidyl peptidase-4 inhibitor pharmaceutical composition (e.g., in view of the underlying risk factor triggering the override procedure), the device proceeds with the qualification process, prompting (830) the subject to confirm their answers. If the user confirms their answers, the device transmits (832) a drug facts label for the dipeptidyl peptidase-4 inhibitor pharmaceutical composition and prompts the user to read the drug facts label. If the subject confirms they have read and/or scrolled the drug facts label, the device proceeds to authorize (840) purchase of the dipeptidyl peptidase-4 inhibitor pharmaceutical composition.

Specific Embodiments

In one aspect, the disclosure provides methods, software, and computer systems for qualifying a human subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels. In one embodiment, a computer system (e.g., computer system 250 in FIG. 2) includes instructions for conducting a survey of the subject (e.g., including survey questions 208 and 212 administered via assessment module 252 in FIG. 2) to obtain information about the subject necessary to run against at least two series of filters (e.g., filters 216 and 222 in first filter category class 214-1 and second filter category class 220-1, respectively, in FIG. 2). The computer system also includes instructions for running the survey results against the filters. Filters 216 in the first series of filters 214 prevent authorization of a provision of the OTC dipeptidyl peptidase-4 inhibitor where the subject's survey results identify a contraindication for the OTC dipeptidyl peptidase-4 inhibitor. Filters 222 in the second series of filters 220 generate a warning 226 where the subject's survey results identify a risk factor for the OTC dipeptidyl peptidase-4 inhibitor. In some embodiments, the warning 226 includes a prompt requiring the subject to confirm they have discussed the risk factor with a physician in order to proceed with qualification for the OTC dipeptidyl peptidase-4 inhibitor.

In one aspect, the disclosure provides methods, software, and computer systems for re-qualifying a human subject for over-the-counter delivery of a dipeptidyl peptidase-4 inhibitor pharmaceutical composition for lower blood sugar, e.g., thereby, treating diabetes. In one embodiment, a computer system (e.g., computer system 250 in FIG. 2) includes instructions for conducting a survey of the subject (e.g., administered via reassessment module 254 in FIG. 2) to obtain information about the subject necessary to run against at least two series of filters. The computer system also includes instructions for running the survey results against the filters. Filters 216 in the third series of filters 214-2 prevent authorization for delivery of the OTC dipeptidyl peptidase-4 inhibitor where the subject's survey results identify a contraindication for the OTC dipeptidyl peptidase-4 inhibitor. Filters 222 in the fourth series of filters 220-2 generate a warning 226 where the subject's survey results identify a risk factor for the OTC dipeptidyl peptidase-4 inhibitor. In some embodiments, the warning 226 includes a prompt requiring the subject to confirm they have discussed the risk factor with a physician in order to proceed with qualification for the OTC dipeptidyl peptidase-4 inhibitor.

In one aspect, the disclosure provides a computer system for qualifying a human subject for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels. The computer system comprising one or more processors and a memory, the memory comprising non-transitory instructions which, when executed by the one or more processor, perform a method for qualifying a human subject for over-the-counter delivery of the dipeptidyl peptidase-4 inhibitor pharmaceutical composition. The method includes conducting a first survey of the subject thereby obtaining a first plurality of survey results necessary to run against a first plurality of filters of a first category class and a second plurality of filters of a second category class. The method also includes running all or a portion of the first plurality of survey results against a first plurality of filters of a first category class, wherein, when a respective filter in the first plurality of filters is fired, the subject is deemed not qualified for delivery of the dipeptidyl peptidase-4 inhibitor pharmaceutical composition and the method is terminated without delivery of the dipeptidyl peptidase-4 inhibitor pharmaceutical composition to the subject. The method also includes running all or a portion of the first plurality of survey results against a second plurality of filters of a second category class, wherein, when a respective filter in the second plurality of filters is fired, the subject is provided with a warning corresponding to the respective filter. The method also includes obtaining acknowledgment from the subject for the warning issued to the subject by any filter in the second plurality of filters. The method also includes proceeding with a fulfillment process when no filter in the first plurality of filters has been fired and the subject has acknowledged each warning associated with each filter in the second plurality of filters that was fired. The fulfillment process includes: storing an indication in a subject profile of an initial order for the dipeptidyl peptidase-4 inhibitor pharmaceutical composition, communicating an over-the-counter drug facts label for the dipeptidyl peptidase-4 inhibitor pharmaceutical composition to the subject, and authorizing, upon confirmation from the subject that the over-the-counter drug facts label has been received and read, provision of the dipeptidyl peptidase-4 inhibitor pharmaceutical composition to the subject. In some embodiments, the authorization includes a destination associated with the subject. In some embodiments, the first plurality of survey results indicates a plurality of subject characterizations selected from those listed in Table 1. In one embodiment, the first plurality of survey results indicates: whether the subject is any one of (i) pregnant, (ii) breastfeeding, or (iii) planning to become pregnant, a Type 1 diabetes status of the subject, a ketoacidosis status of the subject, an age of the subject, a blood sugar level of the subject, whether the subject has ever had a pancreatic problem, an alcohol consumption status of the subject, whether the subject has ever had a gallstone, whether the subject has ever had high triglyceride levels, and whether the subject is taking a medication that interacts with the dipeptidyl peptidase-4 inhibitor pharmaceutical composition.

In some embodiments, the first plurality of filters includes a plurality of filters selected from the filters listed in Table 2. In one embodiment, the first plurality of filters includes a first pregnancy filter, a Type 1 diabetes, a ketoacidosis filter, an age filter, and a first blood sugar filter.

In some embodiments, the second plurality of filters includes a plurality of filters selected from the filters listed in Table 3. In one embodiment, the second plurality of filters includes a pancreatic disease filter, an alcohol consumption filter, a gallstone filter, a triglyceride filter, and a first diabetes medication filter.

In some embodiments, the first and second plurality of filters includes filters selected from the filters listed in Table 7. In some embodiments, the first plurality of filters of the first category class include a first sub-plurality of the filters listed in Table 7, for example, 2, 3, 4, 5, 6, 7, 8, 9, 10, 11, or all 12 of the filters listed in Table 7, and the second plurality of filters of the first category class include a second sub-plurality of the filters listed in Table 7, which is different from the first sub-plurality of filters, for example, 2, 3, 4, 5, 6, 7, 8, 9, 10, 11, or all 12 of the filters listed in Table 7. In some embodiments, each of the filters in the first sub-plurality of filters is different from each of the filters in the second sub-plurality of filters (e.g., no filter listed in Table 7 is included in both the first sub-plurality and the second sub-plurality of filters). In some embodiments, a system for qualifying a subject for delivery of an over-the-counter dipeptidyl peptidase-4 inhibitor pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 7, e.g., at least 2, 3, 4, 5, 6, 7, 8, 9, 10, 11, or all 12 of the filters listed in Table 7. In some embodiments, where a filter listed in Table 7 corresponds to a filter listed in Table 2 or Table 3, a threshold level sufficient to fire the corresponding filter listed in Table 2 or Table 3, as described in detail above, is sufficient to fire the filter listed in Table 7.

TABLE 7

Example filters for contraindications/risk factors associated with qualifying a subject for an over-the-counter provision of a dipeptidyl peptidase-4 inhibitor pharmaceutical composition

| Filter | Example Criteria |
|--------|------------------|
| 1b | a pregnancy filter |
| 2b | a Type 1 diabetes filter |
| 3b | a ketoacidosis filter |
| 4b | an age filter |
| 5b | a blood sugar filter |
| 6b | an adverse reaction filter |
| 7b | a pancreatic disease filter |
| 8b | an alcohol consumption filter |
| 9b | a gallstone filter |
| 10b | a triglyceride filter |
| 11b | a drug interaction filter |
| 12b | a heart failure filter |

In one aspect, the disclosure provides methods, software, and computer systems for qualifying a human subject for a re-order for over-the-counter delivery of a dipeptidyl peptidase-4 inhibitor pharmaceutical composition for lowering blood sugar, e.g., thereby, treating Type 2 diabetes and/or maintaining sub-diabetic blood sugar levels. In one embodiment, a computer system includes instructions, responsive to receiving a re-order request from the subject for the dipeptidyl peptidase-4 inhibitor pharmaceutical composition, performing a re-fulfillment procedure comprising conducting a second survey of the subject thereby obtaining a second plurality of survey results necessary to run against a third plurality of filters of a first category class and a fourth plurality of filters of a second category class. The method also includes running all or a portion of the second plurality of survey results against a third plurality of filters of a first category class, wherein, when a respective filter in the third plurality of filters is fired, the subject is deemed not qualified for delivery of the dipeptidyl peptidase-4 inhibitor pharmaceutical composition and the method is terminated without delivery of the dipeptidyl peptidase-4 inhibitor pharmaceutical composition to the subject. The method also includes running all or a portion of the second plurality of survey results against a fourth plurality of filters of a second category class, wherein, when a respective filter in the fourth plurality of filters is fired, the subject is provided with a warning corresponding to the respective filter. The method also includes obtaining acknowledgment from the subject for the warning issued to the subject by any filter in the fourth plurality of filters. The method also includes proceeding with a re-fulfillment process when no filter in the third plurality of filters has been fired and the subject has acknowledged each warning associated with each filter in the fourth plurality of filters that was fired. The re-fulfillment process includes: storing an indication in a subject profile of a re-order for the dipeptidyl peptidase-4 inhibitor pharmaceutical composition, communicating the over-the-counter drug facts label for the dipeptidyl peptidase-4 inhibitor pharmaceutical composition to the subject, and authorizing, upon confirmation from the subject that the over-the-counter drug facts label has been received and read, provision of the dipeptidyl peptidase-4 inhibitor pharmaceutical composition to the subject. In some embodiments, the third series of filters includes one or more filters listed in Table 5.

In some embodiments, the third plurality of filters includes a pregnancy filter, a ketoacidosis filter, a skin problem filter, a stomach pain filter, a joint pain filter, and a blood sugar filter.

In some embodiments, the fourth series of filters includes one or more filters listed in Table 6. In some embodiments, the fourth plurality of filters includes a hypoglycemia symptom filter, a bodily stress filter, and a drug interaction filter.

In some embodiments, the third and fourth plurality of filters includes filters selected from the filters listed in Table 8. In some embodiments, the third plurality of filters of the first category class include a third sub-plurality of the filters listed in Table 8, for example, 2, 3, 4, 5, 6, 7, 8, 9, 10, or all 11 of the filters listed in Table 8, and the fourth plurality of filters of the first category class include a fourth sub-plurality of the filters listed in Table 8, which is different from the third sub-plurality of filters, for example, 2, 3, 4, 5, 6, 7, 8, 9, 10, or all 11 of the filters listed in Table 8. In some embodiments, each of the filters in the third sub-plurality of filters is different from each of the filters in the fourth sub-plurality of filters (e.g., no filter listed in Table 8 is included in both the first sub-plurality and the second sub-plurality of filters). In some embodiments, a system for qualifying a subject for delivery of an over-the-counter dipeptidyl peptidase-4 inhibitor pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 8, e.g., at 2, 3, 4, 5, 6, 7, 8, 9, 10, or all 11 of the filters listed in Table 8. In some embodiments, where a filter listed in Table 8 corresponds to a filter listed in Table 2, Table 3, Table 5, or Table 6, a threshold level sufficient to fire the corresponding filter listed in Table 2, Table 3, Table 5, or Table 6, as described in detail above, is sufficient to fire the filter listed in Table 8.

TABLE 8

Example filters for contraindications/risk factors associated with re-qualifying a subject for an over-the-counter provision of a dipeptidyl peptidase-4 inhibitor pharmaceutical composition

| Filter | Example Criteria |
|---|---|
| 1b | a pregnancy filter |
| 2b | a ketoacidosis symptom filter |
| 3b | a skin problem filter |
| 4b | a stomach pain filter |
| 5b | a joint pain filter |
| 6b | a blood sugar status filter |
| 7b | a heart failure symptom filter |
| 8b | a hypoglycemia symptom filter |
| 9b | a bodily stress filter |
| 10b | a drug interaction filter |
| 11b | a side effect filter |

In one aspect, the present disclosure provides a computer system for qualifying a human subject for over-the-counter delivery of a dipeptidyl peptidase-4 inhibitor pharmaceutical composition for lowering blood sugar, the computer system comprising one or more processors and a memory, the memory comprising non-transitory instructions which, when executed by the one or more processor, perform a method comprising: a) conducting a first survey of the subject thereby obtaining a first plurality of survey results, wherein the first plurality of survey results comprises: whether the subject is any one of (i) pregnant, (ii) breastfeeding, or (iii) planning to become pregnant, a Type 1 diabetes status of the subject, a ketoacidosis status of the subject, an age of the subject, a blood sugar level of the subject, whether the subject has ever had a pancreatic problem, an alcohol consumption status of the subject, whether the subject has ever had a gallstone, whether the subject has ever had high triglyceride levels, and whether the subject is taking a medication that interacts with the dipeptidyl peptidase-4 inhibitor pharmaceutical composition; b) running all or a portion of the first plurality of survey results against a first plurality of filters of a first category class, wherein, when a respective filter in the first plurality of filters is fired, the subject is deemed not qualified for delivery of the dipeptidyl peptidase-4 inhibitor pharmaceutical composition and the method is terminated without delivery of the dipeptidyl peptidase-4 inhibitor pharmaceutical composition to the subject, wherein the first plurality of filters comprises: a first pregnancy filter that is fired at least when the first plurality of survey results indicates that the subject is pregnant or the subject is breastfeeding, a Type 1 diabetes filter that is fired at least when the first plurality of survey results indicates that the subject has Type 1 diabetes, a ketoacidosis filter that is fired at least when the first plurality of survey results indicates that the subject has ketoacidosis, an age filter, and a first blood sugar filter that is fired at least when the first plurality of survey results indicates that the subject has a blood sugar level that is either (i) below a first baseline blood sugar level or (ii) above a ceiling blood sugar level; c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises: a pancreatic disease filter that is fired at least when the first plurality of survey results indicates that the subject has had pancreatitis, an alcohol consumption filter, a gallstone filter that is fired at least when the first plurality of survey results indicates that the subject has had a gallstone, a triglyceride filter that is fired at least when the first plurality of survey results indicates that the subject has had a high triglyceride level, and a first drug interaction filter that is fired at least when the first plurality of survey results indicates that the subject is taking a medication that interacts with the dipeptidyl peptidase-4 inhibitor pharmaceutical composition, d) obtaining acknowledgment from the subject for the warning issued to the subject by any filter in the second plurality of filters; and e) proceeding with a fulfillment process when (i) no filter in the first plurality of filters has been fired and (ii) the subject has acknowledged each warning associated with each filter in the second plurality of filters that was fired, wherein the fulfillment process comprises: storing an indication in a subject profile of an initial order for the dipeptidyl peptidase-4 inhibitor pharmaceutical composition, communicating an over the counter drug facts label for the dipeptidyl peptidase-4 inhibitor pharmaceutical composition to the subject, and authorizing, upon confirmation from the subject that the over the counter drug facts label has been received and read, provision of the dipeptidyl peptidase-4 inhibitor pharmaceutical composition to the subject.

In some embodiments of the aspects disclosed above, the dipeptidyl peptidase-4 inhibitor pharmaceutical composition has the structure of structure (I):

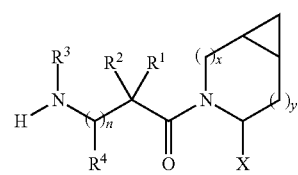

wherein x is 0 or 1 and y is 0 or 1, provided that x=1 when y=0 and x=0 when y=1; and wherein n is 0 or 1; X is H or CN; $R^1$, $R^2$, $R^3$ and $R^4$ are the same or different and are independently selected from hydrogen, alkyl, alkenyl, alkynyl, cycloalkyl, cycloalkylalkyl, bicycloalkyl, tricycloalkyl, alkylcycloalkyl, hydroxyalkyl, hydroxyalkylcycloalkyl, hydroxycycloalkyl, hydroxybicycloalkyl, hydroxytricycloalkyl, bicycloalkylalkyl, alkylthioalkyl, arylalkylthioalkyl, cycloalkenyl, aryl, aralkyl, heteroaryl, heteroarylalkyl, cycloheteroalkyl or cycloheteroalkylalkyl; all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfinyl, aminosulfonyl, alkylsulfinyl, sulfonamido or sulfonyl; and $R^1$ and $R^3$ may optionally be taken together to form —$(CR^5R^6)_m$— where m is 2 to 6, and R and R are the same or different and are independently selected from hydroxy, alkoxy, H, alkyl, alkenyl, alkynyl, cycloalkyl, halo, amino, substituted amino, cycloalkylalkyl, cycloalkenyl, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or $R^1$ and $R^4$ may optionally be taken together to form —$(CR^7R^8)_p$— wherein p is 2 to 6, and $R^7$ and $R^8$ are the same or different and are independently selected from hydroxy, alkoxy, cyano, H, alkyl, alkenyl, alkynyl, cycloalkyl, cycloalkylalkyl, cycloalkenyl, halo, amino, substituted amino, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino; or optionally $R^1$ and $R^3$ together with

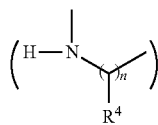

form a 5 to 7 membered ring containing a total of 2 to 4 heteroatoms selected from N, O, S, SO, or $SO_2$; or optionally $R^1$ and $R^3$ together with

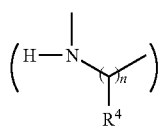

form a 4 to 8 membered cycloheteroalkyl ring wherein the cycloheteroalkyl ring has an optional aryl ring fused thereto or an optional 3 to 7 membered cycloalkyl ring fused thereto; including all stereoisomers thereof; and a pharmaceutically acceptable salt thereof, or a prodrug ester thereof, and all stereoisomers thereof.

In some embodiments of the aspects disclosed above, the dipeptidyl peptidase-4 inhibitor pharmaceutical composition includes saxagliptin or a pharmaceutically acceptable salt thereof.

In some embodiments of the aspects disclosed above, upon confirmation from the subject that the over-the-counter drug facts label has been received and read, the subject is authorized for provision of a dosage of 2.5 mg per day of saxagliptin.

In some embodiments of the aspects disclosed above, the dipeptidyl peptidase-4 inhibitor pharmaceutical composition includes saxagliptin and the subject is administered a dosage from 1 mg to 5 mg per day.

In some embodiments of the aspects disclosed above, the dipeptidyl peptidase-4 inhibitor pharmaceutical composition is selected from the group consisting of sitagliptin, linagliptin, and alogliptin.

In some embodiments of the aspects disclosed above, upon confirmation from the subject that the over-the-counter drug facts label has been received and read, the subject is authorized for provision of a dosage of from 12.5 mg to 100 mg per day of sitagliptin. In some embodiments, the subject is authorized for provision of a dosage selected from the set of 25 mg, 50 mg, and 100 mg per day of sitagliptin.

In some embodiments of the aspects disclosed above, upon confirmation from the subject that the over-the-counter drug facts label has been received and read, the subject is authorized for provision of a dosage of from 3 mg to 25 mg per day of alogliptin. In some embodiments, the subject is authorized for provision of a dosage selected from the set of 6.25 mg, 12.5 mg, and 25 mg per day of alogliptin.

In some embodiments of the aspects disclosed above, upon confirmation from the subject that the over-the-counter drug facts label has been received and read, the subject is authorized for provision of a dosage of from 1 mg to 5 mg per day of linagliptin. In some embodiments, the subject is authorized for provision of a dosage selected from the set of 2.5 mg and 5 mg per day of linagliptin.

In some embodiments of the aspects disclosed above, the first pregnancy filter is also fired when the first plurality of survey results indicates that the subject plans to become pregnant within a predetermined period of time.

In some embodiments of the aspects disclosed above, the age filter is fired when the first plurality of survey results indicates that the subject is less than eighteen years old.

In some embodiments of the aspects disclosed above, the first floor blood sugar level used in the first blood sugar filter is 6.5% glycated hemoglobin.

In some embodiments of the aspects disclosed above, the ceiling blood sugar level used in the first blood sugar filter is 7.5% glycated hemoglobin.

In some embodiments of the aspects disclosed above, the first alcohol consumption filter is fired when the first plurality of survey results indicates that the subject, on average, consumes at least a predetermined number of alcoholic drinks over a predetermined period of time.

In some embodiments of the aspects disclosed above, the medication that interacts with the dipeptidyl peptidase-4 inhibitor pharmaceutical composition, which is capable of firing the first drug interaction filter, is selected from the group consisting of an HIV medication, an AIDS medication, an antifungal medication, an antibiotic, or a medication for diabetes.

In some embodiments of the aspects disclosed above, the first plurality of survey results further comprises whether the subject is allergic to the dipeptidyl peptidase-4 inhibitor pharmaceutical composition, and the first plurality of filters includes an adverse reaction filter that is fired when the first plurality of survey results indicates that the subject is allergic to the dipeptidyl peptidase-4 inhibitor pharmaceutical composition.

In some embodiments of the aspects disclosed above, the first plurality of survey results further comprises whether the subject has ever had heart failure, and the second plurality of filters includes a heart failure filter that is fired when the first plurality of survey results indicates that the subject has had heart failure.

In some embodiments of the aspects disclosed above, the warning corresponding to a respective filter in the second plurality of filters comprises a prompt for the subject to indicate whether they have discussed the risk factor underlying the respective filter in the second plurality of filters that was fired with a health care provider; and acknowledgement is obtained from the subject when the subject indicates that they have discussed the risk factor underlying the respective filter in the second plurality of filters that was fired with a health care provider.

In some embodiments of the aspects disclosed above, the fulfillment process further comprises: storing a destination associated with the subject in the subject profile.

In some embodiments of the aspects disclosed above, the fulfillment process further comprises: coordinating shipping of the dipeptidyl peptidase-4 inhibitor pharmaceutical composition to a physical address associated with the subject.

In one aspect, the present disclosure provides a computer system for re-qualifying a human subject for over-the-counter delivery of a dipeptidyl peptidase-4 inhibitor pharmaceutical composition for lowering blood sugar, the computer system comprising one or more processors and a memory, the memory comprising non-transitory instructions which, when executed by the one or more processor, perform a method comprising: f) responsive to receiving a re-order request from a subject for a dipeptidyl peptidase-4 inhibitor blocker pharmaceutical composition, performing a re-fulfillment procedure comprising: (i) conducting a second survey of the subject thereby obtaining a second plurality of survey results, wherein the second plurality of survey results comprises information indicating: whether the subject is one of (i) pregnant, (ii) breastfeeding, or (iii) planning to become pregnant, whether the subject has developed ketoacidosis since receiving their last provision of the dipeptidyl peptidase-4 inhibitor pharmaceutical composition, whether the subject has experienced a skin problem since receiving their last provision of the dipeptidyl peptidase-4 inhibitor pharmaceutical composition, whether the subject has experienced stomach pain since receiving their last provision of the dipeptidyl peptidase-4 inhibitor pharmaceutical composition, whether the subject has experienced joint pain since receiving their last provision of the dipeptidyl peptidase-4 inhibitor pharmaceutical composition, whether the subject has developed hypoglycemia since receiving their last provision of the dipeptidyl peptidase-4 inhibitor pharmaceutical composition, whether the subject is experiencing a bodily stress, whether the subject is taking a medication that interacts with the dipeptidyl peptidase-4 inhibitor pharmaceutical composition, and if a predetermined period of time has passed since the subject received a provision of the dipeptidyl peptidase-4 inhibitor blocker pharmaceutical composition, a blood sugar level of the subject; (ii) running all or a portion of the second plurality of survey results against a third plurality of filters of the first category class, wherein, when a respective filter in the third plurality of filters is fired, the subject is deemed not qualified for the dipeptidyl peptidase-4 inhibitor pharmaceutical composition and the re-fulfillment process is terminated without delivery of the dipeptidyl peptidase-4 inhibitor pharmaceutical composition to the subject, wherein the third plurality of filters comprise: a second pregnancy filter that is fired at least when the second plurality of survey results indicates that the subject is pregnant or the subject is breastfeeding, a ketoacidosis symptom filter that is fired at least when the second plurality of survey results indicates that the subject has developed ketoacidosis since receiving their last provision of the dipeptidyl peptidase-4 inhibitor pharmaceutical composition, a skin problem filter that is fired at least when the second plurality of survey results indicates that the subject has experienced blistering or an exfoliative skin condition since receiving their last provision of the dipeptidyl peptidase-4 inhibitor pharmaceutical composition, a stomach pain filter that is fired at least when the second plurality of survey results indicates that the subject has experienced stomach pain since receiving their last provision of the dipeptidyl peptidase-4 inhibitor pharmaceutical composition, a joint pain filter that is fired at least when the second plurality of survey results indicates that the subject has experienced joint pain since receiving their last provision of the dipeptidyl peptidase-4 inhibitor pharmaceutical composition, and a second blood sugar filter that is fired at least when: (i) a predetermined period of time has passed since the subject received a provision of the dipeptidyl peptidase-4 inhibitor pharmaceutical composition, and (ii) the second plurality of survey results indicates that the subject has a blood sugar level of at least a second ceiling blood sugar level; (iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises: a hypoglycemia symptom filter that is fired at least when the second plurality of survey results indicates that the subject has developed hypoglycemia since receiving their last provision of the dipeptidyl peptidase-4 inhibitor pharmaceutical composition, a bodily stress filter that is fired at least when the second plurality of survey results indicates that the subject is experiencing a bodily stress, and a second drug interaction filter that is fired at least when the second plurality of survey results indicates that the subject is taking a medication that interacts with the dipeptidyl peptidase-4 inhibitor pharmaceutical composition; (iv) obtaining acknowledgment from the subject for the warning issued to the subject by any filter in the fourth plurality of filters; and (v) proceeding with the re-fulfillment process when (i) the re-fulfillment process is not already terminated by the firing of a filter in the third plurality of filters and (ii) the subject has acknowledged each warning associated with each filter in the third plurality of filters that was fired and that is associated with a warning, wherein the re-fulfillment process further comprises: storing an indication in the subject profile of a re-order for the dipeptidyl peptidase-4 inhibitor pharmaceutical composition, communicating the over the counter drug facts label for the dipeptidyl peptidase-4 inhibitor pharmaceutical composition to the subject, and authorizing, upon confirmation from the subject that the over the counter drug facts label has been received and read, a re-order provision of the dipeptidyl peptidase-4 inhibitor pharmaceutical composition to the subject.

In some embodiments of the aspects disclosed above, the second pregnancy filter is also fired when the second plurality of survey results indicates that the subject plans to become pregnant within a predetermined period of time.

In some embodiments of the aspects disclosed above, a symptom of ketoacidosis, which is capable of firing the ketoacidosis filter, is selected from the group consisting of an increase of ketones in the blood of the subject, an increase of ketones in the urine of the subject, nausea, tiredness, vomiting, trouble breathing, and stomach pain including the abdominal area.

In some embodiments of the aspects disclosed above, the second ceiling blood sugar level used in the second blood sugar filter is 7% glycated hemoglobin.

In some embodiments of the aspects disclosed above, a symptom of hypoglycemia, which is capable of firing the hypoglycemia symptom filter, is selected from the group consisting of shaking, sweating, rapid heartbeat, change in vision, hunger, headaches, and a change in mood.

In some embodiments of the aspects disclosed above, the bodily stress, which is capable of firing the bodily stress filter, is selected from the group consisting of a fever, a recent trauma, an infection, or a recent surgery.

In some embodiments of the aspects disclosed above, the medication that interacts with the dipeptidyl peptidase-4 inhibitor pharmaceutical composition, which is capable of firing the drug interaction filter, is selected from the group consisting of an HIV medication, an AIDS medication, an antifungal medication, an antibiotic, or a medication for diabetes.

In some embodiments of the aspects disclosed above, the second plurality of survey results further comprises whether the subject has experienced a side effect from the dipeptidyl peptidase-4 inhibitor pharmaceutical composition since receiving their last provision of the dipeptidyl peptidase-4 inhibitor pharmaceutical composition, and the fourth plurality of filters further comprises a side effect filter that is fired at least when the second plurality of survey results indicates that the subject has experienced, since receiving their last provision of the dipeptidyl peptidase-4 inhibitor pharmaceutical composition, a side effect selected from the group consisting of an upper respiratory tract infection, a urinary tract infection, and headaches.

In some embodiments of the aspects disclosed above, the second plurality of survey results further comprises whether the subject has developed heart failure since receiving their last provision of the dipeptidyl peptidase-4 inhibitor pharmaceutical composition, and the third plurality of filters further comprises a heart failure symptom filter that is fired at least when the second plurality of survey results indicates that the subject has developed, since receiving their last provision of the dipeptidyl peptidase-4 inhibitor pharmaceutical composition, heart failure.

In some embodiments of the aspects disclosed above, a symptom of heart failure, which is capable of firing the heart failure symptom filter, is selected from the group consisting of increased shortness of breath, trouble breathing, a rapid increase in weight, swelling of the feet, swelling of the ankles, and swelling of the legs.

In some embodiments of the aspects disclosed above, the lowering blood sugar is to treat Type 2 diabetes and/or maintain sub-diabetic blood sugar levels.

In some embodiments, the disclosure provides methods for lowering blood sugar with an over the counter dipeptidyl peptidase-4 inhibitor pharmaceutical composition. The method includes providing a first survey for obtaining a first information set from the human, via a computer system having a processor programmed to perform the first survey, where the first information set includes information about the human that relates to potential risk factors and contraindications for the dipeptidyl peptidase-4 inhibitor pharmaceutical composition, as described herein. The method also includes applying an algorithm to the first information set, via a computer system having a processor programmed to perform the algorithm. The algorithm runs all or a portion of the first information set against a first plurality of filters, where the human is deemed not qualified for treatment with the over the counter dipeptidyl peptidase-4 inhibitor pharmaceutical composition for lowering blood sugar when a respective filter in the first plurality of filters is fired and the method is terminated without authorizing provision of the dipeptidyl peptidase-4 inhibitor pharmaceutical composition to the human, where the first plurality of filters includes filters related to contraindications of the dipeptidyl peptidase-4 inhibitor pharmaceutical composition as described herein. The algorithm also runs all or a portion of the first information set against a second plurality of filters, where, when a respective filter in the second plurality of filters is fired, the human is provided with a warning corresponding to the respective filter, and where the second plurality of filters includes filters related to risk factors for the dipeptidyl peptidase-4 inhibitor pharmaceutical composition as described herein. The algorithm also obtains acknowledgment from the human of the risk factor associated with each warning issued to the human by any filter in the second plurality of filters. In some embodiments, the acknowledgement includes confirmation that the human has discussed the risk factor with a physician. The algorithm proceeds with a fulfillment process when (a) no filter in the first plurality of filters has been fired and (b) the human has acknowledged each warning associated with each filter in the second plurality of filters that was fired. The fulfillment process includes storing an indication in a subject profile of an initial order for the dipeptidyl peptidase-4 inhibitor pharmaceutical composition, communicating an over the counter drug facts label for the dipeptidyl peptidase-4 inhibitor pharmaceutical composition to the human, and authorizing, upon confirmation from the subject that the over the counter drug facts label has been received and read, provision of the dipeptidyl peptidase-4 inhibitor pharmaceutical composition to the human, where the authorization includes a destination associated with the subject. In some embodiments, the method also includes treating the human to lower the blood sugar of the human, upon authorization of the provision e.g., by providing access to the dipeptidyl peptidase-4 inhibitor pharmaceutical composition to the human and/or by administering the dipeptidyl peptidase-4 inhibitor pharmaceutical composition to lower blood sugar in the human.

EXAMPLES

Example 1

A computer system is configured for qualifying a subject for over-the-counter delivery of a saxagliptin pharmaceutical composition for lowering blood sugar, e.g., thereby treating Type 2 diabetes. The computer system includes instructions for conducting a survey of the subject. The survey is utilized to obtain one or more results of: whether the subject is one of pregnant, breastfeeding, or planning to become pregnant, a ketoacidosis status of the subject, an age of the subject, a blood sugar level of the subject, whether the subject has ever had heart failure, whether the subject has ever had a pancreatic problem, an alcohol consumption status of the subject, whether the subject has ever had a gallstone, whether the subject has ever had high triglyceride levels, and whether the subject is taking a medication that interacts with the dipeptidyl peptidase-4 inhibitor pharmaceutical composition.

The computer system runs survey results against a first series of filters that are each associated with a first filter category class. Filters in the first filter category class are configured to prevent authorization for delivery of the OTC saxagliptin when the subject's survey results indicate a contraindication for saxagliptin. The first series of filters includes a first pregnancy filter, a Type 1 diabetes filter, a ketoacidosis filter, an age filter, and a first blood sugar filter.

The computer system runs survey results against a second series of filters that each generates a warning when the subject's survey results indicate a risk factor for the OTC saxagliptin. In some embodiments, the second series of filters includes a heart failure filter, a pancreatic disease filter, an alcohol consumption filter, a gallstone filter, a triglyceride filter, and a first drug interaction filter.

The computer system prompts the subject to acknowledge each warning associated with a filter in the second series of filters that was fired (e.g., that they have discussed the underlying risk factor with a medical professional). The computer system proceeds with a fulfillment process only when none of the filters in the first series of filters was fired and the subject acknowledged each warning issued in association with the second series of filters that was fired.

The computer system stores an indication of an initial order of the OTC saxagliptin in a subject profile, and communicates an over-the-counter drug facts label for the saxagliptin pharmaceutical composition to the subject. Upon confirmation from the subject that they have received and read the over-the-counter drug facts label, the computer system authorizes provision of from 1 mg to 5 mg per day of the OTC saxagliptin pharmaceutical composition to the subject.

The computer system includes instructions for conducting a survey of the subject responsive to a re-order request of the OTC saxagliptin pharmaceutical composition. This survey is utilized to obtain one or more results of: whether the subject is one of pregnant, breastfeeding, or planning to become pregnant, whether the subject has developed ketoacidosis since receiving their last provision of saxagliptin, whether the subject has developed heart failure since receiving their last provision of saxagliptin, whether the subject has experienced a skin problem since receiving their last provision of saxagliptin, whether the subject has experienced stomach pain since receiving their last provision of saxagliptin, whether the subject has experienced joint pain since receiving their last provision of saxagliptin, whether the subject has developed hypoglycemia since receiving their last provision of saxagliptin, whether the subject is experiencing a bodily stress, whether the subject is taking a medication that interacts with saxagliptin, and a blood sugar level of the subject.

The computer system runs the survey results against a third series of filters that are each associated with the first filter category class. Filters in the first filter category class are configured to prevent authorization for delivery of the OTC saxagliptin when the subject's survey results indicate a contraindication for saxagliptin. The third series of filters includes a second pregnancy filter, a ketoacidosis filter, a heart failure filter, a skin problem filter, a stomach pain filter, a joint pain filter, and a second blood sugar filter.

The computer system runs survey results against a fourth series of filters that each generates a warning when the subject's survey results indicate a risk factor for the OTC saxagliptin. The fourth series of filters includes a hypoglycemia symptom filter, a bodily stress filter, and a second drug interaction filter.

The computer system prompts the subject to acknowledge each warning associated with a filter in the fourth series of filters that was fired (e.g., that they have discussed the underlying risk factor with a medical professional). The computer system proceeds with a re-fulfillment process only when none of the filters in the third series of filters was fired and the subject acknowledged each warning issued in association with the fourth series of filters that was fired.

The computer system stores an indication of a re-order of the OTC saxagliptin in the subject profile, and communicates the over-the-counter drug facts label for the saxagliptin pharmaceutical composition to the subject. Upon confirmation from the subject that they have received and read the over-the-counter drug facts label, the computer system authorizes provision of from 1 mg to 5 mg per day of the OTC saxagliptin pharmaceutical composition to the subject.

Example 2

A computer system is configured for qualifying a subject for over-the-counter delivery of an alogliptin pharmaceutical composition for lowering blood sugar, e.g., thereby treating Type 2 diabetes. The computer system includes instructions for conducting a survey of the subject. The survey is utilized to obtain one or more results of: whether the subject is one of pregnant, breastfeeding, or planning to become pregnant, a ketoacidosis status of the subject, an age of the subject, a blood sugar level of the subject, whether the subject has ever had heart failure, whether the subject has ever had a pancreatic problem, an alcohol consumption status of the subject, whether the subject has ever had a gallstone, whether the subject has ever had high triglyceride levels, and whether the subject is taking a medication that interacts with the dipeptidyl peptidase-4 inhibitor pharmaceutical composition.

The computer system runs survey results against a first series of filters that are each associated with a first filter category class. Filters in the first filter category class are configured to prevent authorization for delivery of the OTC alogliptin when the subject's survey results indicate a contraindication for alogliptin. The first series of filters includes a first pregnancy filter, a Type 1 diabetes filter, a ketoacidosis filter, an age filter, and a first blood sugar filter.

The computer system runs survey results against a second series of filters that each generates a warning when the subject's survey results indicate a risk factor for the OTC alogliptin. In some embodiments, the second series of filters includes a heart failure filter, a pancreatic disease filter, an alcohol consumption filter, a gallstone filter, a triglyceride filter, and a first drug interaction filter.

The computer system prompts the subject to acknowledge each warning associated with a filter in the second series of filters that was fired (e.g., that they have discussed the underlying risk factor with a medical professional). The computer system proceeds with a fulfillment process only when none of the filters in the first series of filters was fired and the subject acknowledged each warning issued in association with the second series of filters that was fired.

The computer system stores an indication of an initial order of the OTC amlodipine in a subject profile, and communicates an over-the-counter drug facts label for the saxagliptin pharmaceutical composition to the subject. Upon confirmation from the subject that they have received and read the over-the-counter drug facts label, the computer system authorizes provision of from 6.25 mg to 25 mg per day of the OTC alogliptin pharmaceutical composition to the subject.

The computer system includes instructions for conducting a survey of the subject responsive to a re-order request of the OTC alogliptin pharmaceutical composition. This survey is utilized to obtain one or more results of: whether the subject is one of pregnant, breastfeeding, or planning to become pregnant, whether the subject has developed ketoacidosis since receiving their last provision of alogliptin, whether the subject has developed heart failure since receiving their last provision of alogliptin, whether the subject has experienced a skin problem since receiving their last provision of alogliptin, whether the subject has experienced stomach pain since receiving their last provision of alogliptin, whether the subject has experienced joint pain since receiving their last provision of alogliptin, whether the subject has developed hypoglycemia since receiving their last provision of alogliptin, whether the subject is experiencing a bodily stress, whether the subject is taking a medication that interacts with alogliptin, and a blood sugar level of the subject.

The computer system runs the survey results against a third series of filters that are each associated with the first filter category class. Filters in the first filter category class are configured to prevent authorization for delivery of the OTC alogliptin when the subject's survey results indicate a contraindication for alogliptin. The third series of filters includes a second pregnancy filter, a ketoacidosis filter, a heart failure filter, a skin problem filter, a stomach pain filter, a joint pain filter, and a second blood sugar filter.

The computer system runs survey results against a fourth series of filters that each generates a warning when the subject's survey results indicate a risk factor for the OTC alogliptin. The fourth series of filters includes a hypoglycemia symptom filter, a bodily stress filter, and a second drug interaction filter.

The computer system prompts the subject to acknowledge each warning associated with a filter in the fourth series of filters that was fired (e.g., that they have discussed the underlying risk factor with a medical professional). The computer system proceeds with a re-fulfillment process only when none of the filters in the third series of filters was fired and the subject acknowledged each warning issued in association with the fourth series of filters that was fired.

The computer system stores an indication of a re-order of the OTC alogliptin in the subject profile, and communicates the over-the-counter drug facts label for the alogliptin pharmaceutical composition to the subject. Upon confirmation from the subject that they have received and read the over-the-counter drug facts label, the computer system authorizes provision of from 3 mg to 25 mg per day of the OTC alogliptin pharmaceutical composition to the subject.

Example 3

A computer system is configured for qualifying a subject for over-the-counter delivery of a sitagliptin pharmaceutical composition for lowering blood sugar, e.g., thereby treating Type 2 diabetes. The computer system includes instructions for conducting a survey of the subject. The survey is utilized to obtain one or more results of: whether the subject is one of pregnant, breastfeeding, or planning to become pregnant, a ketoacidosis status of the subject, an age of the subject, a blood sugar level of the subject, whether the subject has ever had a pancreatic problem, an alcohol consumption status of the subject, whether the subject has ever had a gallstone, whether the subject has ever had high triglyceride levels, and whether the subject is taking a medication that interacts with the dipeptidyl peptidase-4 inhibitor pharmaceutical composition.

The computer system runs survey results against a first series of filters that are each associated with a first filter category class. Filters in the first filter category class are configured to prevent authorization for delivery of the OTC sitagliptin when the subject's survey results indicate a contraindication for sitagliptin. The first series of filters includes a first pregnancy filter, a Type 1 diabetes filter, a ketoacidosis filter, an age filter, and a first blood sugar filter.

The computer system runs survey results against a second series of filters that each generates a warning when the subject's survey results indicate a risk factor for the OTC sitagliptin. In some embodiments, the second series of filters includes a pancreatic disease filter, an alcohol consumption filter, a gallstone filter, a triglyceride filter, and a first drug interaction filter.

The computer system prompts the subject to acknowledge each warning associated with a filter in the second series of filters that was fired (e.g., that they have discussed the underlying risk factor with a medical professional). The computer system proceeds with a fulfillment process only when none of the filters in the first series of filters was fired and the subject acknowledged each warning issued in association with the second series of filters that was fired.

The computer system stores an indication of an initial order of the OTC sitagliptin in a subject profile, and communicates an over-the-counter drug facts label for the sitagliptin pharmaceutical composition to the subject. Upon confirmation from the subject that they have received and read the over-the-counter drug facts label, the computer system authorizes provision of from 12.5 mg to 100 mg per day of the OTC sitagliptin pharmaceutical composition to the subject.

The computer system includes instructions for conducting a survey of the subject responsive to a re-order request of the OTC sitagliptin pharmaceutical composition. This survey is utilized to obtain one or more results of: whether the subject is one of pregnant, breastfeeding, or planning to become pregnant, whether the subject has developed ketoacidosis since receiving their last provision of sitagliptin, whether the subject has experienced a skin problem since receiving their last provision of sitagliptin, whether the subject has experienced stomach pain since receiving their last provision of sitagliptin, whether the subject has experienced joint pain since receiving their last provision of sitagliptin, whether the subject has developed hypoglycemia since receiving their last provision of sitagliptin, whether the subject is experiencing a bodily stress, whether the subject is taking a medication that interacts with sitagliptin, and a blood sugar level of the subject.

The computer system runs the survey results against a third series of filters that are each associated with the first filter category class. Filters in the first filter category class are configured to prevent authorization for delivery of the OTC sitagliptin when the subject's survey results indicate a contraindication for sitagliptin. The third series of filters includes a second pregnancy filter, a ketoacidosis filter, a skin problem filter, a stomach pain filter, a joint pain filter, and a second blood sugar filter.

The computer system runs survey results against a fourth series of filters that each generates a warning when the subject's survey results indicate a risk factor for the OTC sitagliptin. The fourth series of filters includes a hypoglycemia symptom filter, a bodily stress filter, and a second drug interaction filter.

The computer system prompts the subject to acknowledge each warning associated with a filter in the fourth series of filters that was fired (e.g., that they have discussed the underlying risk factor with a medical professional). The computer system proceeds with a re-fulfillment process only when none of the filters in the third series of filters was fired and the subject acknowledged each warning issued in association with the fourth series of filters that was fired.

The computer system stores an indication of a re-order of the OTC sitagliptin in the subject profile, and communicates the over-the-counter drug facts label for the sitagliptin pharmaceutical composition to the subject. Upon confirmation from the subject that they have received and read the over-the-counter drug facts label, the computer system authorizes provision of from 12.5 mg to 100 mg per day of the OTC sitagliptin pharmaceutical composition to the subject.

Example 4

A computer system is configured for qualifying a subject for over-the-counter delivery of a linagliptin pharmaceutical composition for lowering blood sugar, e.g., thereby treating Type 2 diabetes. The computer system includes instructions for conducting a survey of the subject. The survey is utilized to obtain one or more results of: whether the subject is one of pregnant, breastfeeding, or planning to become pregnant, a ketoacidosis status of the subject, an age of the subject, a blood sugar level of the subject, whether the subject has ever had a pancreatic problem, an alcohol consumption status of the subject, whether the subject has ever had a gallstone, whether the subject has ever had high triglyceride levels, and whether the subject is taking a medication that interacts with the dipeptidyl peptidase-4 inhibitor pharmaceutical composition.

The computer system runs survey results against a first series of filters that are each associated with a first filter category class. Filters in the first filter category class are configured to prevent authorization for delivery of the OTC linagliptin when the subject's survey results indicate a contraindication for linagliptin. The first series of filters includes a first pregnancy filter, a Type 1 diabetes filter, a ketoacidosis filter, an age filter, and a first blood sugar filter.

The computer system runs survey results against a second series of filters that each generates a warning when the subject's survey results indicate a risk factor for the OTC linagliptin. In some embodiments, the second series of filters includes a pancreatic disease filter, an alcohol consumption filter, a gallstone filter, a triglyceride filter, and a first drug interaction filter.

The computer system prompts the subject to acknowledge each warning associated with a filter in the second series of filters that was fired (e.g., that they have discussed the underlying risk factor with a medical professional). The computer system proceeds with a fulfillment process only when none of the filters in the first series of filters was fired and the subject acknowledged each warning issued in association with the second series of filters that was fired.

The computer system stores an indication of an initial order of the OTC linagliptin in a subject profile, and communicates an over-the-counter drug facts label for the linagliptin pharmaceutical composition to the subject. Upon confirmation from the subject that they have received and read the over-the-counter drug facts label, the computer system authorizes provision of from 1 mg to 5 mg per day of the OTC linagliptin pharmaceutical composition to the subject.

The computer system includes instructions for conducting a survey of the subject responsive to a re-order request of the OTC linagliptin pharmaceutical composition. This survey is utilized to obtain one or more results of: whether the subject is one of pregnant, breastfeeding, or planning to become pregnant, whether the subject has developed ketoacidosis since receiving their last provision of linagliptin, whether the subject has experienced a skin problem since receiving their last provision of linagliptin, whether the subject has experienced stomach pain since receiving their last provision of linagliptin, whether the subject has experienced joint pain since receiving their last provision of linagliptin, whether the subject has developed hypoglycemia since receiving their last provision of linagliptin, whether the subject is experiencing a bodily stress, whether the subject is taking a medication that interacts with linagliptin, and a blood sugar level of the subject.

The computer system runs the survey results against a third series of filters that are each associated with the first filter category class. Filters in the first filter category class are configured to prevent authorization for delivery of the OTC linagliptin when the subject's survey results indicate a contraindication for linagliptin. The third series of filters includes a second pregnancy filter, a ketoacidosis filter, a skin problem filter, a stomach pain filter, a joint pain filter, and a second blood sugar filter.

The computer system runs survey results against a fourth series of filters that each generates a warning when the subject's survey results indicate a risk factor for the OTC linagliptin. The fourth series of filters includes a hypoglycemia symptom filter, a bodily stress filter, and a second drug interaction filter.

The computer system prompts the subject to acknowledge each warning associated with a filter in the fourth series of filters that was fired (e.g., that they have discussed the underlying risk factor with a medical professional). The computer system proceeds with a re-fulfillment process only when none of the filters in the third series of filters was fired and the subject acknowledged each warning issued in association with the fourth series of filters that was fired.

The computer system stores an indication of a re-order of the OTC linagliptin in the subject profile, and communicates the over-the-counter drug facts label for the linagliptin pharmaceutical composition to the subject. Upon confirmation from the subject that they have received and read the over-the-counter drug facts label, the computer system authorizes provision of from 1 mg to 5 mg per day of the OTC linagliptin pharmaceutical composition to the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for lowering blood sugar in a human subject with an over-the-counter a dipeptidyl peptidase-4 inhibitor pharmaceutical composition, the method comprising:
   A) providing a first survey for obtaining a first plurality of survey results about the subject, via a first computer system having a processor programed to perform the first survey, wherein the first plurality of survey results indicates at least:
      whether the subject is pregnant or breastfeeding,
      a Type 1 diabetes status of the subject,
      a ketoacidosis status of the subject,
      an age of the subject,
      a blood sugar level of the subject,
      whether the subject has ever had a pancreatic problem,
      an alcohol consumption status of the subject,
      whether the subject has ever had a gallstone,
      whether the subject has ever had high triglyceride levels, and
      whether the subject is taking a medication that interacts with the dipeptidyl peptidase-4 inhibitor pharmaceutical composition;
   B) applying an algorithm to the first plurality of survey results, via a second computer system having a process programed to perform the algorithm, wherein the algorithm:
      i) runs all or a portion of the first plurality of survey results against a first plurality of filters of a first category class, wherein, when a respective filter in the first plurality of filters is fired, the subject is deemed not qualified for authorizing provision of the dipeptidyl peptidase-4 inhibitor pharmaceutical composition and the method is terminated without authorizing provision of the dipeptidyl peptidase-4 inhibitor pharmaceutical composition to the subject, wherein the first plurality of filters comprises:
         a first pregnancy filter that is fired at least when the first plurality of survey results indicates that the subject is pregnant or the subject is breastfeeding,
         a Type 1 diabetes filter that is fired at least when the first plurality of survey results indicates that the subject has Type 1 diabetes,
         a ketoacidosis filter that is fired at least when the first plurality of survey results indicates that the subject has ketoacidosis,
         an age filter, and
         a first blood sugar filter that is fired at least when the first plurality of survey results indicates that the subject has a blood sugar level that is either a) below a first floor blood sugar level or b) above a first ceiling blood sugar level;
      ii) runs all or a portion of the first plurality of survey results against a second plurality of filters of a second category class, wherein, when a respective filter in the second plurality of filters is fired, the subject is provided with a warning corresponding to the respective filter, and wherein the second plurality of filters comprises:
         a pancreatic disease filter that is fired at least when the first plurality of survey results indicates that the subject has had pancreatitis,
         an alcohol consumption filter,
         a gallstone filter that is fired at least when the first plurality of survey results indicates that the subject has had a gallstone,
         a triglyceride filter that is fired at least when the first plurality of survey results indicates that the subject has had a high triglyceride level; and
         a first drug interaction filter that is fired at least when the first plurality of survey results indicates that the subject is taking a medication that interacts with the dipeptidyl peptidase-4 inhibitor pharmaceutical composition,
      iii) obtains acknowledgment from the subject for each warning issued to the subject by any filter in the second plurality of filters; and
      iv) proceeds with a fulfillment process when a) no filter in the first plurality of filters has been fired and b) the subject has acknowledged each warning associated with each filter in the second plurality of filters that was fired, wherein the fulfillment process comprises:
         storing an indication in a subject profile of an initial order for the dipeptidyl peptidase-4 inhibitor pharmaceutical composition,
         communicating an over the counter drug facts label for the dipeptidyl peptidase-4 inhibitor pharmaceutical composition to the subject, and
         authorizing, upon confirmation from the subject that the over the counter drug facts label has been received and read, provision of the dipeptidyl peptidase-4 inhibitor pharmaceutical composition to the subject; and
   C) administering the dipeptidyl peptidase-4 inhibitor pharmaceutical composition to the subject after authorization of the provision.

2. The method of claim 1, wherein the dipeptidyl peptidase-4 inhibitor pharmaceutical composition comprises saxagliptin or a pharmaceutically acceptable salt thereof.

3. The method of claim 2, wherein the subject is administered a dosage of 2.5 mg per day of saxagliptin.

4. The method of claim 1, wherein the dipeptidyl peptidase-4 inhibitor pharmaceutical composition comprises an active ingredient selected from the group consisting of sitagliptin, linagliptin, and alogliptin.

5. The method of claim 4, wherein the subject is administered a dosage of 50 mg per day of sitagliptin.

6. The method of claim 4, wherein the subject is administered a dosage of 12.5 mg per day of alogliptin.

7. The method of claim 4, wherein the subject is administered a dosage of 2.5 mg per day of linagliptin.

8. The method of claim 1, wherein the first floor blood sugar level used in the first blood sugar filter is 6.5% glycated hemoglobin.

9. The method of claim 1, wherein the first ceiling blood sugar level used in the first blood sugar filter is 7.5% glycated hemoglobin.

10. The method of claim 1, wherein the medication that interacts with the dipeptidyl peptidase-4 inhibitor pharmaceutical composition, which is capable of firing the first drug interaction filter, is selected from the group consisting of an HIV medication, an AIDS medication, an antifungal medication, an antibiotic, and a medication for diabetes.

11. The method of claim 1, wherein:
the first plurality of survey results further indicates whether the subject is allergic to the dipeptidyl peptidase-4 inhibitor pharmaceutical composition, and
the first plurality of filters includes an adverse reaction filter that is fired when the first plurality of survey results indicates that the subject is allergic to the dipeptidyl peptidase-4 inhibitor pharmaceutical composition.

12. The method of claim 1, wherein:
the first plurality of survey results further indicates whether the subject has ever had heart failure, and
the second plurality of filters includes a heart failure filter that is fired when the first plurality of survey results indicates that the subject has had heart failure.

13. The method of claim 1, wherein:
the warning corresponding to a respective filter in the second plurality of filters comprises a prompt for the subject to indicate whether they have discussed the risk factor underlying the respective filter in the second plurality of filters that was fired with a health care provider; and
acknowledgement is obtained from the subject when the subject indicates that they have discussed the risk factor underlying the respective filter in the second plurality of filters that was fired with a health care provider.

14. The method of claim 1 further comprising:
D) receiving a re-order request from the subject for the dipeptidyl peptidase 4 inhibitor blocker pharmaceutical composition, via a third computer system having a processor programed to receive the re-order request; and
E) performing a re-fulfillment procedure via a fourth computer system having a processor programed to perform the re-fulfillment procedure, the re-fulfillment procedure comprising:
  i) providing a second survey for obtaining a second plurality of survey results about the subject, wherein the second plurality of survey results comprises information indicating at least:
    whether the subject is pregnant or breastfeeding,
    whether the subject has developed ketoacidosis since receiving their last provision of the dipeptidyl peptidase-4 inhibitor pharmaceutical composition,
    whether the subject has experienced a skin problem since receiving their last provision of the dipeptidyl peptidase-4 inhibitor pharmaceutical composition,
    whether the subject has experienced stomach pain since receiving their last provision of the dipeptidyl peptidase-4 inhibitor pharmaceutical composition,
    whether the subject has experienced joint pain since receiving their last provision of the dipeptidyl peptidase-4 inhibitor pharmaceutical composition,
    whether the subject has developed hypoglycemia since receiving their last provision of the dipeptidyl peptidase-4 inhibitor pharmaceutical composition,
    whether the subject is experiencing a bodily stress,
    whether the subject has started taking a medication that interacts with the dipeptidyl peptidase-4 inhibitor pharmaceutical composition, and
    a blood sugar level of the subject;
  ii) running all or a portion of the second plurality of survey results against a third plurality of filters of the first category class, wherein, when a respective filter in the third plurality of filters is fired, the subject is deemed not qualified for the dipeptidyl peptidase-4 inhibitor pharmaceutical composition and the re-fulfillment process is terminated without authorizing provision of the dipeptidyl peptidase-4 inhibitor pharmaceutical composition to the subject, wherein the third plurality of filters comprise:
    a second pregnancy filter that is fired at least when the second plurality of survey results indicates that the subject is pregnant or the subject is breastfeeding,
    a ketoacidosis symptom filter that is fired at least when the second plurality of survey results indicates that the subject has developed ketoacidosis since receiving their last provision of the dipeptidyl peptidase-4 inhibitor pharmaceutical composition,
    a skin problem filter that is fired at least when the second plurality of survey results indicates that the subject has experienced blistering or an exfoliative skin condition since receiving their last provision of the dipeptidyl peptidase-4 inhibitor pharmaceutical composition,
    a stomach pain filter that is fired at least when the second plurality of survey results indicates that the subject has experienced stomach pain since receiving their last provision of the dipeptidyl peptidase-4 inhibitor pharmaceutical composition,
    a joint pain filter that is fired at least when the second plurality of survey results indicates that the subject has experienced joint pain since receiving their last provision of the dipeptidyl peptidase-4 inhibitor pharmaceutical composition, and
    a second blood sugar filter that is fired at least when the second plurality of survey results indicates that the subject has a blood sugar level above a second ceiling blood sugar level;
  iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises:
    a hypoglycemia symptom filter that is fired at least when the second plurality of survey results indicates that the subject has developed hypoglycemia since receiving their last provision of the dipeptidyl peptidase-4 inhibitor pharmaceutical composition,
    a bodily stress filter that is fired at least when the second plurality of survey results indicates that the subject is experiencing a bodily stress, and
    a second drug interaction filter that is fired at least when the second plurality of survey results indicates that the subject is taking a medication that interacts with the dipeptidyl peptidase-4 inhibitor pharmaceutical composition;
  iv) obtaining acknowledgment from the subject for the warning issued to the subject by any filter in the fourth plurality of filters; and
  v) proceeding with the re-fulfillment process when a) the re-fulfillment process is not already terminated by the firing of a filter in the third plurality of filters and b) the subject has acknowledged each warning associated with each filter in the third plurality of filters that was fired and that is associated with a warning, wherein the re-fulfillment process further comprises:
- storing an indication in the subject profile of a re-order for the dipeptidyl peptidase-4 inhibitor pharmaceutical composition,
- communicating the over the counter drug facts label for the dipeptidyl peptidase-4 inhibitor pharmaceutical composition to the subject, and
- authorizing, upon confirmation from the subject that the over the counter drug facts label has been received and read, a re-order provision of the dipeptidyl peptidase-4 inhibitor pharmaceutical composition to the subject; and F) administering the dipeptidyl peptidase-4 inhibitor pharmaceutical composition to the subject after authorization of the re-order provision.

15. The method of claim 14, wherein the second ceiling blood sugar level used in the second blood sugar filter is 7% glycated hemoglobin.

16. The method of claim 14, wherein, upon a determination that a threshold amount of time has not passed since the last time a blood sugar level of the subject was provided to the system, the method includes bypassing the second blood sugar filter.

17. The method of claim 14, wherein:
- the second plurality of survey results further indicates whether the subject has experienced a side effect from the dipeptidyl peptidase-4 inhibitor pharmaceutical composition since receiving their last provision of the dipeptidyl peptidase-4 inhibitor pharmaceutical composition, and
- the fourth plurality of filters further comprises a side effect filter that is fired at least when the second plurality of survey results indicates that the subject has experienced, since receiving their last provision of the dipeptidyl peptidase-4 inhibitor pharmaceutical composition, a side effect selected from the group consisting of an upper respiratory tract infection, a urinary tract infection, and headaches.

18. The method of claim 14, wherein:
- the second plurality of survey results further indicates whether the subject has developed heart failure since receiving their last provision of the dipeptidyl peptidase-4 inhibitor pharmaceutical composition, and
- the third plurality of filters further comprises a heart failure symptom filter that is fired at least when the second plurality of survey results indicates that the subject has developed, since receiving their last provision of the dipeptidyl peptidase-4 inhibitor pharmaceutical composition, heart failure.

19. The method of claim 1, wherein the lowering blood sugar is to treat Type 2 diabetes and/or maintain sub-diabetic blood sugar levels.

* * * * *